US010793898B2

(12) United States Patent
Lal et al.

(10) Patent No.: US 10,793,898 B2
(45) Date of Patent: Oct. 6, 2020

(54) NANO-SENSORS FOR NUCLEIC ACID DETECTION AND DISCRIMINATION

(71) Applicant: The Regents of the University of California, Oakland, CA (US)

(72) Inventors: Ratneshwar Lal, La Jolla, CA (US); Michael Taeyoung Hwang, La Jolla, CA (US); Preston Boone Landon, Oceanside, CA (US); Gennadi V. Glinskii, La Jolla, CA (US); Alexander Mo, San Diego, CA (US); Srinivasan Ramachandran, Fremont, CA (US); Joon Lee, La Jolla, CA (US); Brian Meckes, Evanston, IL (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/065,701

(22) PCT Filed: Dec. 23, 2016

(86) PCT No.: PCT/US2016/068547
§ 371 (c)(1),
(2) Date: Jun. 22, 2018

(87) PCT Pub. No.: WO2017/112941
PCT Pub. Date: Jun. 29, 2017

(65) Prior Publication Data
US 2019/0256897 A1   Aug. 22, 2019

Related U.S. Application Data

(60) Provisional application No. 62/387,460, filed on Dec. 23, 2015, provisional application No. 62/333,064, filed on May 6, 2016, provisional application No. 62/379,549, filed on Aug. 25, 2016.

(51) Int. Cl.
| *C12Q 1/6816* | (2018.01) |
| *G01N 27/12* | (2006.01) |
| *G01N 27/00* | (2006.01) |
| *C12Q 1/68* | (2018.01) |
| *B82Y 15/00* | (2011.01) |

(52) U.S. Cl.
CPC ............ *C12Q 1/6816* (2013.01); *C12Q 1/68* (2013.01); *G01N 27/00* (2013.01); *G01N 27/125* (2013.01); *G01N 27/128* (2013.01); *B82Y 15/00* (2013.01)

(58) Field of Classification Search
CPC .............................. C12Q 1/6816; G01N 27/00
See application file for complete search history.

(56) References Cited

U.S. PATENT DOCUMENTS

| 9,968,306 B2* | 5/2018 | Cole ...................... A61B 5/746 |
| 2006/0290496 A1* | 12/2006 | Peeters ............ A61B 5/150022 |
| | | 340/572.1 |
| 2010/0234720 A1 | 9/2010 | Tupin, Jr. et al. |
| 2012/0156933 A1 | 6/2012 | Kreger et al. |
| 2012/0214172 A1* | 8/2012 | Chen ..................... B82Y 15/00 |
| | | 435/6.19 |
| 2013/0274135 A1 | 10/2013 | Zhang et al. |
| 2014/0080198 A1* | 3/2014 | Lal ...................... C12N 15/115 |
| | | 435/188 |

FOREIGN PATENT DOCUMENTS

WO        2015178978 A2        11/2015

OTHER PUBLICATIONS

Xu et al, Electrophoretic and field-effect graphene for all-electrical DNA array technology, Nature communications, 2014, 5586, pp. 1-9 (Year: 2014).*
Hwang et al (post art) DNA Nanotweezers and Graphene Transistor Enable Label-Free Genotyping, 2018, Adv. Mater., 30, 1802440, pp. 1-9 (Year: 2018).*
Cai, B. et al., Ultrasensitive Label-Free Detection of PNA-DNA Hybridization by Reduced Graphene Oxide Field-Effect Transistor Biosensor. ACS Nano 8, 2632 (Mar. 25, 2014, 2014).
Chen, F. et al., Electrochemical Gate-Controlled Charge Transport in Graphene in Ionic Liquid and Aqueous Solution. Journal of the American Chemical Society 131, 9908 (Jul. 29, 2009, 2009).
Chen, T.-Y. et al., Label-free detection of DNA hybridization using transistors based on CVD grown graphene. Biosensors and Bioelectronics 41, 103 (Mar. 15, 2013).
Dong, X. et al., "Electrical Detection of DNA Hybridization with Single-Base Specificity Using Transistors Based on CVD-Grown Graphene Sheets", Advanced Materials 22, 2010, pp. 1649-1653.
Du, D. et al., "Graphene-modified electrode for DNA detection via PNA-DNA hybridization", Sensors and Actuators B: Chemical 186, 2013, pp. 563-570.
Green, N.S. et al., "Interactions of DNA with graphene and sensing applications of graphene field-effect transistor devices: A review", Analytica Chimica Acta 853, 2015, pp. 127-142.
Hwang, M.T. et al., "Highly specific SNP sequencing using 2-D graphene electronics and DNA strand displacement", Science, No. 26, vol. 113, 2016, pp. 7088-7093.
Huang, Y. et al., "Nanoelectronic biosensors based on CVD grown graphene", Nanoscale 2, 2010, pp. 1485-1488.
Jain, K.K., "Personalized medicine", Curr Opin Mol Ther 4, 548, 2002, pp. 548-558. (Dec. 2002, 2002).

(Continued)

*Primary Examiner* — Narayan K Bhat
(74) *Attorney, Agent, or Firm* — Perkins Coie LLP

(57) ABSTRACT

Methods, systems, and nano-sensor devices are disclosed for detecting or discriminating nucleic acids with a single nucleotide resolution based on nucleic acid strand displacement. The detection can be made by time-lapse fluorescence measurements or by electro-based graphene FET, which can be combined with wireless communication to provide real-time transmission of the detected signals.

10 Claims, 71 Drawing Sheets

Specification includes a Sequence Listing.

(56) References Cited

OTHER PUBLICATIONS

Khodakov, D.A. et al., "Toehold-Mediated Nonenzymatic DNA Strand Displacement as a Platform for DNA Genotyping", Journal of the American Chemical Society 135, 5612 (Apr. 17, 2013, 2013).
Kujovich, J.L., "Factor V Leiden thrombophilia", Genet Med 13, 2011.
Landon, P.B. et al., "DNA Zipper-Based Tweezers", Langmuir 28, 2012, pp. 534-540. (Jan. 10, 2012, 2012).
Lin, C.-T. et al., "Label-Free Electrical Detection of DNA Hybridization on Graphene using Hall Effect Measurements: Revisiting the Sensing Mechanism", Advanced Functional Materials 23, 2013, pp. 2301-2307.
Matsumoto, K. et al., A Peptide Nucleic Acid (PNA) Heteroduplex Probe Containing an Inosine-Cytosine Base Pair Discriminates a Single-Nucleotide Difference in RNA:, Chemistry—A European Journal 19, 2013, pp. 5034-5040.
Regan, W. et al., "A direct transfer of layer-area graphene", Applied Physics Letters 96, 2010, pp. 113102-1.
Singh, M. et al., "SNP-SNP interactions within APOE gene influence plasma lipids in postmenopausal osteoporosis", Rheumatol Int 31, 2011, pp. 421-423.
Stine, R. et al., "Real-Time DNA Detection Using Reduced Graphene Oxide Field Effect Transistors", Advanced Materials 22, 2010, pp. 5297-5300.
Wolf, A.B. et al., "APOE and neuroenergetics: an emerging paradigm in Alzheimer's disease", Neurobiology of Aging 34, 2013, pp. 1007-1017.
Yin, Z. et al., "Real-time DNA detection using Pt nanoparticle-decorated reduced graphene oxide field-effect transistors", Nanoscale 4, 2012, pp. 293-297.
Zheng, C. et al., "Fabrication of Ultrasensitive Field-Effect Transistor DNA Biosensors by a Directional Transfer Technique Based on CVD-Grown Graphene", ACS Applied Materials & Interfaces 7, 2015, pp. 16953-15959.
International Search Report and Written Opinion for PCT Application No. PCT/US2016/068547, dated Apr. 21, 2017, 13 pages.
Hwang, M.T. et al., "DNA nano-carrier for repeatable capture and release of biomolecules", Nanoscale, vol. 7, No. 41, 2015, pp. 17397-17403.
Miyahata et al., "DNA analysis based on toehold-mediated strang displacement on graphene oxide", Chemical Communications, vol. 49, No. 86, 2013, p. 10139.
Xu et al., "Electrophoretic and field-effect graphene for all-electrical DNA array technology", Nature Communications, vol. 5, 2014, pp. 1-9.
Zhang et al., "A graphene oxide-based enzyme-free signal amplification platform for homogenous DNA detection", The Analyst, vol. 139, No. 19, 2014, pp. 4806-4809.
Extended European Search Report for European Patent Application No. 16880152.0, dated Apr. 15, 2019, 10 pages.

\* cited by examiner

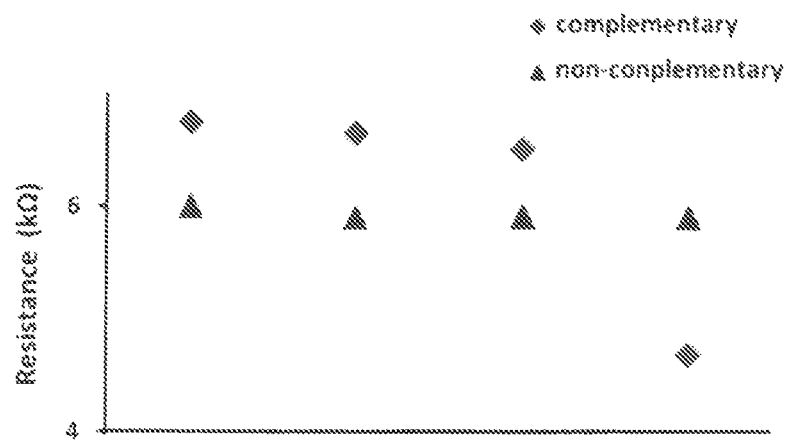
FIG. 18A
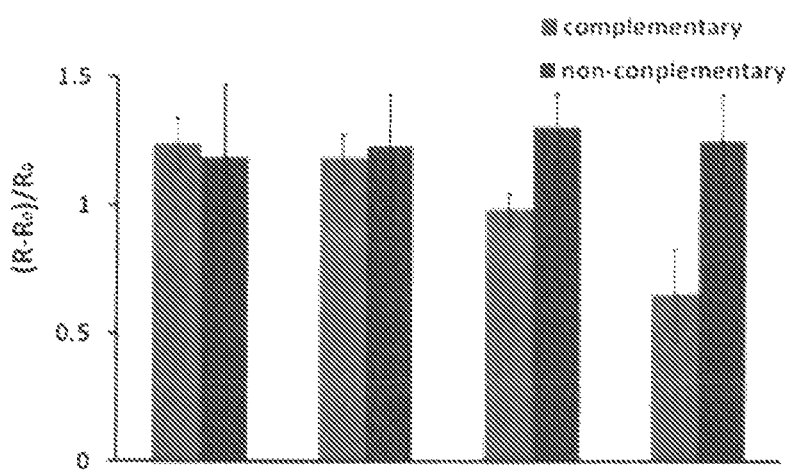
FIG. 18B
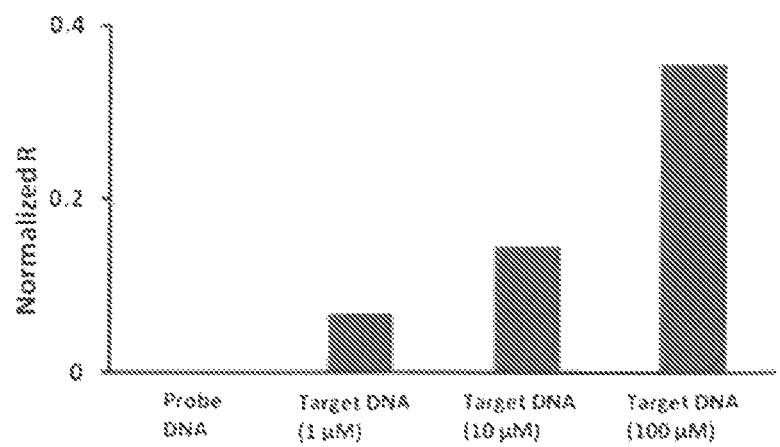
FIG. 18C
FIG. 18

FIG. 22

Device: DNA RS2 with C  (10 nM)
Opening strands: oDNA RS2 or oRNA RS2  (2000, 5000, 10000 nM)
Buffer: No MgCl$_2$

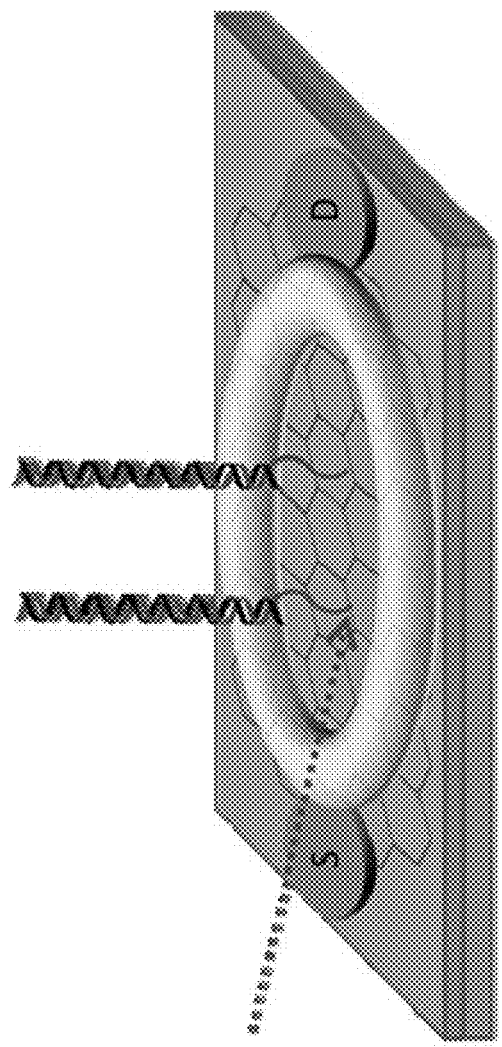
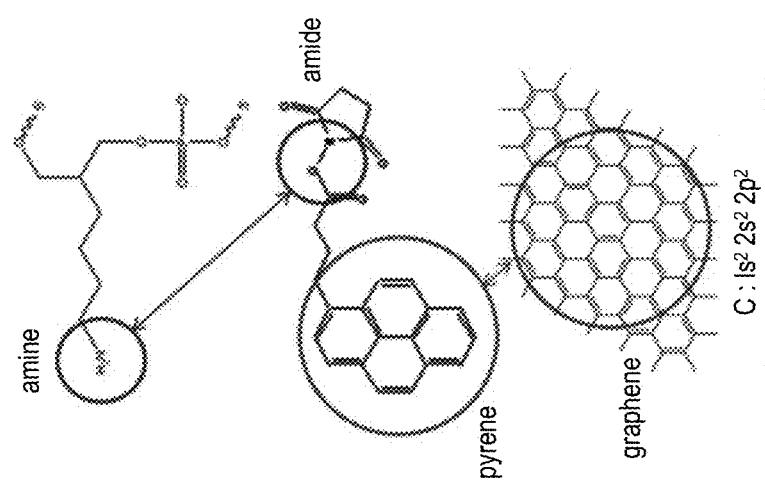
FIG. 35B
FIG. 35A

TDG, thymine DNA glycosylase; TET, ten-eleven-translocation proteins; DNMT, DNA methyltransferases; BER, base excision repair; 5mC, 5-methylcytosine; 5hmC, 5-hydroxymethylcytosine; 5fC, 5-formylcytosine; 5caC, 5-carboxylcytosine Perfect match T: 5'-TGA AAG GGT TTT AAT AAT AGA ATT TTA AAA GAC TGG TAG AAA TAA GG-3'
Single mismatch I: TGA AAG GGT TTT AAT AAT ATA ATT TTA AAA GAC TGG TAG AAA TAA GG 3'

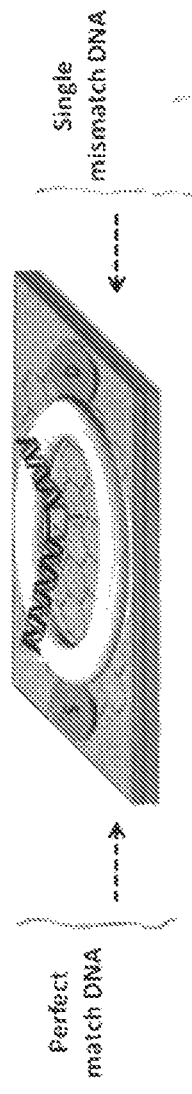
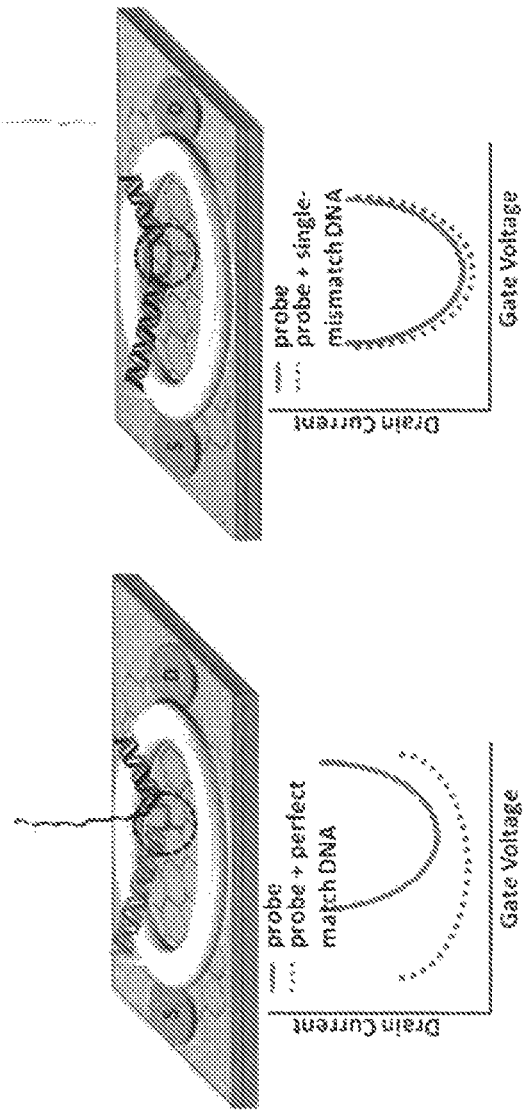
FIG. 54A
FIG. 54B

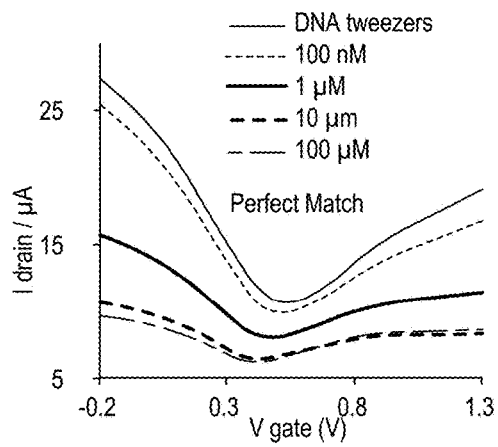
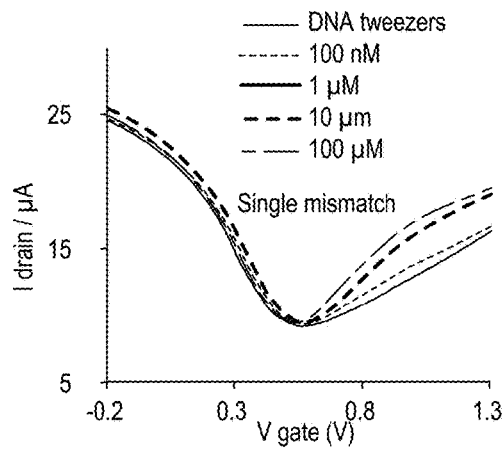
FIG. 57A
FIG. 57B
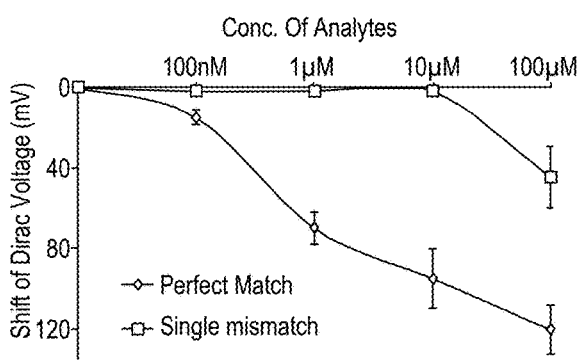
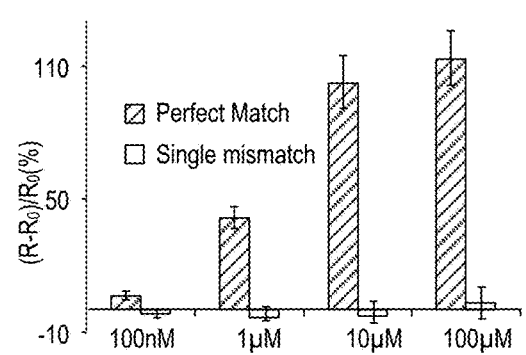
FIG. 57C
FIG. 57D

SEQUENCE LISTING

```
<160> NUMBER OF SEQ ID NOS: 63

<210> SEQ ID NO 1
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acctactcaa ccatacatca ctctacctca aacactcgaa tctcccaaat actaagctgt      60
tcaactcacc                                                            70

<210> SEQ ID NO 2
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cctccagttc caagtaccac catcacacct actcaaccat acatcactct acctcaaaca      60
ctcgaatctc ccaaatacta agctgttcaa ctcacc                               96

<210> SEQ ID NO 3
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
```
ttctggggag tgggagatgt tggctagatt tacggtataa tgaggtagag tgatgtatgg    60
ttgagtaggt                                                           70

<210> SEQ ID NO 4
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (42)..(42)
<223> OTHER INFORMATION: Inosine
<220> FEATURE:
<221> NAME/KEY: modified_base
<222> LOCATION: (44)..(45)
<223> OTHER INFORMATION: Inosine
<220> FEATURE:
<221> NAME/KEY: modified_base
<222> LOCATION: (48)..(48)
<223> OTHER INFORMATION: Inosine
<220> FEATURE:
<221> NAME/KEY: modified_base
<222> LOCATION: (50)..(50)
<223> OTHER INFORMATION: Inosine
<220> FEATURE:
<221> NAME/KEY: modified_base
<222> LOCATION: (52)..(52)
<223> OTHER INFORMATION: Inosine
<220> FEATURE:
<221> NAME/KEY: modified_base
<222> LOCATION: (55)..(55)
<223> OTHER INFORMATION: Inosine
<220> FEATURE:
<221> NAME/KEY: modified_base
<222> LOCATION: (59)..(60)
<223> OTHER INFORMATION: Inosine
<220> FEATURE:
<221> NAME/KEY: modified_base
<222> LOCATION: (63)..(63)
<223> OTHER INFORMATION: Inosine
<220> FEATURE:
<221> NAME/KEY: modified_base
<222> LOCATION: (65)..(65)
<223> OTHER INFORMATION: Inosine
<220> FEATURE:
<221> NAME/KEY: modified_base
<222> LOCATION: (68)..(69)
<223> OTHER INFORMATION: Inosine

<400> SEQUENCE: 4
ttctggggag tgggagatgt tggctagatt tacggtataa tnanntanan tnatntatnn    60 ttnantannt                                                           70

<210> SEQ ID NO 5
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (42)..(42)
<223> OTHER INFORMATION: Inosine
<220> FEATURE:
<221> NAME/KEY: modified_base
<222> LOCATION: (44)..(45)
<223> OTHER INFORMATION: Inosine
<220> FEATURE:
<221> NAME/KEY: modified_base
<222> LOCATION: (48)..(48)

```
<223> OTHER INFORMATION: Inosine
<220> FEATURE:
<221> NAME/KEY: modified_base
<222> LOCATION: (50)..(50)
<223> OTHER INFORMATION: Inosine
<220> FEATURE:
<221> NAME/KEY: modified_base
<222> LOCATION: (52)..(52)
<223> OTHER INFORMATION: Inosine
<220> FEATURE:
<221> NAME/KEY: modified_base
<222> LOCATION: (55)..(55)
<223> OTHER INFORMATION: Inosine
<220> FEATURE:
<221> NAME/KEY: modified_base
<222> LOCATION: (59)..(60)
<223> OTHER INFORMATION: Inosine
<220> FEATURE:
<221> NAME/KEY: modified_base
<222> LOCATION: (63)..(63)
<223> OTHER INFORMATION: Inosine
<220> FEATURE:
<221> NAME/KEY: modified_base
<222> LOCATION: (65)..(65)
<223> OTHER INFORMATION: Inosine
<220> FEATURE:
<221> NAME/KEY: modified_base
<222> LOCATION: (68)..(69)
<223> OTHER INFORMATION: Inosine

<400> SEQUENCE: 5
ttctggggag tgggagatgt tggctagatt tacggtataa tnanntanan tnatntatnn      60
ttnantannt gtgatggtgg tacttggaac tggagg                                 96

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggtgagttga acagcttagt atttgggaga                                        30

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ataccgtaaa tctagccaac atctcccact ccccagaa                               38

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttcgagtgtt tgaggtagag tgatgtatgg ttgagtaggt                             40

<210> SEQ ID NO 9
<211> LENGTH: 38
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 9
cgagtgtttg aggtagagtg atgtatggtt gagtaggt                                  38

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gagtgtttga ggtagagtga tgtatggttg agtaggt                                   37

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agtgtttgag gtagagtgat gtatggttga gtaggt                                    36

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gtgtttgagg tagagtgatg tatggttgag taggt                                     35

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgtttgaggt agagtgatgt atggttgagt aggt                                      34

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtttgaggta gagtgatgta tggttgagta ggt                                       33

<210> SEQ ID NO 15
<211> LENGTH: 32
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 15
tttgaggtag agtgatgtat ggttgagtag gt                                      32

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ttgaggtaga gtgatgtatg gttgagtagg t                                       31

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgaggtagag tgatgtatgg ttgagtaggt                                         30

<210> SEQ ID NO 18
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(28)
<223> OTHER INFORMATION: Inosine
<220> FEATURE:
<221> NAME/KEY: modified_base
<222> LOCATION: (30)..(30)
<223> OTHER INFORMATION: Inosine
<220> FEATURE:
<221> NAME/KEY: modified_base
<222> LOCATION: (33)..(33)
<223> OTHER INFORMATION: Inosine
<220> FEATURE:
<221> NAME/KEY: modified_base
<222> LOCATION: (37)..(37)
<223> OTHER INFORMATION: Inosine
<220> FEATURE:
<221> NAME/KEY: modified_base
<222> LOCATION: (40)..(40)
<223> OTHER INFORMATION: Inosine
<220> FEATURE:
<221> NAME/KEY: modified_base
<222> LOCATION: (43)..(44)
<223> OTHER INFORMATION: Inosine
<220> FEATURE:
<221> NAME/KEY: modified_base
<222> LOCATION: (48)..(49)
<223> OTHER INFORMATION: Inosine
<220> FEATURE:
<221> NAME/KEY: modified_base
<222> LOCATION: (53)..(53)
<223> OTHER INFORMATION: Inosine
<220> FEATURE:
<221> NAME/KEY: modified_base
<222> LOCATION: (56)..(56)
<223> OTHER INFORMATION: Inosine
<220> FEATURE:
```

```
<221> NAME/KEY: modified_base
<222> LOCATION: (58)..(59)
<223> OTHER INFORMATION: Inosine
<220> FEATURE:
<221> NAME/KEY: modified_base
<222> LOCATION: (62)..(64)
<223> OTHER INFORMATION: Inosine

<400> SEQUENCE: 18
gccatagtta gagcatgcgc catagtnntn ttntttnttn ttnntttnnt ttntttntnnt    60 tnnntccctt ccgaatgcag ctgccattcc gaatgc                                96

<210> SEQ ID NO 19
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cgcaatccac cgatcatccg caatccaaat ctcccaacca caacaaacca aaccaacaac    60
aaacaacacc actatggcgc atgctctaac tatggc                               96

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggtgttgttt gttgttggtt tggtttgttg tggtttttag atttggattg aagtgagcgt    60

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
acgctcactt aaatctaaaa accacaacaa accaaaccaa caacaaac                 48

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aagggaccca accacaa                                                    17

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
``` tttttttaagg gacccaacca caa                                              23

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24 tttttttaagg acccaaccac aa                                               22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cggatgatcg gtggattgcg                                                   20

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcattcggaa tggcagctgc attc                                              24

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcattcggaa tggcagctgc attcttt                                           27

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cggatgatcg gtggattgcg ttt                                               23

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgcattcgga atggcagctg cattc                                             25

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggtgttgttt gttgttggtt tggtttgttg tggttgggag atttggattg aagtgagcgt      60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggtgttgttt gttgttggtt tggtttgtta taattaaaag atttggattg aagtgagcgt      60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggtgttgttt gttattaatt taatttatta taattaaaag atttggattg aagtgagcgt      60

<210> SEQ ID NO 33
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
acgctcactt caatccaaat ctaaaaacca caacaaacca aaccaacaac aa               52

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34 ttttttaag ggacccaacc acaa                                               24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 ttttttaag ggacccaacc acaa                                               24

```
<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tttttttaag ggacccaacc acaa                                          24

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gcattcggaa tggcagctgc attcggt                                       27

<210> SEQ ID NO 38
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Inosine
<220> FEATURE:
<221> NAME/KEY: modified_base
<222> LOCATION: (31)..(31)
<223> OTHER INFORMATION: Inosine
<220> FEATURE:
<221> NAME/KEY: modified_base
<222> LOCATION: (35)..(35)
<223> OTHER INFORMATION: Inosine
<220> FEATURE:
<221> NAME/KEY: modified_base
<222> LOCATION: (39)..(39)
<223> OTHER INFORMATION: Inosine

<400> SEQUENCE: 38
tgaaagngtt ttaataatag aattttaaaa nactngtana tttttttttt ctctatcaat   60
ctctaacacc c                                                        71

<210> SEQ ID NO 39
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gggtgttaga gattgataga gcggccttat ttctaccagt cttttaaaat tctattatta   60 aaacccttto a                                                        71

<210> SEQ ID NO 40
<211> LENGTH: 47
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 40
tgaaagggtt ttaataatag aattttaaaa gactggtaga aataagg         47

<210> SEQ ID NO 41
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgaaagggtt ttaataatat aattttaaaa gactggtaga aataagg         47

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
taataataga attttaaaag actggaataa                             30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ttattccagt cttttaaaat tctattatta                             30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
actgatgcac tgattacctg ctacgatcga                             30

<210> SEQ ID NO 45
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gggtgttaga gattgataga gcggccttat ccagtatttt aaaattctat tatta   55

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (20)..(20)
<223> OTHER INFORMATION: Inosine
<220> FEATURE:
<221> NAME/KEY: modified_base
<222> LOCATION: (24)..(25)
<223> OTHER INFORMATION: Inosine

<400> SEQUENCE: 46
taataaatna attttaaaan actnnttttt tttttctcta tcaatctcta acaccc        56

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
taataataga attttaaaag actggaataa                                      30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
taataataga agtttaaaag actggaataa                                      30

<210> SEQ ID NO 49
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gggtgttaga gattgataga gcggccttat tccagtcttt taaaattcta ttatta        56

<210> SEQ ID NO 50
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (20)..(20)
<223> OTHER INFORMATION: Inosine
<220> FEATURE:
<221> NAME/KEY: modified_base
<222> LOCATION: (24)..(25)
<223> OTHER INFORMATION: Inosine

<400> SEQUENCE: 50
taataatana attttaaaan actnnttttt ttttctctca tcaatctcta acaccc        56

<210> SEQ ID NO 51
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (27)..(28)
<223> OTHER INFORMATION: Inosine
<220> FEATURE:
<221> NAME/KEY: modified_base
<222> LOCATION: (30)..(30)
<223> OTHER INFORMATION: Inosine
<220> FEATURE:
<221> NAME/KEY: modified_base
<222> LOCATION: (33)..(33)
<223> OTHER INFORMATION: Inosine
<220> FEATURE:
<221> NAME/KEY: modified_base
<222> LOCATION: (37)..(37)
<223> OTHER INFORMATION: Inosine
<220> FEATURE:
<221> NAME/KEY: modified_base
<222> LOCATION: (40)..(40)
<223> OTHER INFORMATION: Inosine
<220> FEATURE:
<221> NAME/KEY: modified_base
<222> LOCATION: (43)..(44)
<223> OTHER INFORMATION: Inosine
<220> FEATURE:
<221> NAME/KEY: modified_base
<222> LOCATION: (48)..(49)
<223> OTHER INFORMATION: Inosine
<220> FEATURE:
<221> NAME/KEY: modified_base
<222> LOCATION: (53)..(53)
<223> OTHER INFORMATION: Inosine
<220> FEATURE:
<221> NAME/KEY: modified_base
<222> LOCATION: (56)..(56)
<223> OTHER INFORMATION: Inosine
<220> FEATURE:
<221> NAME/KEY: modified_base
<222> LOCATION: (58)..(59)
<223> OTHER INFORMATION: Inosine
<220> FEATURE:
<221> NAME/KEY: modified_base
<222> LOCATION: (62)..(64)
<223> OTHER INFORMATION: Inosine

<400> SEQUENCE: 51
gccatagtta gagcatgcgc catagtnntn ttntttnttn ttnntttnnt ttnttntnnt        60 tnnntccctt        70

<210> SEQ ID NO 52
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
caatccaaat ctcccaacca caacaaacca aaccaacaac aaacaacacc actatggcgc        60
atgctctaac tatggc        76

<210> SEQ ID NO 53
<211> LENGTH: 25

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (20)..(20)
<223> OTHER INFORMATION: Inosine
<220> FEATURE:
<221> NAME/KEY: modified_base
<222> LOCATION: (24)..(25)
<223> OTHER INFORMATION: Inosine

<400> SEQUENCE: 53
uaauaauana auuuuaaaan acunn                                        25

<210> SEQ ID NO 54
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ccagucuuuu aaaauucuau uauuaaaacc cucuu                             35

<210> SEQ ID NO 55
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ggguuuuaau aauagaauuu uaaaagacug g                                 31

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ccagtctttt aaaattctat tatta                                        25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
taataataga attttaaaag actgg                                        25

<210> SEQ ID NO 58
<211> LENGTH: 25
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 58
uaauaauaga auuuuaaaag acugg                                            25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (20)..(20)
<223> OTHER INFORMATION: Inosine
<220> FEATURE:
<221> NAME/KEY: modified_base
<222> LOCATION: (24)..(25)
<223> OTHER INFORMATION: Inosine

<400> SEQUENCE: 59
taataatana attttaaaan actnn                                            25

<210> SEQ ID NO 60
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60 ccagtcttttt aaaattctat tattaaaacc ctctt                                35

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gggttttaat aatagaattt taaaagactg g                                     31

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: Inosine
<220> FEATURE:
<221> NAME/KEY: modified_base
<222> LOCATION: (31)..(31)
<223> OTHER INFORMATION: Inosine
<220> FEATURE:
<221> NAME/KEY: modified_base
<222> LOCATION: (35)..(35)
<223> OTHER INFORMATION: Inosine
```

```
<220> FEATURE:
<221> NAME/KEY: modified_base
<222> LOCATION: (39)..(39)
<223> OTHER INFORMATION: Inosine

<400> SEQUENCE: 62
tgaaagngtt ttaataatag aattttaaaa nactngtana                    40

<210> SEQ ID NO 63
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccttatttct accagtcttt taaaattcta ttattaaaac cctttca            47
```

NANO-SENSORS FOR NUCLEIC ACID DETECTION AND DISCRIMINATION

CROSS-REFERENCE TO RELATED APPLICATIONS

This patent document is a 371 National Phase Application of PCT Application No. PCT/US2016/068547, entitled "NANO-SENSORS FOR NUCLEIC ACID DETECTION AND DISCRIMINATION", filed on Dec. 23, 2016, which claims benefits and priorities of (1) U.S. Provisional Patent Application No. 62/387,460, entitled "HIGHLY SPECIFIC SNP SEQUENCING USING 2-D GRAPHENE ELECTRONICS AND DNA STRAND DISPLACEMENT," filed on Dec. 23, 2015, (2) U.S. Provisional Patent Application No. 62/379,549, entitled "HIGHLY SPECIFIC SNP DETECTION METHOD USING 2-D GRAPHENE ELECTRONICS AND DNA STRAND DISPLACEMENT," filed on Aug. 25, 2016, and (3) U.S. Provisional Patent Application No. 62/333,064, entitled "NANO-SENSORS FOR SINGLE-NUCLEOTIDE-RESOLUTION NUCLEIC ACIDS DETECTION AND DISCRIMINATION," filed on May 6, 2016. The entire contents of the aforementioned patent applications are incorporated by reference as part of the disclosure of this patent document.

STATEMENT REGARDING FEDERALLY SPONSORED RESEARCH OR DEVELOPMENT

This invention was made with government support under DA024871D and A025296, awarded by the National Institute on Drug Abuse (NIDA) of the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Apr. 18, 2019, is named 009062-8320_US02_SL.txt and is 19,962 bytes in size.

TECHNICAL FIELD

This patent document relates to nano-sensors and techniques for detection and discrimination of nucleic acids.

BACKGROUND

Diseases from genetic mutations can start with a single recombination error. Early diagnosis of the single mutation is key to preventing and treating the diseases. DNA sequencing has been of great interest for diagnosis of genetic disease, biological informatics, forensics, and environmental monitoring. Discrimination of a single mismatch in a long DNA strand is of significant importance because it enables detection of single nucleotide polymorphism (SNP). An SNP is a single nucleotide mutation in a gene and varies among members of a biological species or paired chromosomes. These mutations can be used as markers for variety of diseases, including various forms of cancer, genetic disease, and personalized medicine. The small change that an SNP causes can have dramatic influence on the health. Thus it is desirable to detect these mutations with high sensitivity and specificity draws great attention.

SUMMARY

Disclosed are methods, systems, and devices for detecting or discriminating specific nucleic acid molecules for diagnosis of diseases such as cancer or genetic diseases, forensics, or preparation of personalized medicines.

In one aspect, disclosed is an electro-based nucleic acid detection device, e.g., an electrical biosensor using graphene FET. The device comprises a graphene chip, a microcontroller board for measuring electric current passing through the graphene chip when an input voltage is applied to the graphene chip, and a mobile device to receive the transmitted measurements. In some embodiments, the graphene chip includes a substrate, a graphene surface on the substrate, a conducting substance at two ends of the graphene surface to form a first electrode and a second electrode, and an insulating substance to insulate the first electrode and the second electrode. The insulating substance further forms a solution reservoir on the graphene surface to receive nucleic acid samples. In some embodiments, the microcontroller board includes a digital meter to measure the electric current that passes through the graphene chip when an input voltage is applied to the graphene chip, and a communication module to send the measured electric current and the input voltage. The mobile device receives the measured electric current from the communication module and processes the measured electric current to show resistance changes. In some embodiments, an analytical wireless communication platform is added to the electrical biosensor to enable real-time transmission of detected molecular signals. The electrical signal resulting from resistance changes triggered by probe and target nucleic acid binding in the solution reservoir of the device is captured and transmitted remotely using the microcontroller board and communicated in real time by wireless communication via Bluetooth standard to personal electronics, including smart phones, tablets or computers.

In some embodiments, nucleic acid detection is achieved by measuring changes in Dirac-point shift in IV curve and resistance change due to the hybridization of a probe nucleic acid and a target nucleic acid sequentially added to the reservoir of the device. In some embodiments, the nucleic acid probe is a double-stranded nucleic acid probe such as DNA zippers and DNA tweezers.

In a related aspect, disclosed is an electro-based method of detecting or discriminating a nucleic acid. The method entails the steps of contacting a nucleic acid probe with a solution reservoir on a graphene chip such that the probe is immobilized onto the graphene surface, for example, by π-π stacking and amine-amide bonding, contacting a target nucleic acid with the solution reservoir, applying an input voltage on the graphene chip to generate an electric current that passes through the solution reservoir containing the probe nucleic acid and the target nucleic acid, measuring the electric current change triggered by hybridization or partial hybridization of the target nucleic acid to the probe nucleic acid. In some embodiments, the measured electrical signals are transmitted to a mobile device in real time by wireless communication. In some embodiments, the probe nucleic acid is a DNA tweezers-based probe and the electrical signal-based detection is triggered by DNA strand displacement with a target nucleic acid that drives the strand displacement and opening of the DNA tweezers attached to the surface of the graphene chip. Opening of the DNA tweezers causes the switching of varied lengths of nucleic acid strands, which results in a charge difference before and after strand displacement. The changes in the measured resistance and Dirac-point of the graphene are processed and analyzed.

In some embodiments, a nucleic acid probe is attached on a graphene FET and a liquid gate is used to obtain I-V curve with the nucleic acid in the solution reservoir. I-V curve shifts and changes in resistance are monitored with fully complementary (perfect match) control nucleic acid and target nucleic acid having one or more mismatches. In other words, the I-V curve of the binding of the probe nucleic acid and a control nucleic acid having a sequence that is fully complementary to the probe is compare to the I-V curve of the binding of the probe nucleic acid and a target nucleic acid having one or more mismatches with probe. The I-V curve shifting from the control indicating the presence of one or more mismatches. The disclosed technology is capable of identifying a single mismatch in a target nucleic acid having a length of at least 15 nt, at least 20 nt, at least 25 nt, at least 30 nt, at least 35 nt, at least 40 nt, at least 45 nt, at least 47 nt, at least 50 nt, at least 55 nt, at least 60 nt, at least 65 nt, at least 70 nt, at least 75 nt, at least 80 nt, at least 85 nt, at least 90 nt, at least 95 nt, or at least 100 nt.

In another aspect, disclosed is a fluorescence-based method of detecting or discriminating a nucleic acid. The method entails the steps of: contacting a probe nucleic acid with a control nucleic acid that is fully complementary to the probe, measuring the kinetics of strand displacement of the probe and the control nucleic acid; contacting the probe nucleic acid with a target nucleic acid having one or more mismatches with the probe, measuring the kinetics of strand displacement of the probe and the target nucleic acid, comparing the kinetics of the control and the target, wherein a change in the kinetics indicating the presence of one or more mismatches in the target nucleic acid. In some embodiments, the probe nucleic acid is a double-stranded nucleic acid comprising a normal strand and a weak strand. In some embodiments, a fluorescent label is attached to one end of the weak strand. In some embodiments, a quencher is attached to one end of the normal strand.

For the technology and devices disclosed herein, in some embodiments, the nucleic acid probe or the target nucleic acid employed by the disclosed technology and device has a length of at least 10 nt, at least 11 nt, at least 12 nt, at least 13 nt, at least 14 nt, at least 15 nt, at least 16 nt, at least 17 nt, at least 18 nt, at least 19 nt, at least 20 nt, at least 21 nt, at least 22 nt, at least 23 nt, at least 24 nt, at least 25 nt, at least 26 nt, at least 27 nt, at least 28 nt, at least 29 nt, at least 30 nt, at least 31 nt, at least 32 nt, at least 33 nt, at least 34 nt, at least 35 nt, at least 36 nt, at least 37 nt, at least 38 nt, at least 39 nt, at least 40 nt, at least 41 nt, at least 42 nt, at least 43 nt, at least 44 nt, at least 45 nt, at least 46 nt, at least 47 nt, at least 48 nt, at least 49 nt, at least 50 nt, at least 55 nt, or at least 60 nt. The probe nucleic acid and the target nucleic acid can have the same length or a similar length.

For the technology and devices disclosed herein, in some embodiments, the nucleic acid probe is a double-stranded probe comprising a normal strand and a weak strand. The normal strand is complementary or partially complementary to a target nucleic acid. In some embodiments, the normal strand has a toehold comprising one or more nucleotide not complementary to the weak strand. In some embodiments, the weak strand comprises one or more guanines or deoxyguanines replaced by inosines or deoxyinosines. Nucleotides other than inosine and deoxyinosine having a weaker affinity to guanines than the normal G-C pairing can be used. In some embodiments, the normal strand and the weak strand are bound through a hinge region that is completely complementary to each other.

BRIEF DESCRIPTION OF THE DRAWINGS

FIG. 3 discloses SEQ ID NOS 47, 49 and 50, respectively, in order of appearance.

FIG. 5A shows schematics of strand displacement: nucleotide with fluorophore and nucleotide with quencher are shown. Initially, the normal (N) and weak (W) strands are hybridized; fluorophore and quencher are adjacent so that fluorescence is quenched. When the perfect-match target strand (T) interacts with the DNA tweezers, strand displacement takes place, causing N strand and perfect-match target strand to hybridize. Though W is bound by hinge, it is away from the N and the fluorophore becomes active. FIG. 5B shows real-time fluorescence measurement of the strand displacement. Interaction of the single-mismatch target strand with DNA tweezers shows much less fluorescence activity than the interaction of the perfect match with DNA tweezers. The concentration of DNA tweezers is 20 nM, and the concentration of T strand is 100 nM.

FIG. 18 shows three sets of data: FIG. 18A is an example of raw data set of resistance change induced by DNA; FIG. 18B is an example of statistical data of resistance change due to DNA detection; and FIG. 18C is an example of normalized resistance demonstrating clear discrimination between complementary and non-complementary target strands.

FIG. 20 discloses SEQ ID NOS 22, 51, 52, 20, 22, 51, 52, 20, 33, 20 and 33, respectively, in order of appearance.

FIG. 21 discloses SEQ ID NOS 37, 25, 18, 19 and 35, respectively, in order of appearance.

FIG. 22 shows an example schematic of the DNA strands used for the gel electrophoresis experiments. FIG. 22 discloses SEQ ID NOS 18, 19 and 35, respectively, in order of appearance.

FIG. 23 discloses SEQ ID NOS 29, 28, 18, 19, 35, 29, 28, 18, 19, and 35, respectively, in order of appearance.

FIG. 28A demonstrates that DNA-DNA binding and RNA-RNA binding are more favorable than DNA-RNA binding, and that RNA RS2 device with RNA opening strands opens faster than DNA device with DNA opening strands. FIG. 28B discloses SEQ ID NOS 53-55, respectively, in order of appearance.

FIG. 29A demonstrates that RNA oRS2-10 and DNA oRS2-10 displace the DNA[N]:RNA[W] hybrid RS2-10 at a similar rate, and that RNA oRS2-10 and DNA oRS2-10 displace the RNA[N]:DNA[W] hybrid RS2-10 at a similar rate. FIG. 29A discloses SEQ ID NOS 56, 53, 57, 58, 54, 59, 57 and 58, respectively, in order of appearance. FIG. 29B demonstrates that RNA oRS2-10+6 displace the 10toeDNA [N]:RNA[W] hybrid RS2-10 at a similar rate. FIG. 29B discloses SEQ ID NOS 60, 53, 55 and 61, respectively, in order of appearance. FIG. 29C demonstrates that oRNA+6 displaces the RNA[N]:DNA[W] hybrid RS2-10 faster than oDNA+6 by a factor of 2. FIG. 29C discloses SEQ ID NOS 54, 59, 55 and 61, respectively, in order of appearance.

FIG. 31 shows time-lapse fluorescence of the device at different temperatures and concentrations.

C. with 40 nM and 600 nM of samples respectively. The top line in each plot shows the maximum fluorescence without any quenchers present in the system.

FIG. 32 shows the effect of the number of mismatches on capture and release operation. The length of mismatch sequences affects affinity between R and F as well as T and F. FIG. 32A illustrates the capture state of the device. Arrow shows the location of a mismatch between R and F. FIG. 32B shows that when there is no mismatch between R and F, transition to the capture state does not occur, and the fluorescence signal does not decrease as T binds to F and remains in the closed state. FIG. 32C shows the normal operation of capture when there are 3 consecutive mismatches between R and F. FIGS. 32D and 32E show that F with 6 (32D) and 12 (32E) mismatches cannot open the DNA tweezers fully reducing the capture efficiency of T.

Figure 33A:
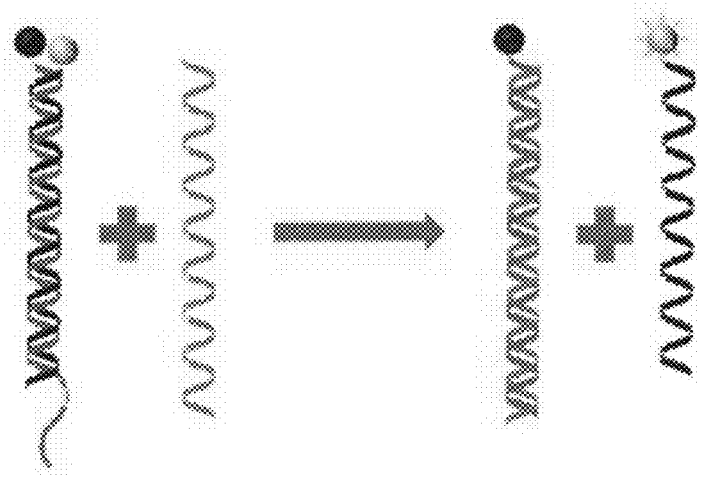
Figure 33B:
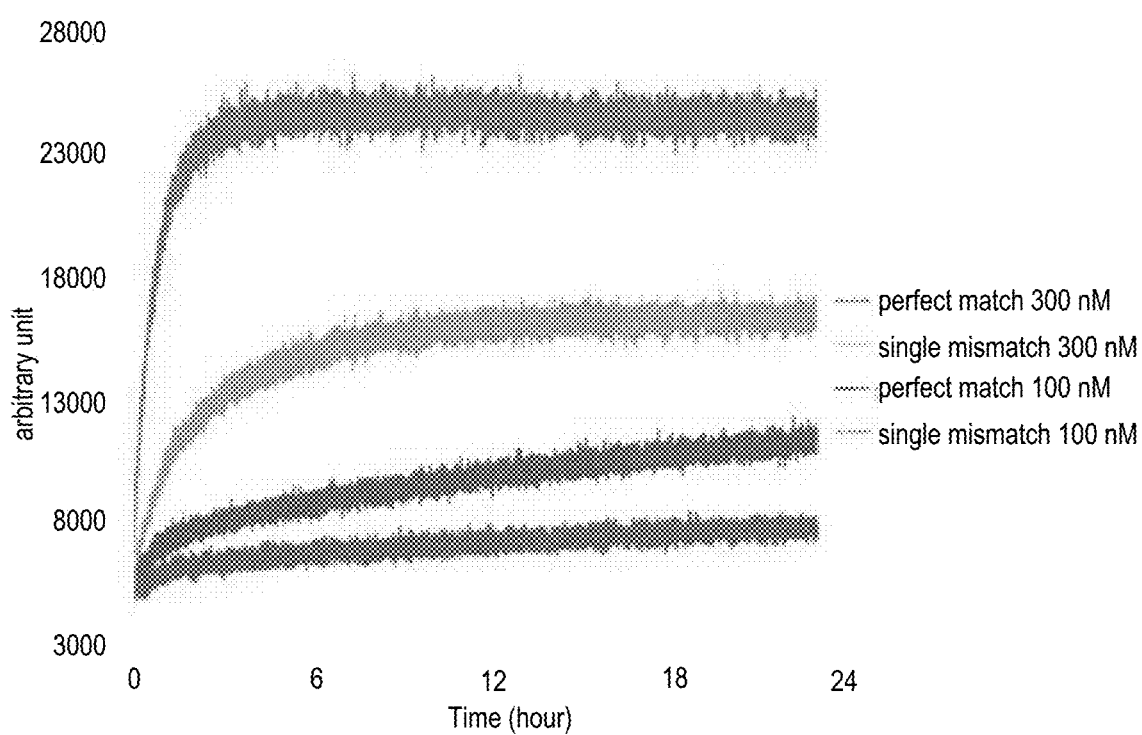

FIG. 33A shows an example of strand displacement with fluorescent label and quencher. Initially the N and W strands are hybridized and fluorophore and quencher are adjacent so that fluorescence is quenched. The initial hybridized double-strand is, namely, double-strand probe (DS probe). When perfect match T strand meets the DS probe, strand displacement happens and N and perfect match T hybridize. W is left single-stranded and fluorescent label is active. FIG. 33B shows real time fluorescent measurement of strand displacement. The single mismatch T did not operate strand displacement efficiently as much as the perfect match T. The concentration of DS probe was 10 nM and the concentrations of Ts are shown in legend.

Figure 34:
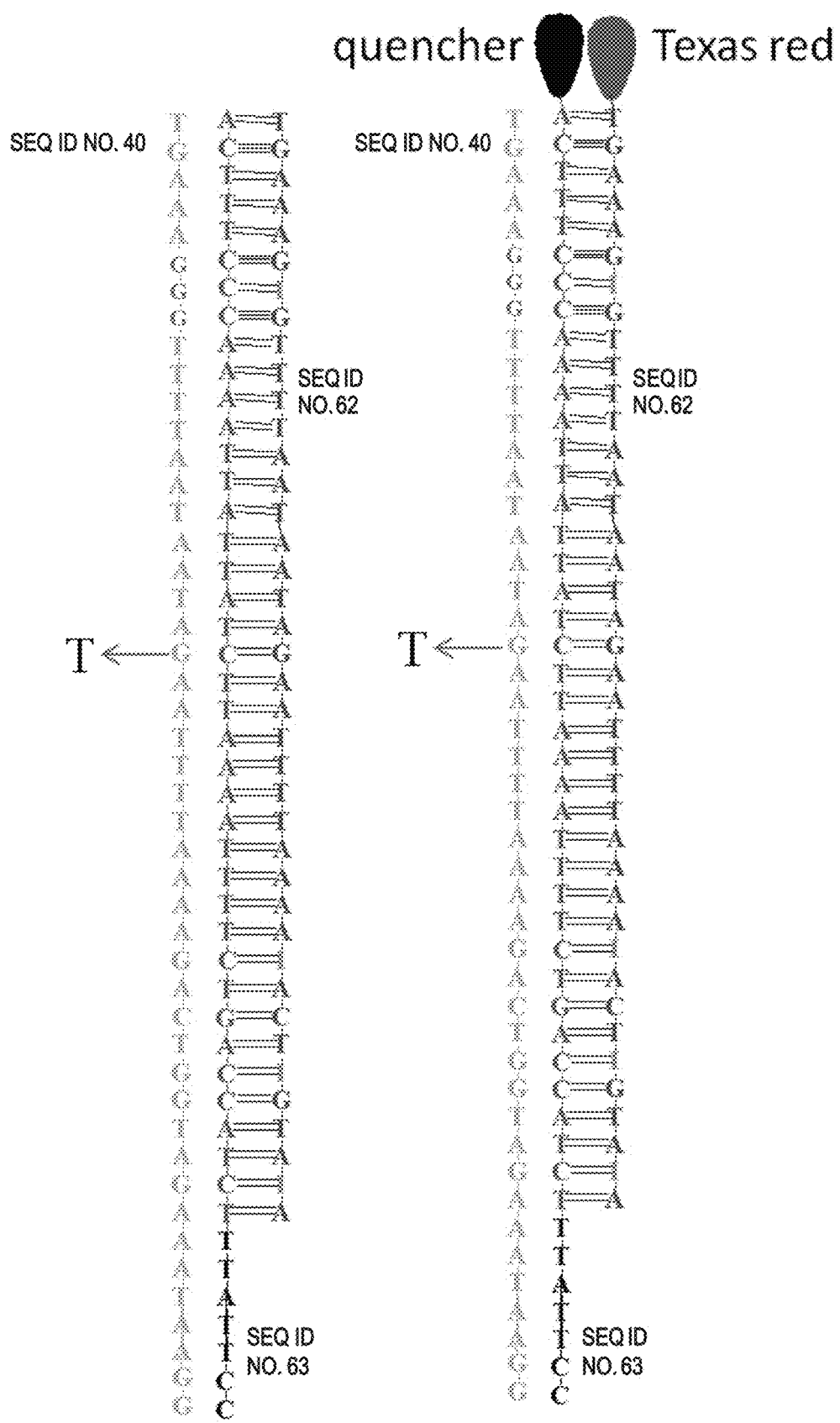

FIG. 34 shows the structure of an example DS probe with specific sequences. The complementary target strand and one mismatch T having a T instead of a G in the middle of the sequence are shown. The W strand contains 4 Is. The set of sequences on the left is used in FET experiment and the set on the right is used in fluorescence experiment. The quencher and Texas red fluorophore are shown. FIG. 34 discloses SEQ ID NOS 40, 63, 62, 40, 63 and 62, respectively, in order of appearance.

FIG. 35A shows an example of DNA functionalization process. FIG. 35B shows that the DNA zipper is functionalized on the graphene FET. The dash line indicates where the functionalization processes.

Figure 36:
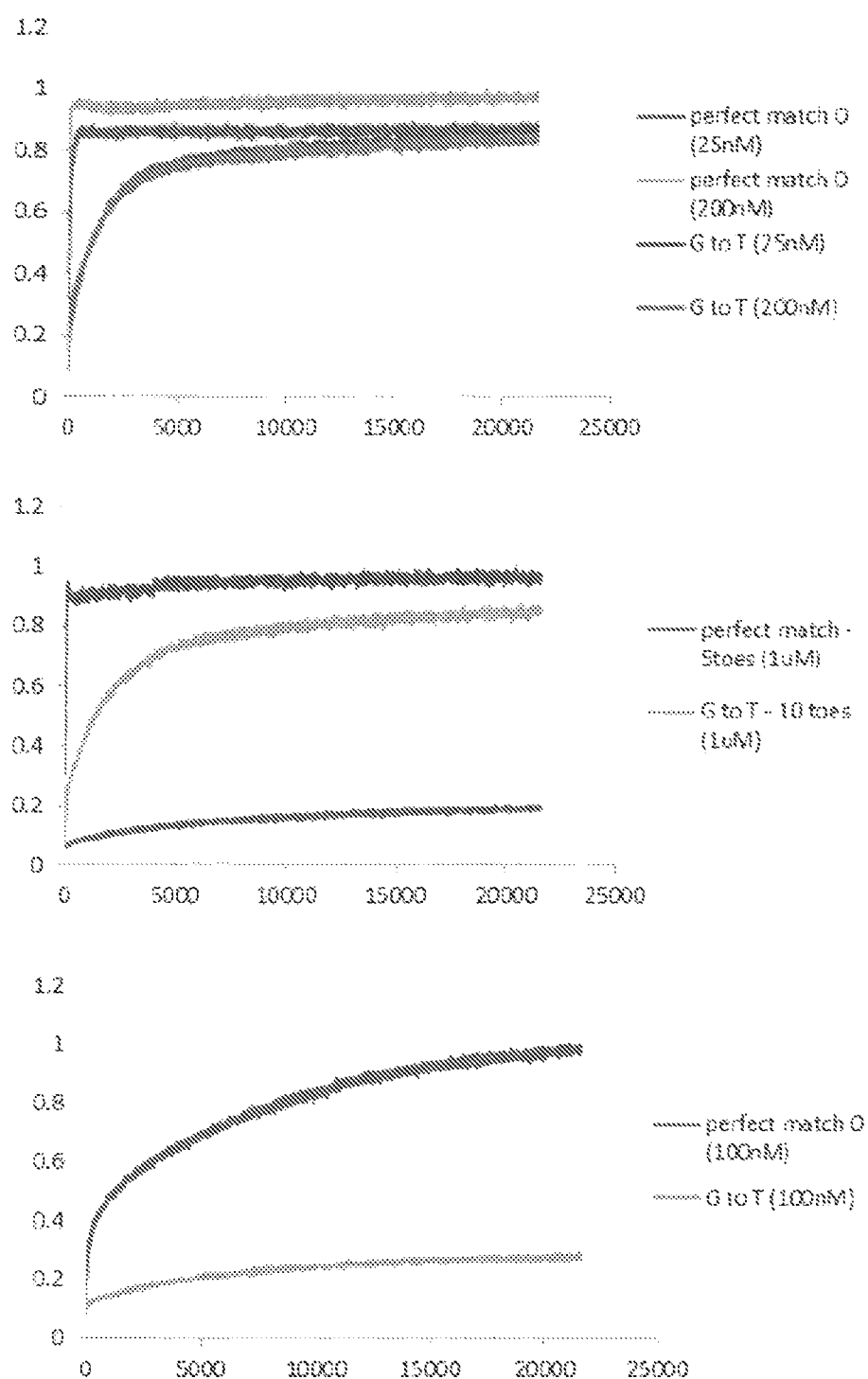

FIG. 36 illustrates fluorescence test with different toehold lengths. 10 nt and 5 nt of toeholds were used. X-axis is time with second scale and Y axis is arbitrary unit of fluorescence. The concentration of DS probe was 20 nM and concentrations of target strands are shown in the legend. G to T means single mismatch which is substituted G to T.

Figure 37:
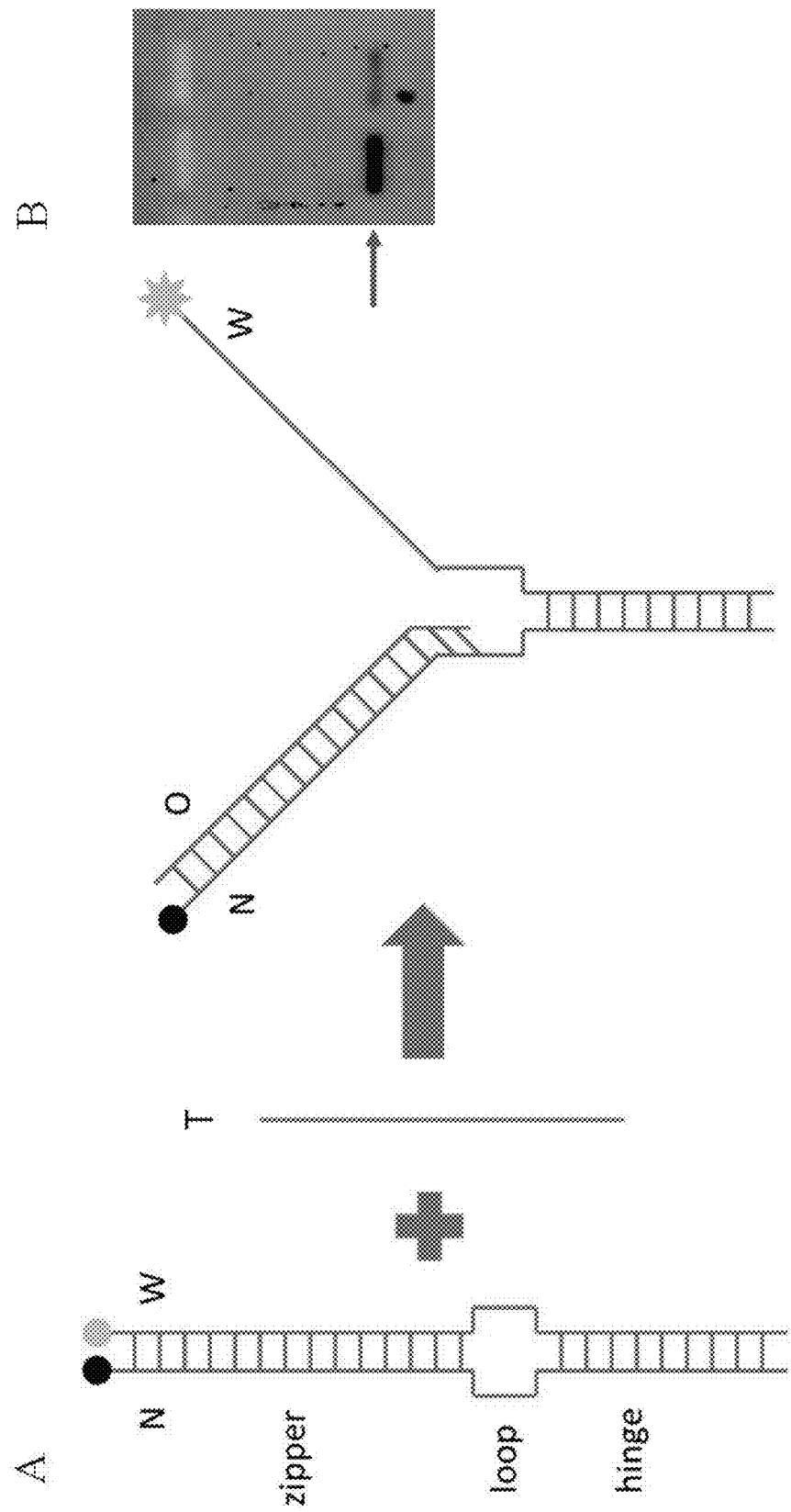
Figure 37:
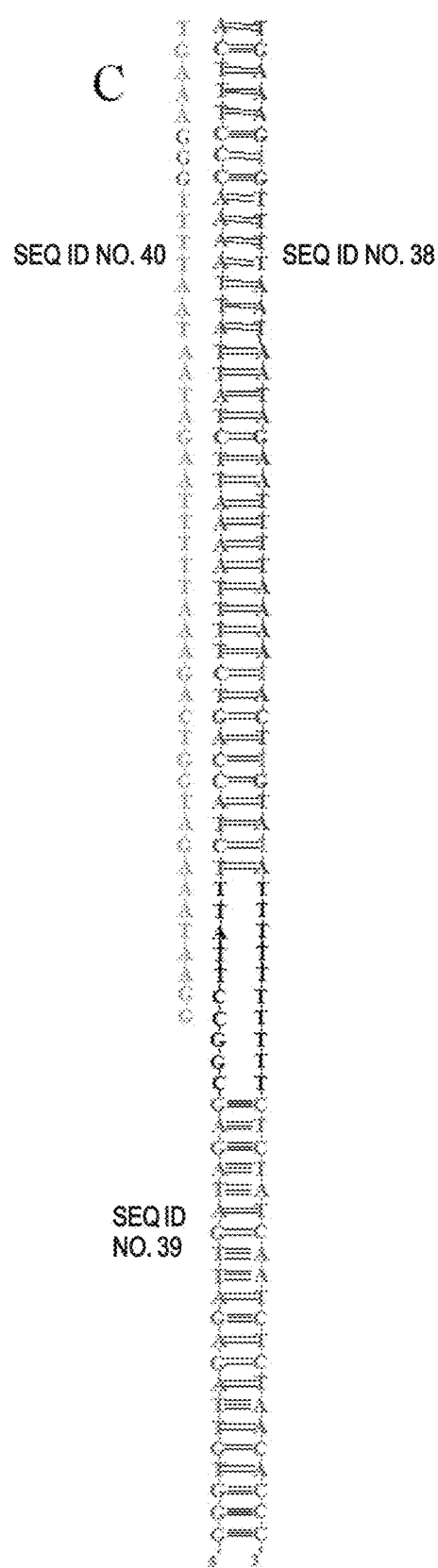

FIG. 37 illustrates modification of DS probe as DNA tweezers for gel electrophoresis analysis. FIG. 37A shows that the hinge part is added to bound DS probe part when it is displaced. The partial triple strand is stably constructed. The displacement reaction is not affected by the hinge as there is 10 nt of loop part. FIG. 37B shows that single mismatch discrimination was tested in gel electrophoresis. The left lane shows strand displacement of DNA tweezers by complementary T and the right lane by single mismatch T. FIG. 37C shows the specific sequences and structure of DNA tweezers. FIG. 37 discloses SEQ ID NOS 40, 39 and 38, respectively, in order of appearance.

Figure 38A:
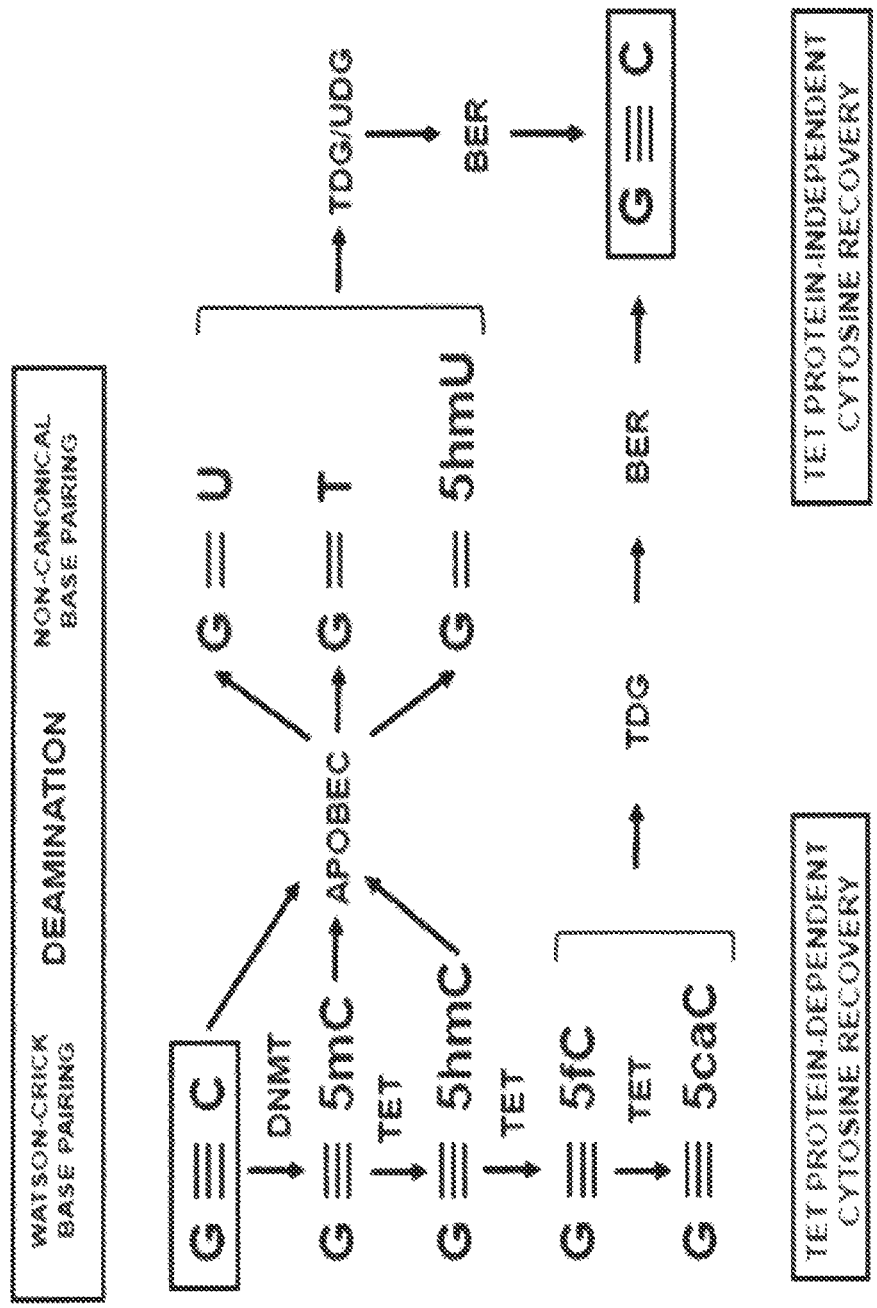
Figure 38B:
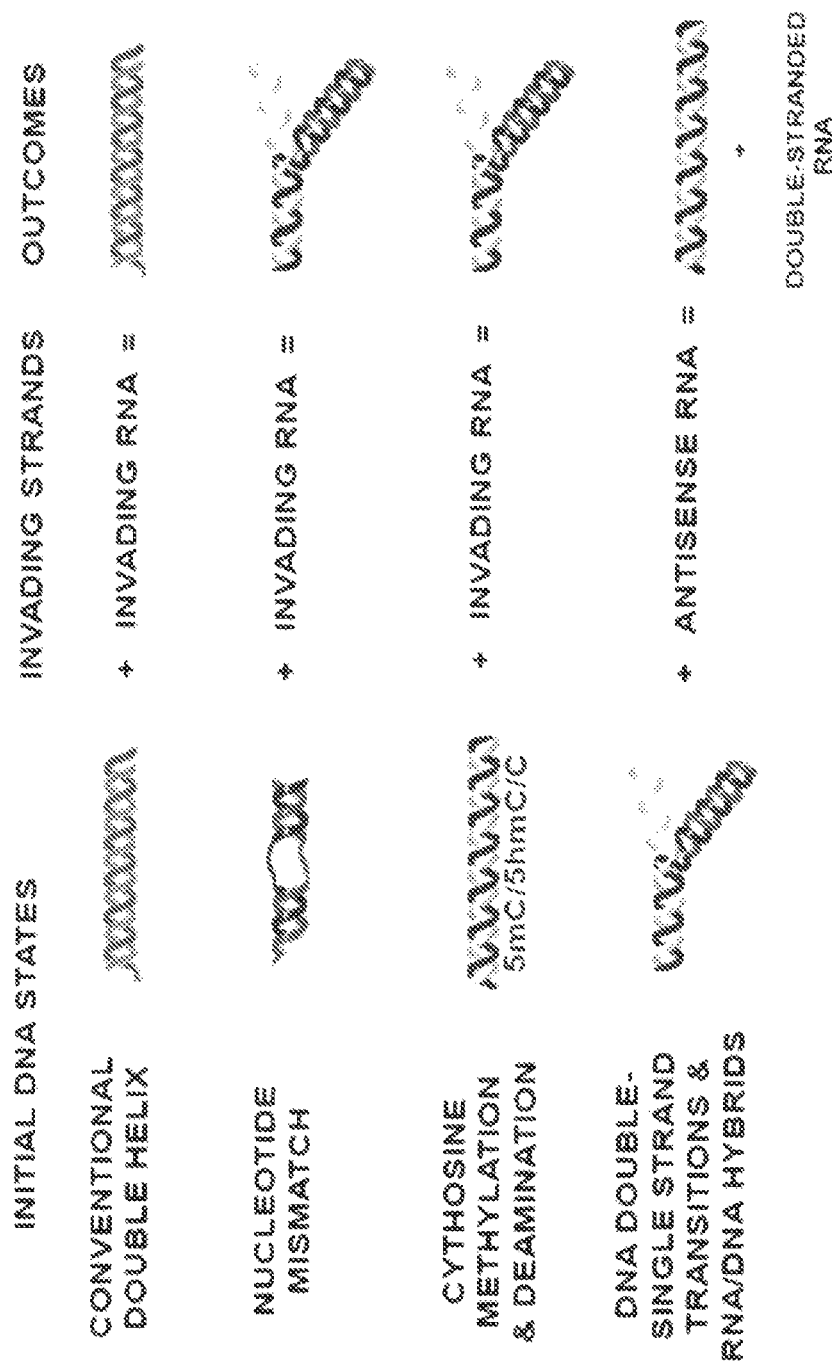

FIGS. 38A and 38B illustrate DNA methylation-associated genome editing mechanisms trigger TET protein dependent and independent cytosine reconstitution pathways facilitating the recovery of the conventional DNA double helix and altering the sensitivity of DNA double helix to invading RNA molecules in accordance with some embodiments described herein.

Figure 39:
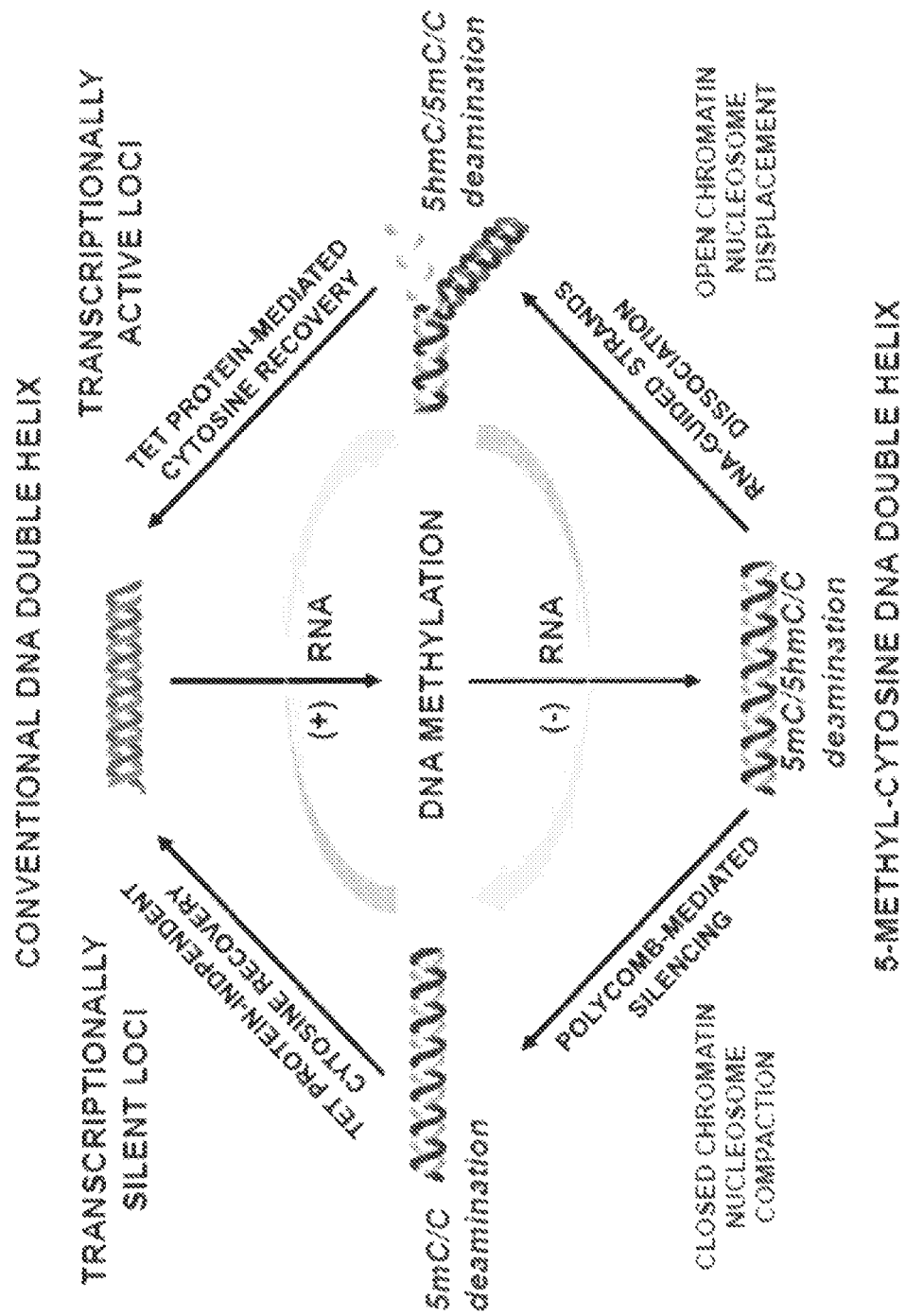

FIG. 39 illustrates a working model of RNA-guided DNA double helix nano-dynamics governing chromatin reprogramming and transitions to distinct regulatory states of chromatin in vivo in accordance with some embodiments described herein.

Figure 40A:
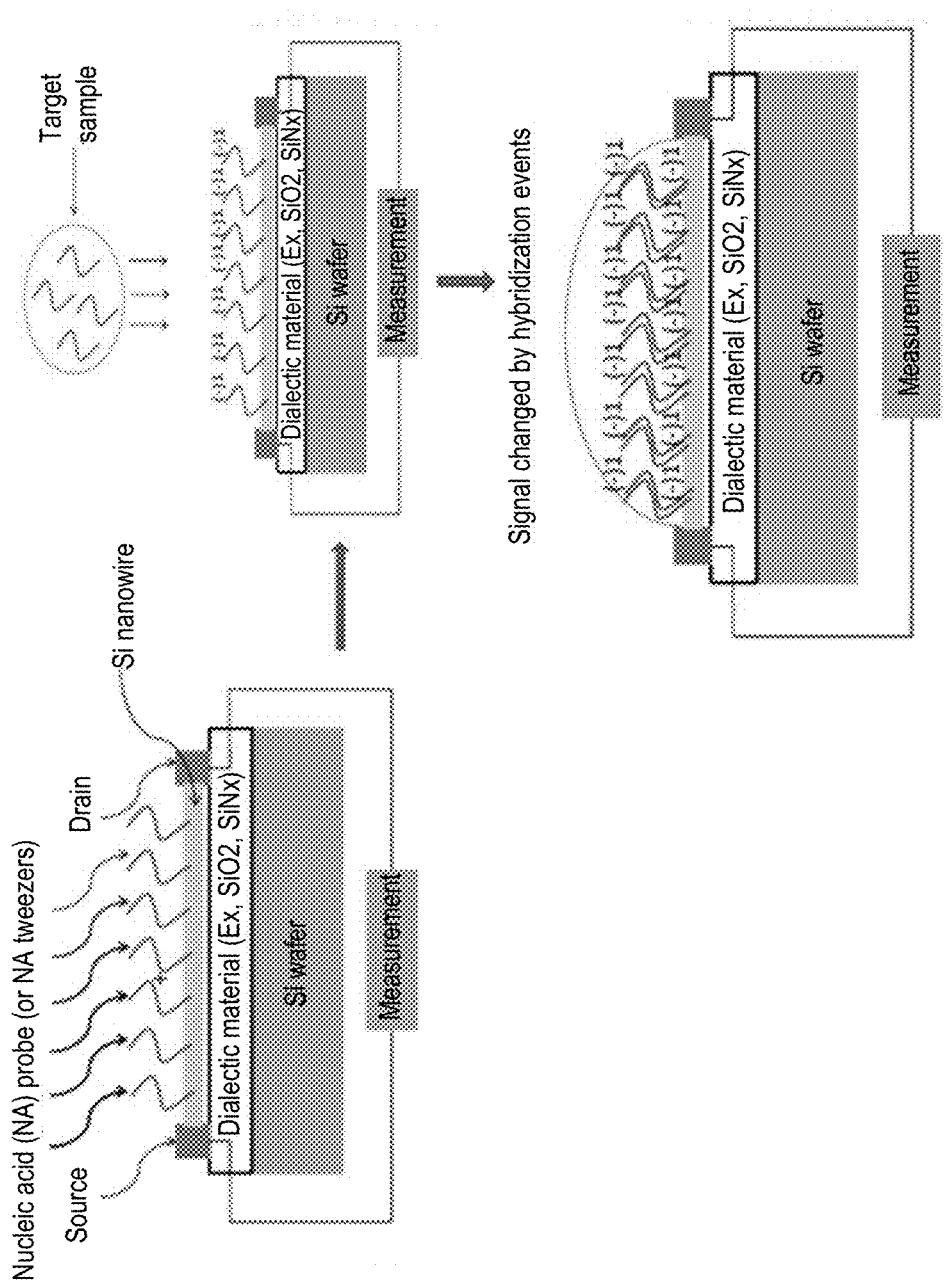
Figure 40B:
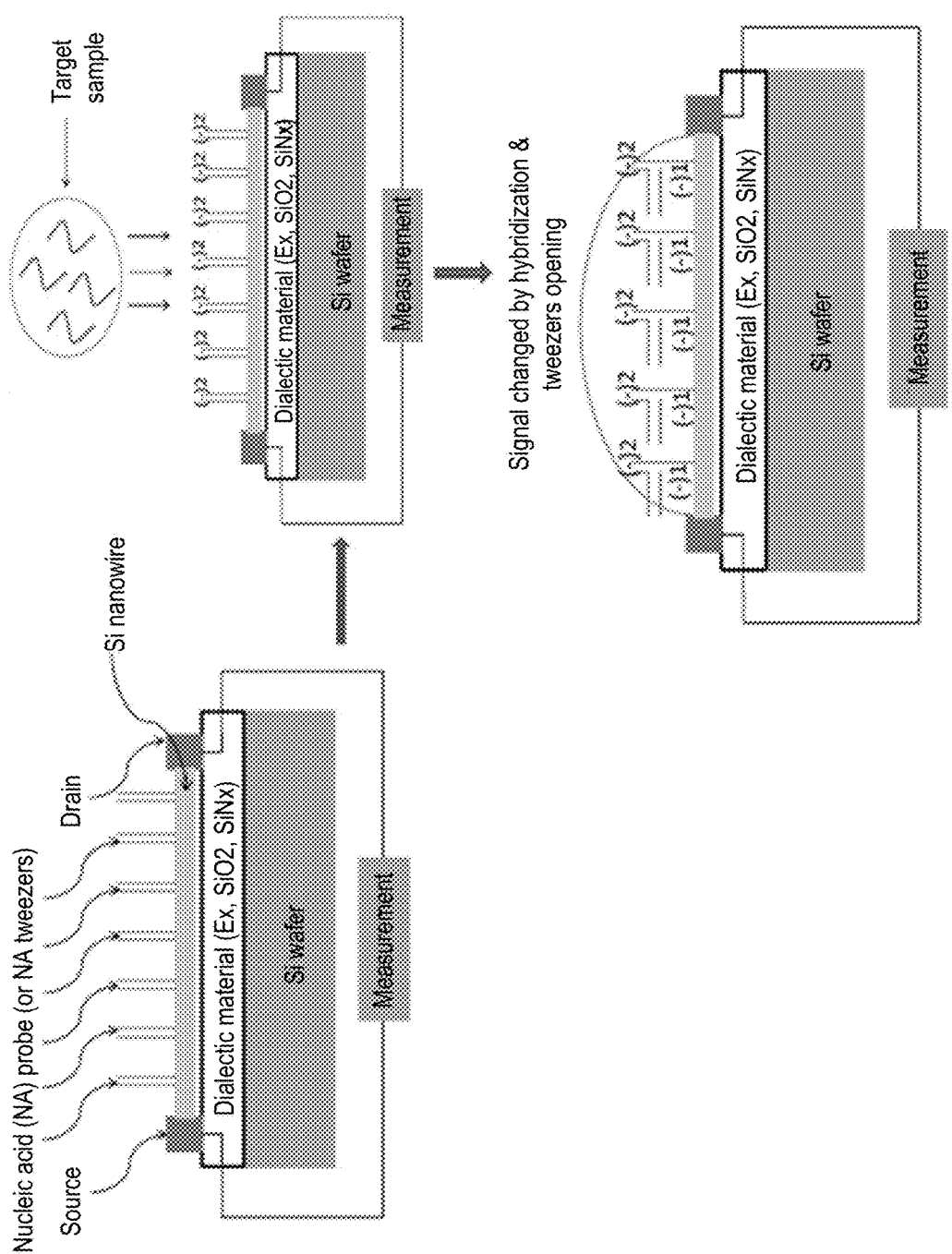

FIGS. 40A and 40B illustrate detection methods of nanosensors' engagement with target molecules based on changes of the electrical charge of nano-devices after the hybridization of nano-sensors with nucleic acid molecules in accordance with some embodiments described herein.

Figure 41:
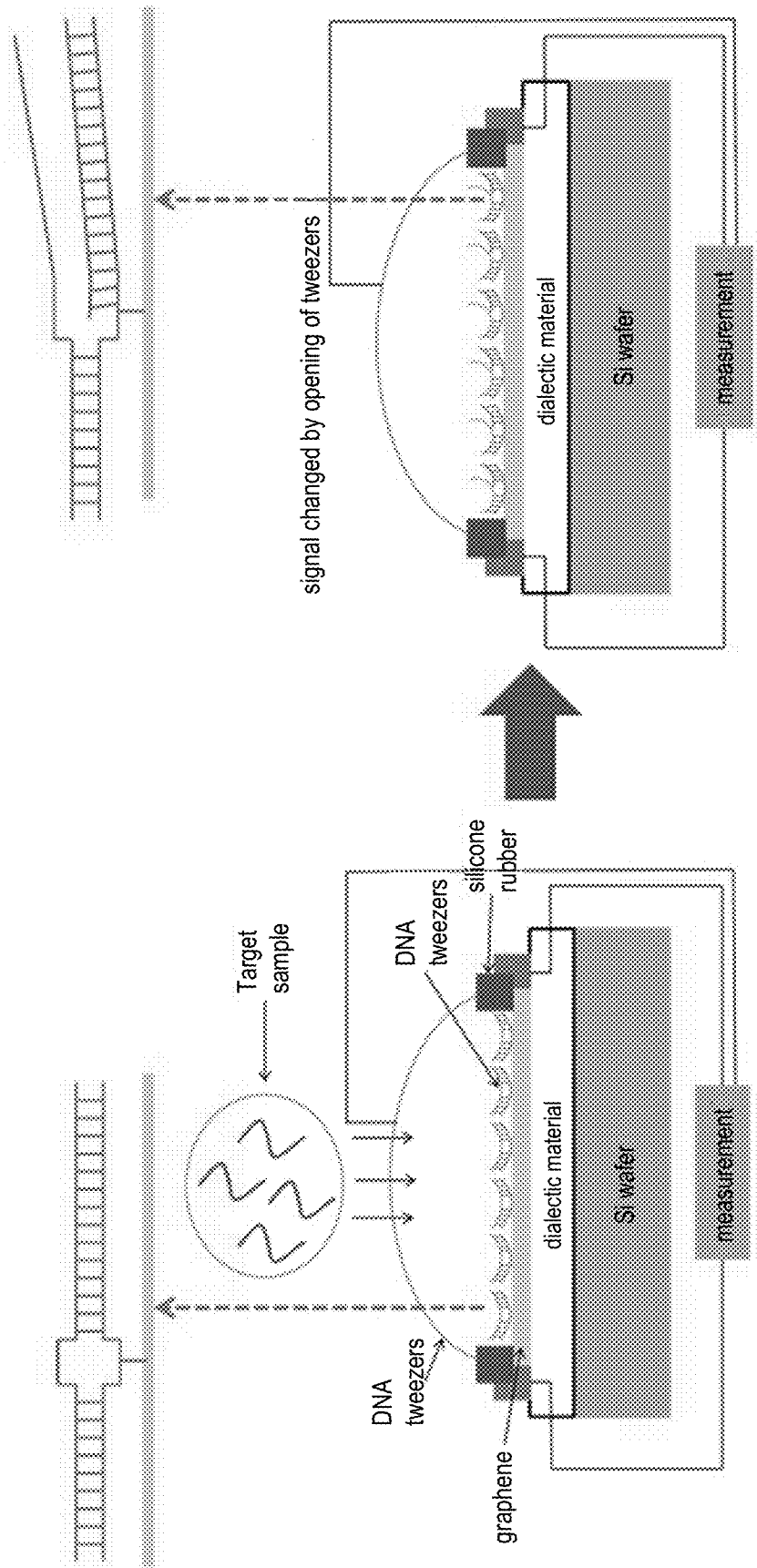

FIG. 41 shows an illustrative diagram of an example nanosensor device of the disclosed technology including an exemplary SNP probe nucleic acid zipper-based tweezers device.

Figure 42A:
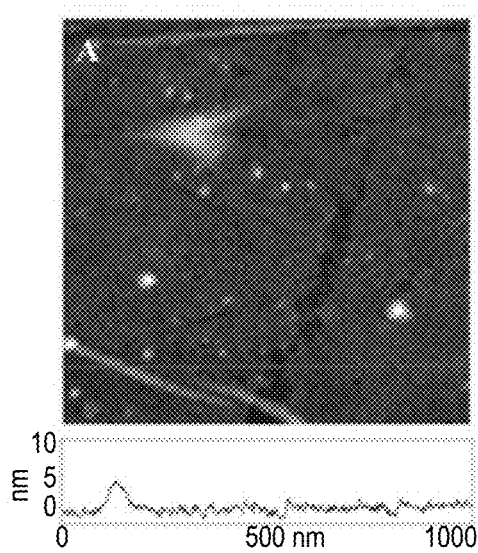
Figure 42B:
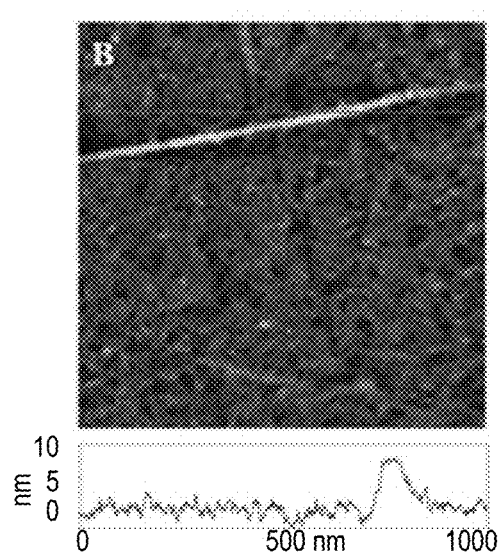
Figure 42C:
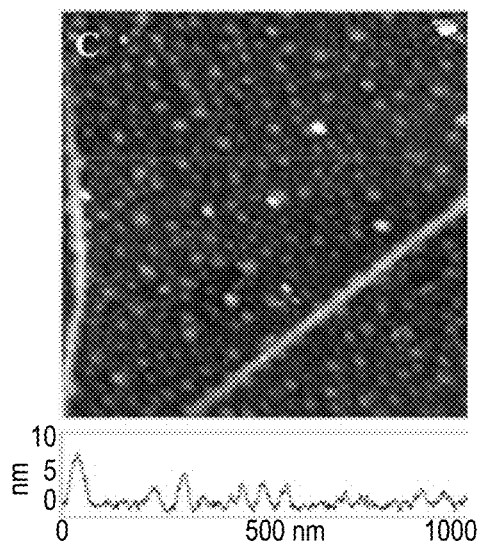
Figure 42D:
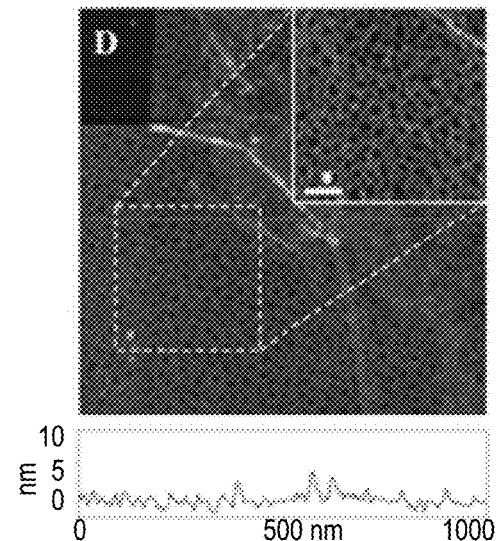
Figure 42:
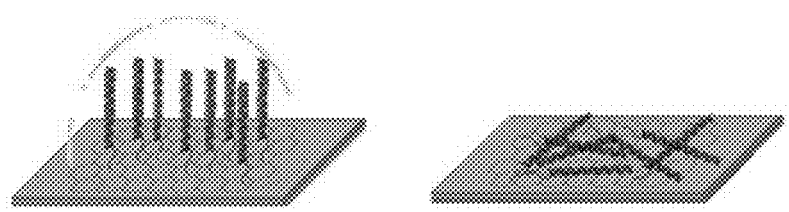

FIG. 42 shows AFM images of graphene transistor surface with and without DNA strands. FIG. 42A shows that graphene surface in fluid is mostly flat with some defects (darker color regions) and graphene wrinkles (light color regions). FIG. 42B shows that PASE coated graphene surface in fluid has a flat surface with similar wrinkle height about 7 nm. FIG. 42C shows that after binding of double strand DNA on the PAGE coated graphene surface in fluid, smooth surface of graphene is covered with dotted structure of DNA strands at height of 2-4 nm while wrinkles remain intact. FIG. 42D shows that DNA strands are visualized better in air AFM image with distinctive DNA structures. Inset image shows more details of DNA structures. Surface height profiles are plotted at the bottom of each image. Cartoons at the bottom represent formation of DNA in liquid and air. All images are 1 μm2 and z range is 20 nm except the z range and the scale bar of the inset is 10 nm and 100 nm, respectively. Concentrations of the T DNAs and standard deviations were based on three sets of data points for each case.

Figure 43A:
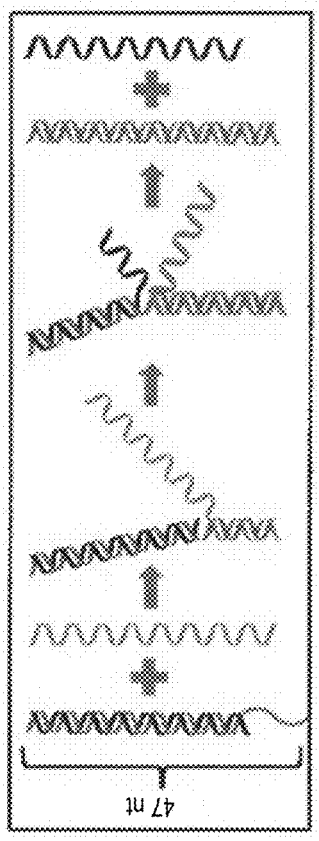
Figure 43B:
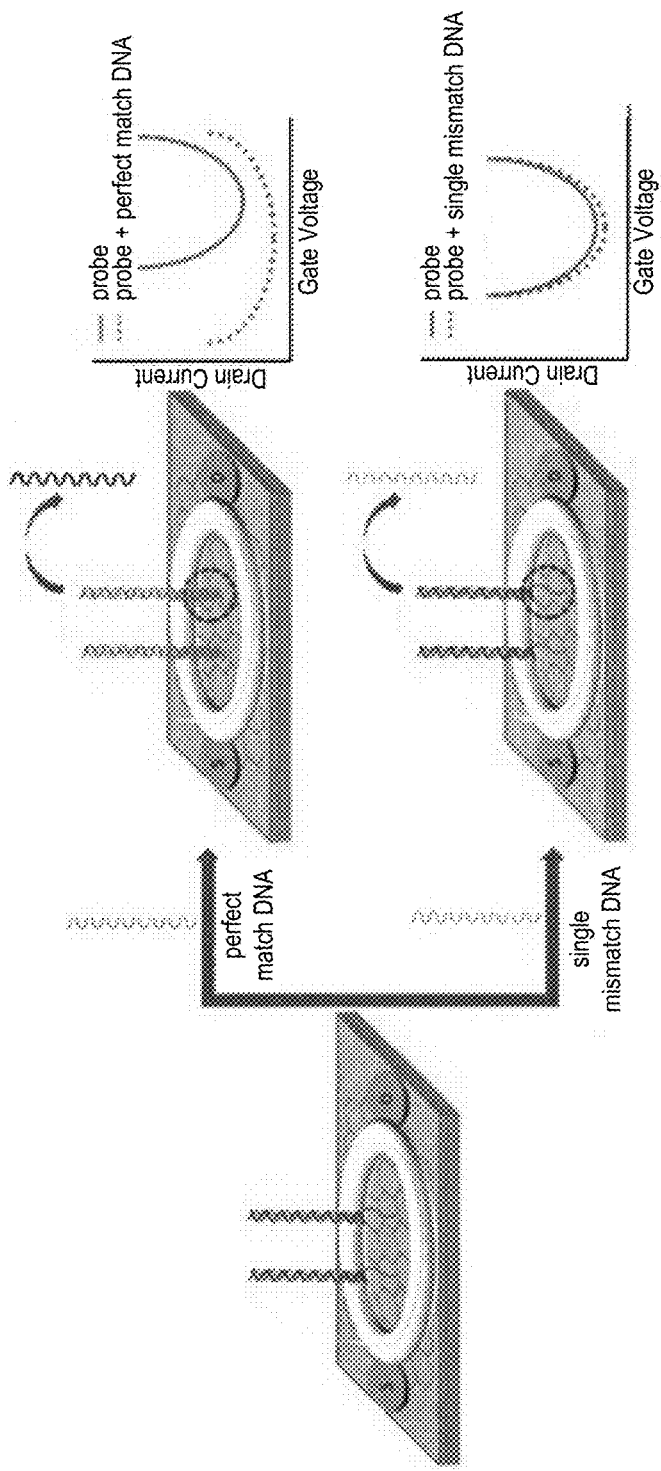

FIG. 43 shows schematic illustration of the sensor. FIG. 43A shows that the normal strand (N) contains 7 nt of toehold, which is single-stranded at the initial state. When a perfect match target (T) strand meets a double stranded probe (DS probe), it displaces the weak strand (W) and toehold part becomes double-stranded. FIG. 43B shows that when the strand displacement happens on the graphene FET sensor, the electrical signal is changed (Top). The green strand displaces the black strand and the black dot circle part becomes double-stranded. The single mismatch T does not operate the strand displacement properly thus the signal changes less (Bottom); the grey strand does not displace the black strand therefore the black dot circle part remains single-stranded. "S" and "D" represent source and drain of FET, respectively.

Figure 44A:
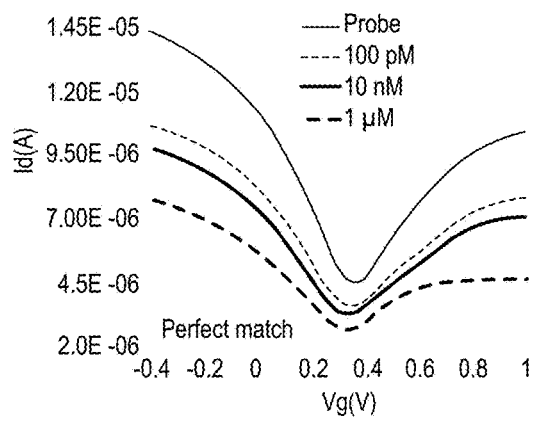
Figure 44B:
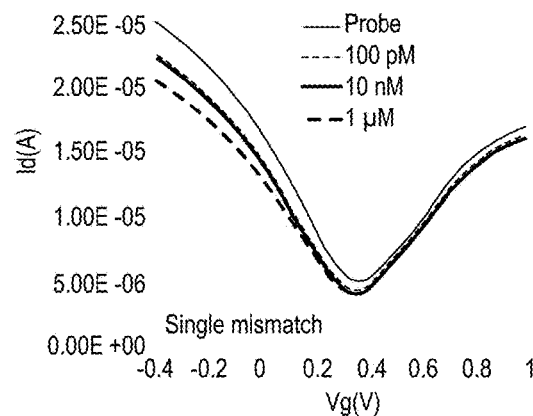
Figure 44C:
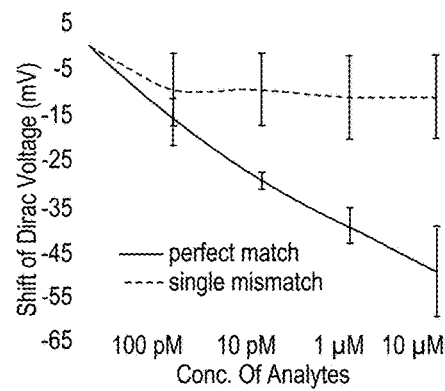

FIG. 44 shows the transfer characteristics of the graphene FET sensor. The perfect match T (FIG. 44A) shifted the I-V curve according to concentrations while the single mismatch T (FIG. 44B) shifts the I-V curve significantly less. The DNA sequences of T used in the experiments are shown over the I-V curve. FIG. 44C shows a statistical summary of Dirac voltage shift of the devices shown in FIGS. 44A and 44B. The Dirac voltage is expressed as a function of the concentration of added target DNAs. Statistical data were based on three sets of data points for each case. FIG. 44 discloses SEQ ID NOS 40 and 41, respectively, in order of appearance.

Figure 45:
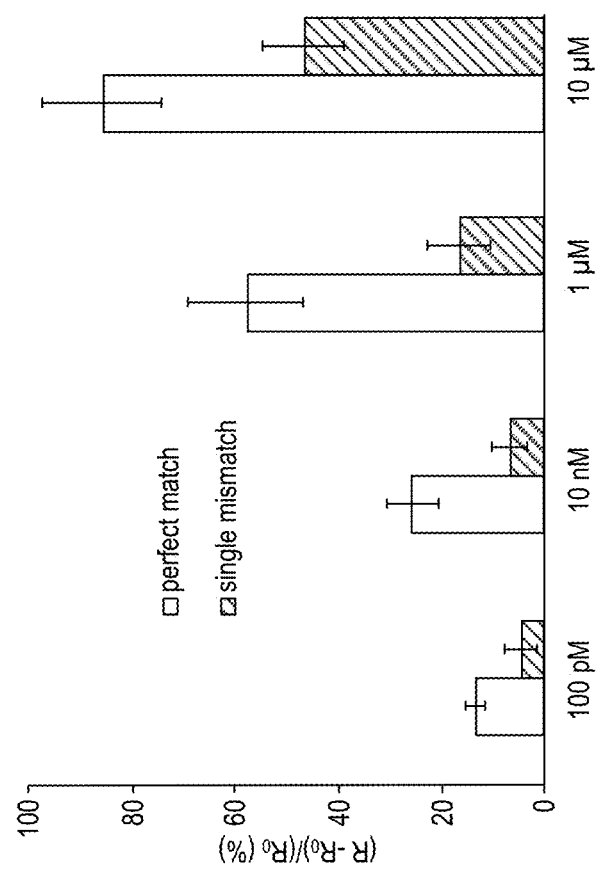

FIG. 45 shows distinguishable resistance change of the channel layer caused by strand displacement at different concentrations of the T DNAs. Average values of measurements and standard deviations were based on three sets of data points for each case.

Figure 46:
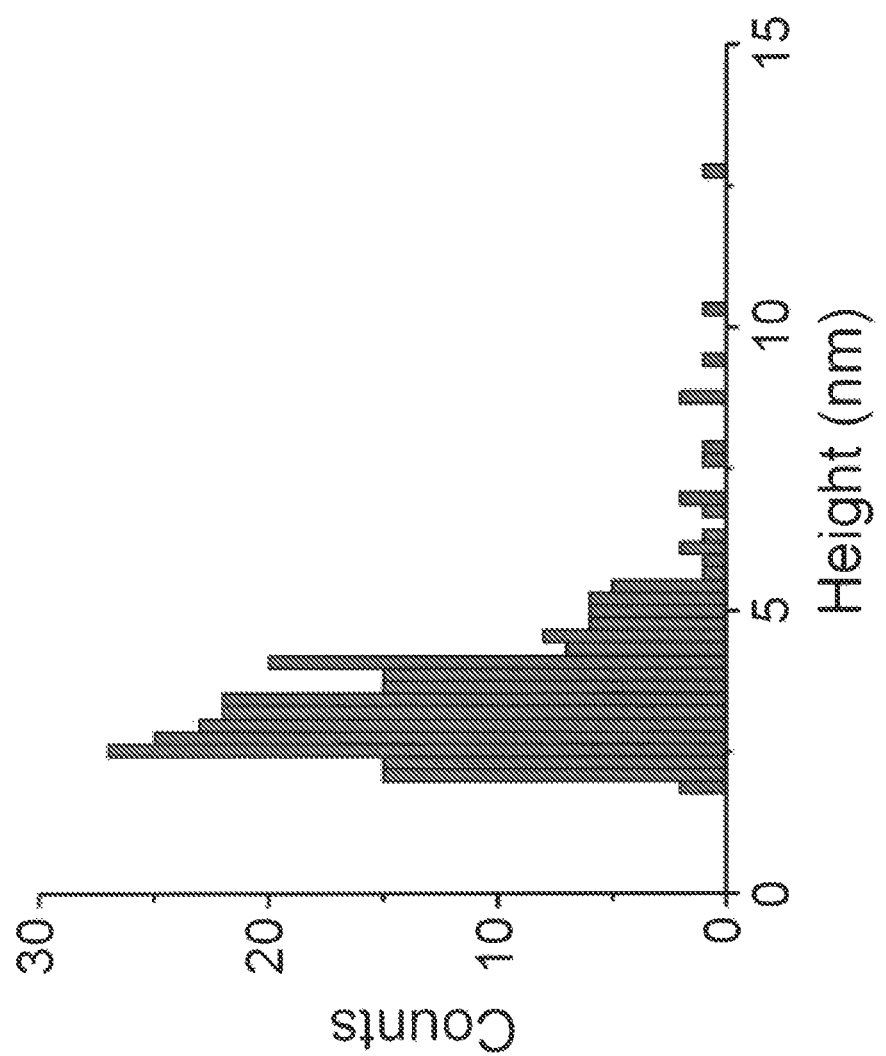

FIG. 46 shows height histograms of dsDNA on graphene substrate in fluid. Heights are mostly distributed from 2 nm to 6 nm and the average height 3.6±1.4 nm (n=254).

Figure 47A:
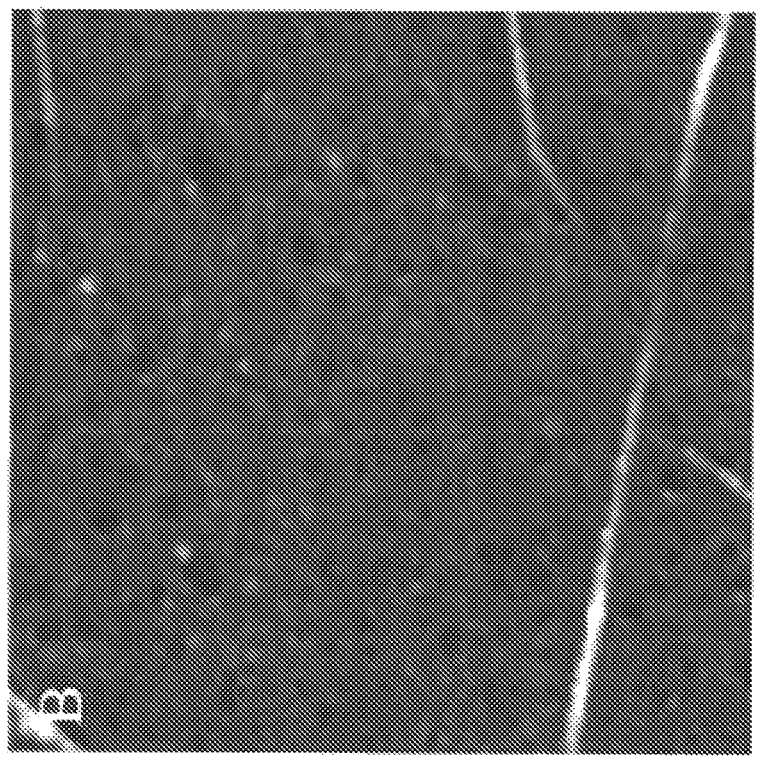
Figure 47B:

FIG. 47 are AFM images of graphene surface (FIG. 47A) and PASE coated graphene surface in air (FIG. 47B). All images are 1 µm2 and z range is 20 nm.

FIG. 48 shows an example I-V curve transfer characterization before and after DS probe functionalization. The curve shifted down and left after the functionalization. X-axis is gate voltage and Y axis is drain current.

Figure 49A:
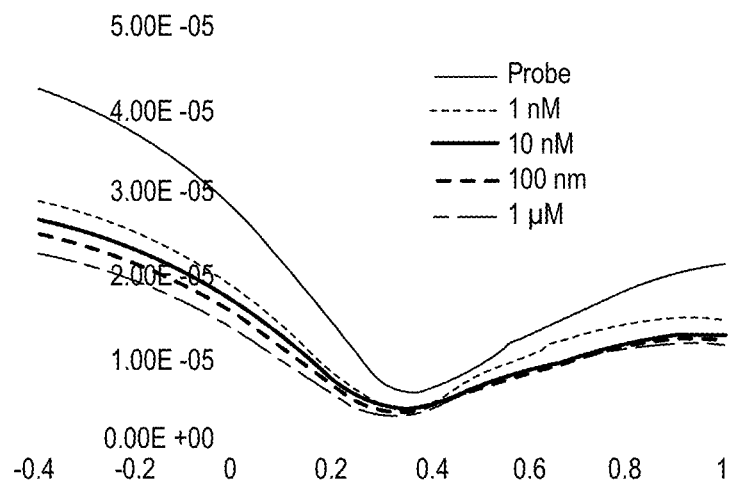
Figure 49B:
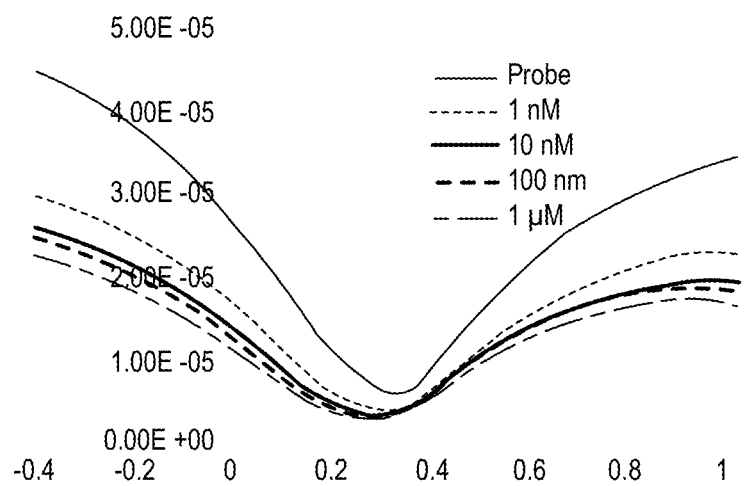

FIG. 49 shows the I-V curve comparison with different buffer solution as liquid gate: 12.5 mM of $MgCl_2$ buffer solution (FIG. 49A) and 1×PBS which contains 137 mM of NaCl and other ions (FIG. 49B). $MgCl_2$ buffer showed clearer shifts of the curve in negative X-axis. X-axis is gate voltage and Y axis is drain current.

Figure 50A:
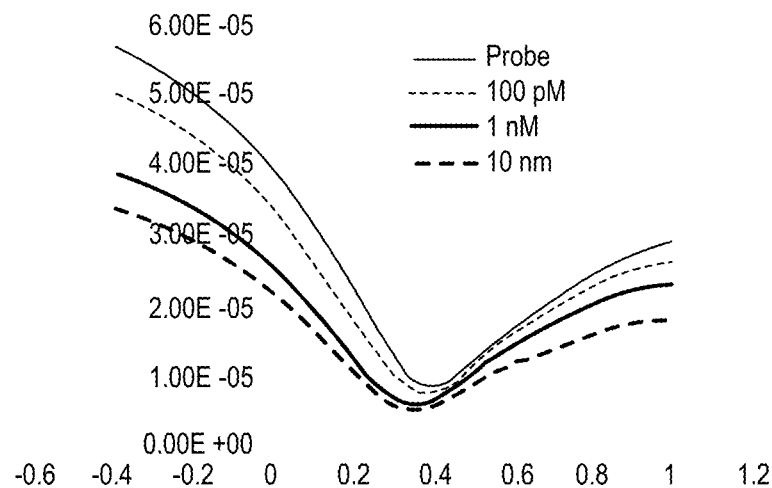
Figure 50B:
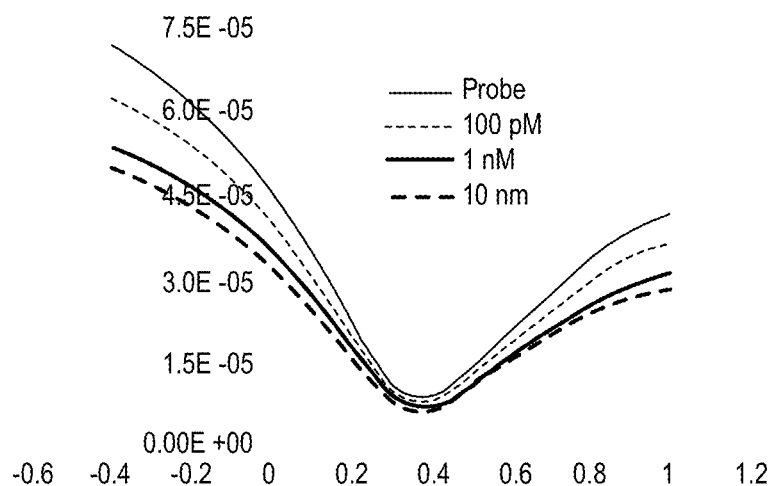

FIG. 50 shows another set of I-V curve with a different dimension of graphene channel. The dimension of the channel was 2 mm×7 mm. FIG. 50A shows the strand displacement with the perfect match T and FIG. 50B with the single mismatch T.

Figure 51:
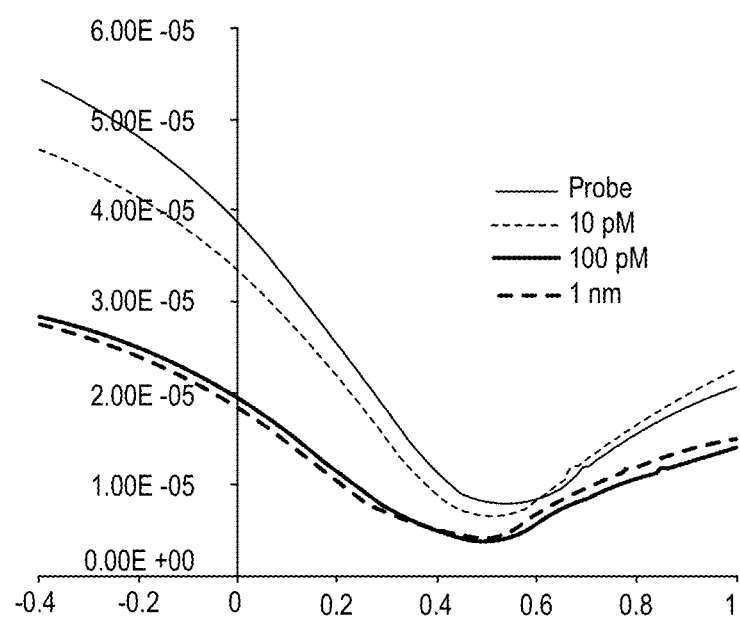

FIG. 51 shows I-V curve transfer characterization with single probe. Only N strand was used as probe strand instead of DS probe. The single mismatch T was used for this test and I-V curve shifted down and left as much as complementary T with DS probe.

Figure 52:
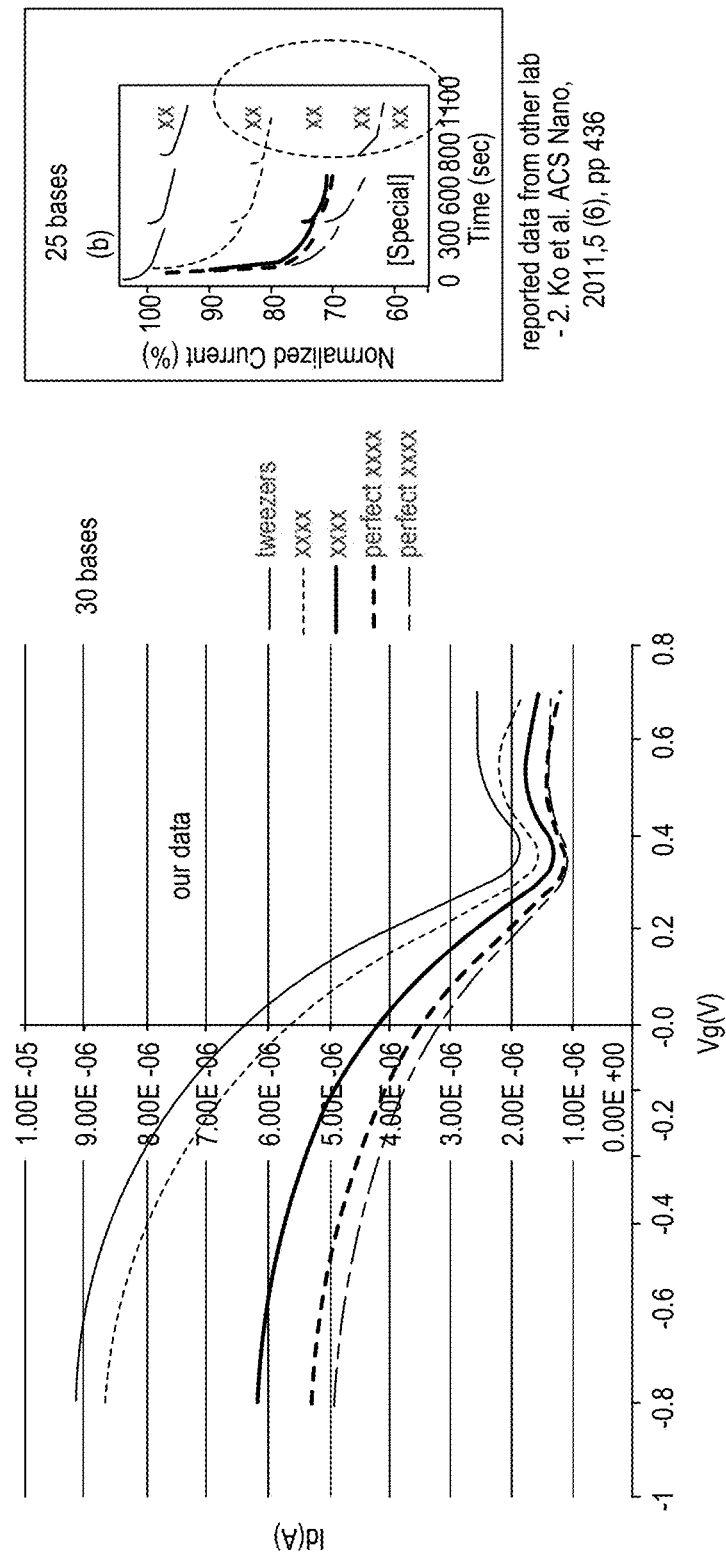

FIG. 52 shows a data plot demonstrating example SNP measurements using an exemplary nanosensor device of the disclosed technology.

Figure 53:
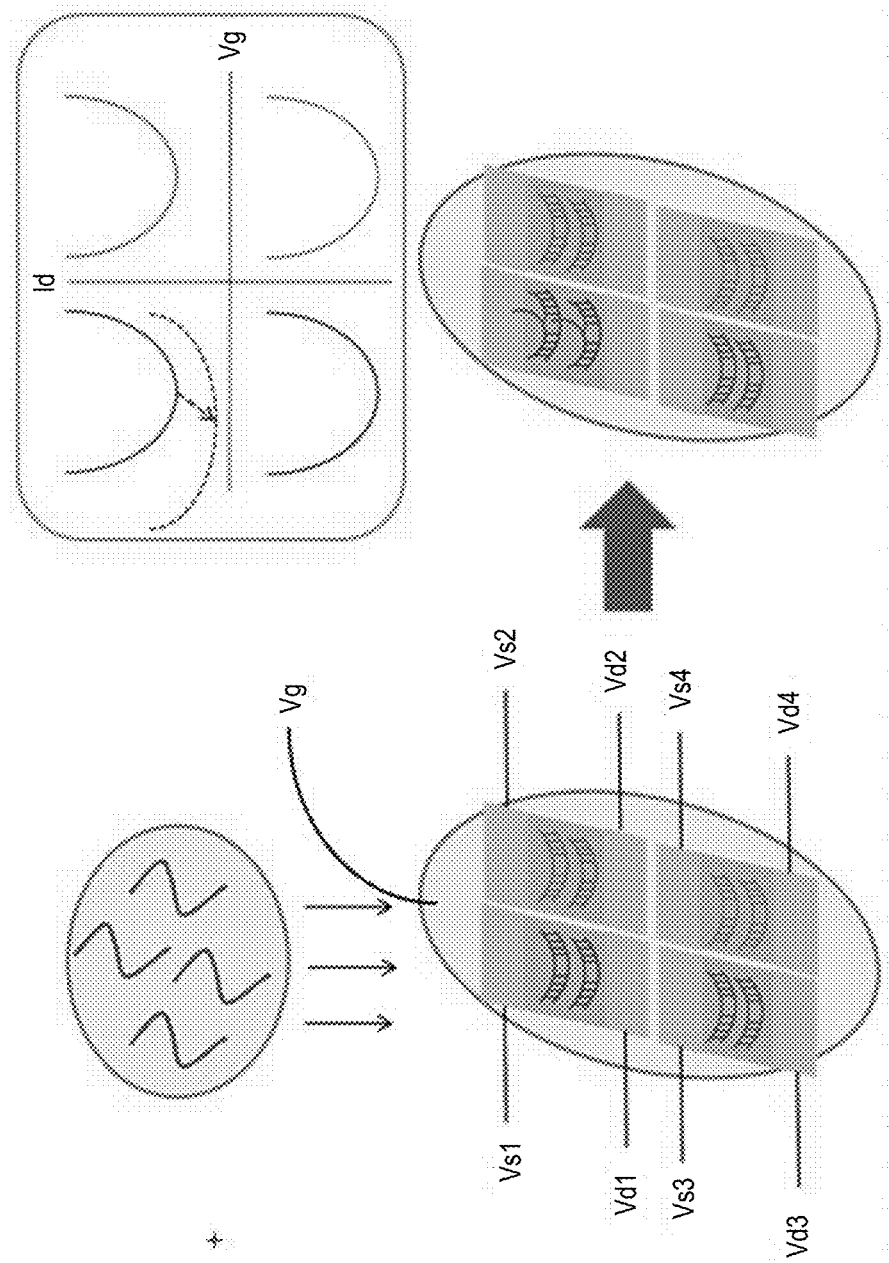

FIG. 53 shows an illustrative diagram of an exemplary nanosensor device of the disclosed technology configured in a microarray format.

FIG. 54A shows an example of graphene FET sensor with DNA tweezers probe. "S" and "D" represent source and drain, respectively, of FET. Gate voltage is applied directly on the liquid gate; the liquid gate is shown as a hemisphere surrounding the DNA tweezers probe. FIG. 54B, left panel shows strand displacement, and part of the loop portion becomes double-stranded (black dotted circle region). W strand is bound by hinge part, thus the tweezers become a triple-stranded complex. As three DNA parts are dangling, the occupied loop part is located close to the surface. FIG. 54B, right panel shows that target strand with single mismatch does not allow the strand displacement properly. Thus, the toehold region remains single-stranded (black dotted circle). The I-V relationship (I-V curve) attributable to charge difference during the strand displacement in the gene chip FET sensor. The I-V curve for strand displacement with perfect match is on the left, and the I-V curve shifts leftward and downward. The single-mismatch target strand does not displace the strand properly; thus, the I-V curve shown on the right remains almost the same.

Figure 55A:
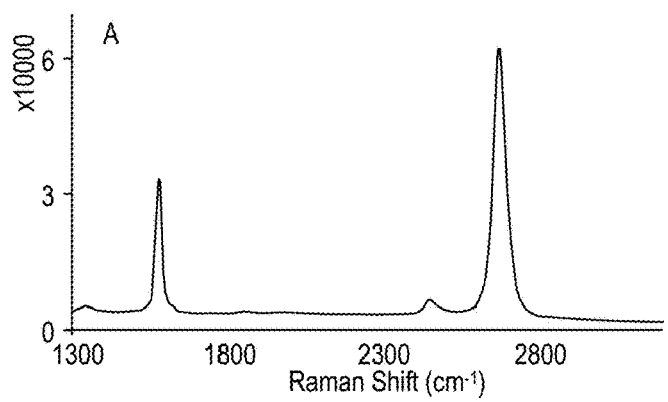
Figure 55B:
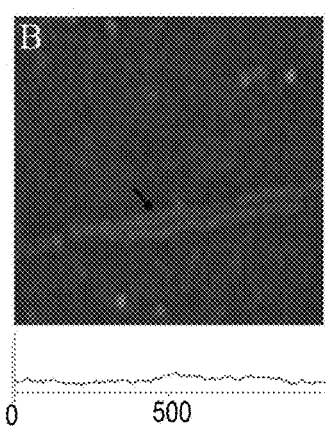
Figure 55C:
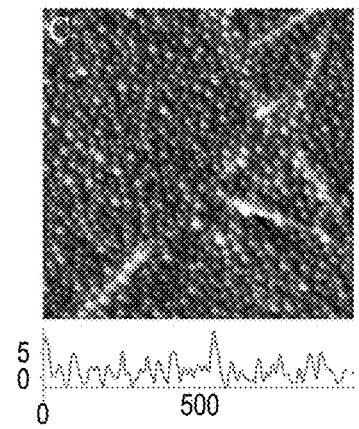
Figure 55D:
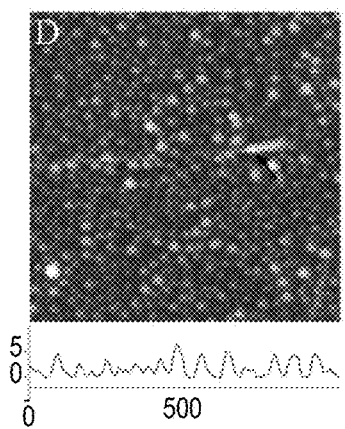
Figure 55E:
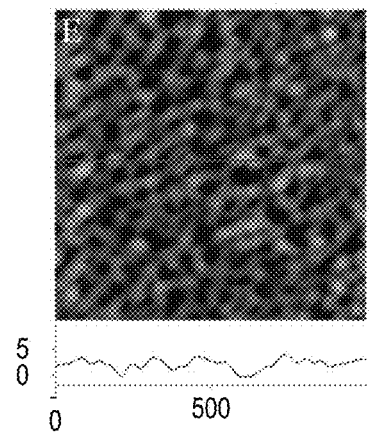
Figure 55:
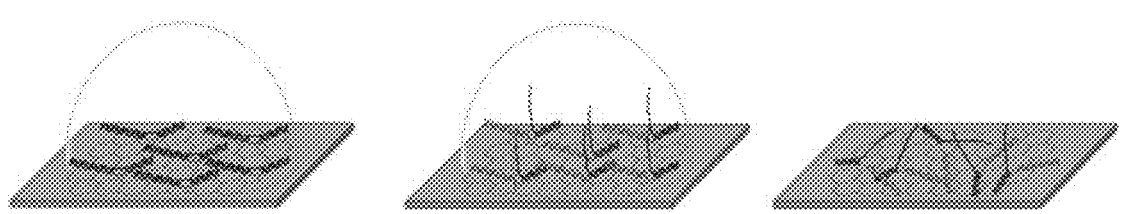

FIG. 55 shows the Raman spectrum of the graphene and AFM images of graphene transistor surface with and without the DNA sensor. FIG. 55A shows the Raman spectrum of the CVD graphene, indicating that the transferred graphene was a single layer. FIG. 55B shows that the graphene surface in fluid is mostly flat with some wrinkles. FIG. 55C shows the graphene surface covered with DNA tweezers in fluid, strands produce features of ~2-8 nm in height with an average diameter of about 18 nm. FIG. 55D shows that after binding of a perfect match DNA strand in fluid the features decrease slightly in height to about ~2-6 nm and increase in diameter to about 22 nm. FIG. 55E shows AFM images of graphene transistor surface with the DNA sensor in air. When not surrounded by fluid medium, the DNA tweezers linked to graphene lie down on the surface in random polygonal patterns. Black arrows indicate graphene wrinkles. Cartoons at the bottom represent models of formation of DNA structure in liquid and air. All images have a scan area of 1×1 µm and a z range of 19 nm. All the units in the surface height profiles are nm.

Figure 56:
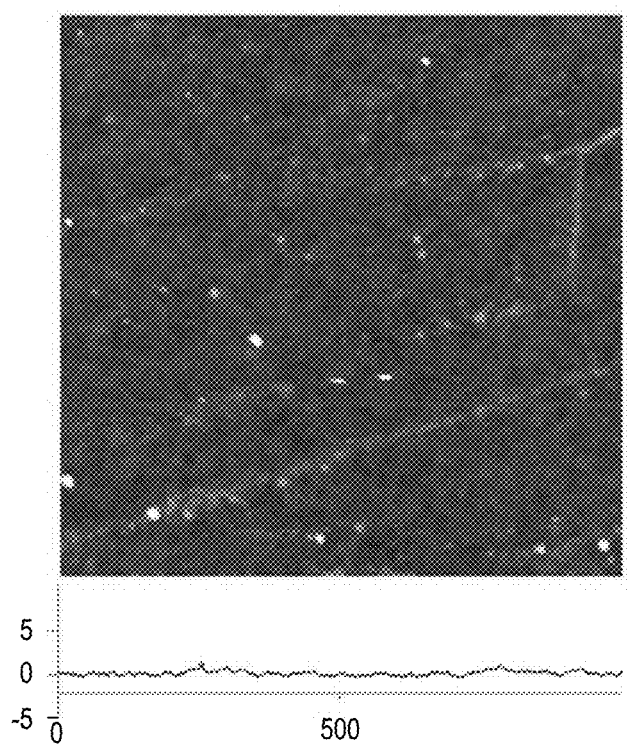

FIG. 56 shows an AFM image of graphene transistor surface with and without the DNA sensor in air. The graphene surface is mostly flat with some wrinkles. Surface height profiles at the line are plotted at the bottom of image. Unit is in nm.

FIG. 57 shows the I-V relationship of the graphene FET sensor for the strand displacement reactions. FIG. 57A shows that the perfect-match T shifted the I-V curve according to the indicated concentrations. FIG. 57B shows that the single-mismatch T shifts the I-V curve significantly less. The DNA sequences of T used in the experiments are shown over the I-V curve. FIG. 57C shows the Dirac voltage shift of the FET sensor. The Dirac voltage is expressed as a function of the concentration of the added target DNAs. FIG. 57D shows distinguishable resistance changes of the channel layer caused by strand displacement at different concentrations of the T DNAs. FIG. 57 discloses SEQ ID NOS 42 and 48, respectively, in order of appearance.

Figure 58:
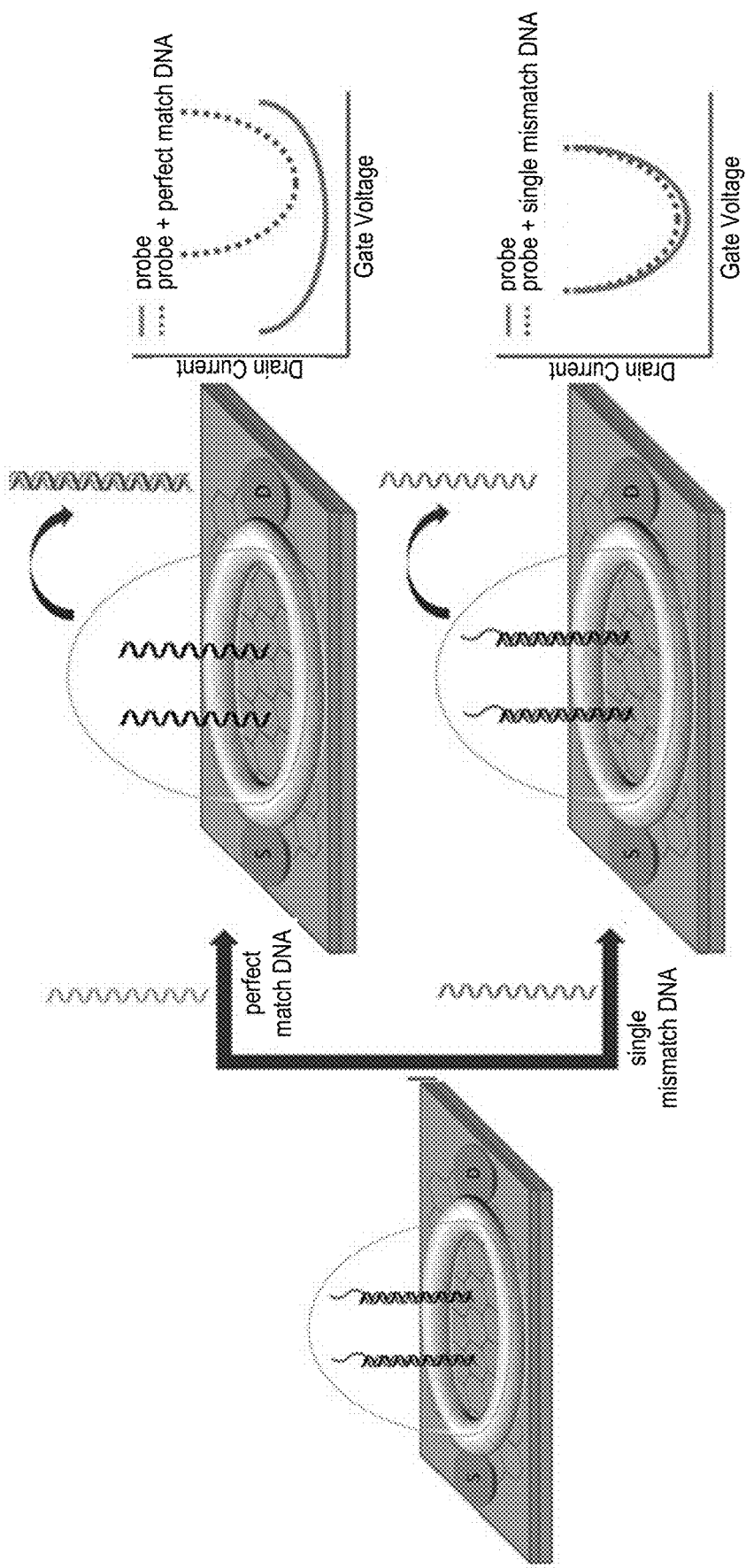

FIG. 58 illustrates an example of the probe design on the graphene chip.

DETAILED DESCRIPTION

Certain single nucleotide polymorphism (SNP) analyses are available and some suffer technical limitations. For example, some enzyme-based methods require high costs and long term process, which deter assessment of the general public. More affordable hybridization based methods are often challenged by reliability problems. Hybridization-based methods for SNP detection have several disadvantages, including cross-hybridization between allele-specific probes. The average length of the probe on microarray varies considerably; the probe and target strand sequences, except a single mismatch, are complementary to each other. A single mismatch may often fail to reduce the affinity between probe and SNP target strands. This limits the detection of single mismatch in longer probe-target strand hybridization as the longer probes would have more frequent cross hybridization. For example, single mismatch in the center of 15 base pairs (bps) of probe-target hybridization can be detected as there is critical difference in hybridization affinity between a perfect-matched and a single-mismatched hybridization. However, when the probe length is 40 or 50 nucleotides (nt), a single mismatch produce relatively small difference between a perfect-matched and a single-mismatched hybridization. Thus its detection is difficult with the simple hybridization-based methods. The general length of probe used in microarray is more than 20 nt, thus cross hybridization significantly reduces its reliability and specificity. Moreover, detection of a single mismatch in a longer probe is important because fewer probes are needed to obtain the same level of reliable analysis with longer probes (60-80 nt) and they provide more sensitive detection. Moreover, it is still constrained by large and expensive equipment to analyze the data.

Thus, the detection and sequencing of nucleic acids for diagnostics, forensics and environmental monitoring are of great interest in personalized precision medicine. Some detection methods based on fluorescent labeling require laboratory scale settings such as fluorimeters or laser scanners to analyze optical signals and thus may not be suitable for in-field or at home diagnostic applications. Therefore, it is desirable to develop devices and methods for in-field or at-home detection of specific nucleic acid sequences of small quantities.

Disclosed herein are nano-sensors and techniques for their design, engineering, and use for detection and discrimination of nucleic acids with a high resolution, sensitivity or specificity. In some implementations, disclosed nano-sensors have achieved ~200,000-fold enhancement of sensitivity for detection of nucleic acid molecules compared to current nano-devices. Applications include tools for biological and biomedical research and diagnostic, prognostic, and therapeutic applications for personalized chemoprevention and disease management (e.g., for cancers, cardiovascular and neurodegenerative disorders, diabetes, neurological and developmental disorders). The disclosed technology is ready for the immediate implementation in vitro.

This disclosure provides for devices and methods of using nucleic acid probes, particularly double-stranded probes such as DNA zippers or DNA tweezers, to detect mismatches between the probe and a target strand. The strand displacement-based technology disclosed herein can be used to detect a single nucleotide mismatch and is less restricted by the length of the nucleic acids, as compared to the prior-art technology. In some embodiments, the conversion of a chemical cue into a substantial mechanical strand displacement is detected by time-lapse fluorescence measurements. In other embodiments, the mismatch between the probe and the target is detected and measured by electrical sensing devices.

Electrical detection of nucleotide can lower the spatial and budget constraints and using double-stranded probe can solve the reliability problem dramatically. Electrical biomolecular sensors have been developed majorly being focused on enhancing sensitivity of transducers with variety of modification or introduction of new platforms. More effective utilization of DNA nanotechnology can provide different insights and approaches to accelerate evolution of biosensors and bioelectronics.

Electrical sensing-based methods can successfully lower the limit of sequence specific nucleic acid detection to the femto molar level. A field effect transistor (FET) can be employed as a highly sensitive sensor and can potentially be integrated with other on-chip analytical systems. Disclosed herein are devices and methods for miniaturized chip-based electrical detection of nucleic acid, enabling in-field or at-home detection of specific nucleic acid sequences.

Graphene is an attractive electronic material of choice for a biosensing platform because it has high sensitivity to the changes in carrier mobility with respect to changes in the gating electric field, low intrinsic electrical noise, mechanical strength and flexibility. DNA strand displacement based-probe on graphene FET can detect single nucleotide polymorphism (SNP) in relatively long nucleic acid sequences with unprecedented specificity. SNPs are markers for a variety of diseases, including various forms of cancer, genetic disorders, and are of critical importance for successful practical implementation of the concept of personalized medicine. Thus, detection of SNP mutations with high specificity and sensitivity is essential for a broad range of diagnostic applications and effective implementations of personalized precision medicine approaches. The feasibility of the approach demonstrates that a more complex design of the probe mechanism can be used to achieve better functionalities and facilitate nano-scale engineering of electrical biosensors.

Another advantage of using an electrical signal-based sensor is its compact size and portability compared to current fluorescence-based techniques. Also, a fully electronic sensor and signal measurement system can communicate using wireless signal transmission which enables signal processing on a portable computing device such as a smart phone. Wireless transmission of the electrical signals obtained by the biosensors further facilitates unsophisticated end-users to access nucleic acid detection chip technology.

In some embodiments, this disclosure is directed to designs and technology for sensing specific nucleic acid molecules for the diagnosis of abnormal pathology and diseases such as cancer, genetic disease, or for preparing personalized medicine in both human and non-human animals. The disclosed technology can be used to implement methods for: (i) combining a graphene field effect transistor (FET) and a nucleic acid actuator as a nucleic acid molecular sensor with high specificity; (ii) fabricating graphene FET, consisted of a graphene channel, two electrodes and a solution reservoir, can be operated with the liquid gate method; (iii) designing a nucleic acid actuator such as a DNA zipper with two partially complementary strands of DNA, toeholds and inosine bases, based on strand displacement technique, to be sensitized to a specific nucleic acid sequence; (iv) functionalizing DNA zipper on graphene channel in the FET with 1-Pyrenebutanoic acid succinimidyl ester (PASE) and amine-amide bonding; and (v) measuring the current change by operation of DNA zipper in the FET sensor to detect single nucleotide polymorphism (SNP). Other implementations are also disclosed in this patent document.

Nucleic Acid Probes

The disclosed technology can be implemented based on architectural principles and use DNA strand displacement reactions and biologically relevant mechanisms of DNA strand dissociation and re-association to design analytical nano-devices uses. The regulatory mechanisms affecting DNA dynamics in vivo involve protein-less structural-functional determinants, in particular, interactions of DNA strands with invading DNA or RNA molecules. The nano-sensors design techniques utilize conversion of a chemical cue into a substantial mechanical strand displacement detected by time-lapse fluorescence measurements, measurements of electro-signal changes, or other methods.

Although DNA molecules are used as examples to illustrate the technology and devices disclosed herein, one skilled in the art would understand that the same principle and design concept can be applied to other types of nucleic acids, including naturally occurring nucleic acids and artificial nucleic acids. Thus, it is within the purview of one skilled in the art to make and use a nucleic acid probe based on the disclosure provided herewith.

Dynamic transitions between double-stranded and single-stranded states are intrinsic components of DNA double helix molecular lifecycle during replication, transcription, DNA repair, and reciprocal conformational changes between right-handed B-DNA and high-energy left-handed Z-DNA forms. Structural and molecular determinants governing DNA double helix dynamics and their precise role during execution of these fundamental biological processes remains poorly understood. Protein-less DNA sequences are extensively utilized in nano-engineering to build controlled devices which operate using on-demand transitions between single-stranded and double-stranded states of DNA molecules.

Various nucleic acid nano-devices, including DNA and RNA nano-devices are disclosed herein for analysis of kinetics of strand displacement reactions and studies of mechanisms of strands' dissociation and re-association to identify structural-functional determinants of DNA double helix nano-dynamics during transitions between double-stranded and single-stranded states. Changes of the conventional double helix introduced by cytosine methylation/deamination reactions and base pairing mismatches significantly influence the kinetics of strand displacement and transition to a single-stranded state induced by invading RNA and DNA molecules. Markedly enhanced kinetics of RNA/RNA interactions facilitate eviction of invading strands and rapid transition to a double-stranded state. Using biological models as a guide for the rational design of RNA sensing nano-devices, ~200,000-fold enhancement of nano-device's sensitivity for detection of RNA molecules was achieved. One of regulatory functions of pervasive genome-wide transcription is to enable transition cycles between the double- and single-stranded states of DNA molecules. Non-coding RNA-mediated stochastic effects on DNA double helix dynamics may influence nucleosome formation and placement to extend the accessibility time for DNA binding proteins, thereby increasing a likelihood of the assembly and functions on a DNA scaffold of replication, transcription, DNA repair, and chromatin remodeling complexes.

The concept of genome-wide pervasive transcription in human cells is based on experimental evidence that nearly 90% of human genome is actively transcribed. Transcriptome complexity in human cells generated by RNA polymerase (Pol) II activity extends beyond the conventional coding genomic loci defined as genes and transcripts containing open reading frames. It expands to thousands long non-coding RNAs (lncRNAs) and myriads short RNA populations, including miRNAs, siRNAs, piwiRNAs, enhancer RNAs (eRNAs), transcription start site (TSS)-RNAs, trans-regulatory RNAs (transRNAs), and small non-coding snpRNAs containing disease-linked SNP markers. The presence of short bidirectional transcripts appears to be a hallmark of active promoters in mammals and pervasive transcription of eukaryotic genomes is associated to a large extent with bidirectional promoters that synthesize mRNA and divergent populations of non-coding RNAs. In human cells, bidirectional transcription generates non-coding RNAs that induce both target gene activation and suppression, in part, by regulating epigenetic states of targeted genomic loci. Thus, there is an unmet need in fundamental and translational biomedical sciences for reliable new methods of nucleic acid detection and discrimination, which would enable a real-time monitoring of the regulatory effects of bidirectional transcription at specific genomic loci in individual cells with a single-nucleotide level analytical precision.

DNA strand displacement reactions, in which one strand of DNA displaces another in binding to a third strand with partial complementarity to both, are extensively utilized in nano-engineering. Toehold driven strand displacement reactions in which a short single-stranded overhang region (known as a toehold) initiates the strand displacement have been used to create functional DNA devices, including walkers, actuators, and contractile machines. Many DNA devices have forward and reverse reaction cycles with different kinetic rates. The ability to predict toehold driven reaction kinetics when just the domain sequences are known has been difficult but such knowledge is highly desired for DNA nano-engineering. Toeholds is composed of complementary domains that allow an invading strand to bind to a short, single-stranded overhang on one of the DNA strands in a duplex. The invading strand proceeds to displace the incumbent strand (i.e., normal strand without a toehold) in a process called branch migration (BM). BM is iso-energetic and has been described as a simple random walk. The association rate of the toehold is not expected to be heavily dependent on the sequence. A modified strand displacement method with artificial base pairings has been reported recently, using deoxyinosine instead of deoxyguanine, which hybridizes with deoxycytosine, but with less energy than deoxyguanine. It has been suggested that these nano-engineering approaches might be useful for development of the next-generation personalized nanomedicine based on target-specific RNA-guided nano-sensors and nano-devices for diagnostic and therapeutic applications.

Some examples of domain sequences are listed in Table 1 below.

TABLE 1

Examples of Domain Sequences

| Domain | Sequence | SEQ ID NO: |
|---|---|---|
| g | 5'-ACCTA CTCAA CCATA CATCA CTCTA CCTCA aacac tcgaa TCTCC CAAAT ACTAA GCTGT TCAAC TCACC-3' | 1 |
| g" | 5'-C CTCCA GTTCC AAGTA CCACC ATCAC ACCTA CTCAA CCATA CATCA CTCTA CCTCA aacac tcgaa TCTCC CAAAT ACTAA GCTGT TCAAC TCACC-3' | 2 |
| j | 5'-TTCTG GGGAG TGGGA GATGT TGGCT AGATT TACGG TATAA TGAGG TAGAG TGATG TATGG TTGAG TAGGT-3' | 3 |
| j' | 5'-TTCTG GGGAG TGGGA GATGT TGGCT AGATT TACGG TATAA TIAII TAIAI TIATI TATII TTIAI TAIIT-3' | 4 |
| j" | 5'-TTCTG GGGAG TGGGA GATGT TGGCT AGATT TACGG TATAA TIAII TAIAI TIATI TATII TTIAI TAIIT GTGAT GGTGG TACTT GGAAC TGGAG G-3' | 5 |
| $a_1$ | 5'-GGTGA GTTGA ACAGC TTAGT ATTTG GGAGa/IbRQ/-3' | 6 |
| $a_2$ | 5'-/TEX 615/ aTACC GTAAA TCTAG CCAAC ATCTC CCACT CCCCA GAA-3' | 7 |
| $f_{(10,30)}$ | 5'-TTCGAGTGTT TGAGG TAGAG TGATG TAT GG TTGAG TAGGT-3' | 8 |
| $f_{(8,30)}$ | 5'-CGAGTGTT TGAGG TAGAG TGATG TAT GG TTGAG TAGGT-3' | 9 |

TABLE 1-continued

Examples of Domain Sequences

| Domain | Sequence | SEQ ID NO: |
|---|---|---|
| $f_{(7,30)}$ | 5'-GAGTGTT TGAGG TAGAG TGATG TAT GG TTGAG TAGGT-3' | 10 |
| $f_{(6,30)}$ | 5'-AGTGTT TGAGG TAGAG TGATG TAT GG TTGAG TAGGT-3' | 11 |
| $f_{(5,30)}$ | 5'-GTGTT TGAGG TAGAG TGATG TAT GG TTGAG TAGGT-3' | 12 |
| $f_{(4,30)}$ | 5'-TGTT TGAGG TAGAG TGATG TAT GG TTGAG TAGGT-3' | 13 |
| $f_{(3,30)}$ | 5'-GTT TGAGG TAGAG TGATG TAT GG TTGAG TAGGT-3' | 14 |
| $f_{(2,30)}$ | 5'-TT TGAGG TAGAG TGATG TAT GG TTGAG TAGGT-3' | 15 |
| $f_{(1,30)}$ | 5'-T TGAGG TAGAG TGATG TAT GG TTGAG TAGGT-3' | 16 |
| $f_{(0,30)}$ | 5'-TGAGG TAGAG TGATG TAT GG TTGAG TAGGT-3' | 17 |

Regulatory mechanisms affecting DNA dynamics in vivo may involve protein-less structural-functional determinants, in particular, interactions of DNA strands with invading RNA molecules. A diverse array of DNA nanotechnology platforms suitable for time-lapse analysis of protein-less DNA strands dissociation and re-association reactions were designed and tested based on measurements of strand displacement kinetics in the experimental context modeling the conventional DNA double helix, slipped strands and nucleotide mismatch bubbles, and DNA four way junctions (4WJ) nanostructures. In some embodiments, the engineering design techniques utilize conversion of a chemical cue into a substantial mechanical strand displacement detected by time-lapse fluorescence measurements. This approach enables quantitative experimental analyses of strand displacement reaction kinetics induced by invading RNA and DNA strands by modeling common structural features of replication forks associated with early and late replication timing zones (RTZ), sequences of transcription start sites (TSS) and Z-DNA forming regions (ZDR). In other embodiments, the strand displacement is detected by electro-signal change measurements.

Introduction of a single nucleotide toehold and products of cytosine methylation/deamination reactions markedly enhanced the kinetics of DNA strands displacement. RNA and DNA invading strands containing C/G toehold sequences induce 15-fold faster DNA strand displacement reactions compared to the invading strands bearing A/T toehold sequences (for toehold lengths 10≥n≥1). Higher DNA strand displacement kinetics of invading strands containing C/G toehold sequences represents an underlying mechanism of observed genome-wide associations of CG-rich sequences with early RTZ, TSS, and ZDR. Small non-coding RNA transcribed in vivo from genomic regulatory loci represents most likely candidates to function as invading molecules facilitating DNA strand displacement reactions associated with replication, transcription, enhancers' activities, DNA repair, and transitions between B-DNA and Z-DNA conformations.

Nucleosome repositioning and displacement at functionally active genomic loci continually creates short protein-less segments of DNA double helix undergoing transitions between double-stranded and single-stranded states. Multiple design and engineering strategies and different methods to fuel and drive nano-devices were utilized to study protein-less mechanisms of DNA strands dissociation and re-association processes. Strand displacement reactions employing toeholds rely on having favorable energy for displacing hybridized DNA. A toehold-less strand displacement method with non-conventional base pairings in DNA double helix utilizes deoxyinosine instead of deoxyguanine, which hybridizes with deoxycytosine, but with less energy than deoxyguanine. In addition to fluorescence-based monitoring of strand displacement, the performance of these devices can be visualized because they are able to perform a specific motion and acquire defined geometrical shapes in response to new DNA and/or RNA strands being introduced. DNA and RNA strand hybridization with mismatches can occur naturally in vivo through mutations and single nucleotide polymorphism (SNP) and by changing the number of mismatches, affinity of interactions between strands can be controlled. A novel combinatorial design was employed to create a self-sustaining nano-device in which by controlling both mismatches and hybridization length of interacting strands repeated capture and release of the same DNA strands was achieved. This approach creates a platform that allows for dissociation of DNA strands following the capture of select invading sequences and then targeted release of captured sequences and subsequent re-association of the same DNA strands thus modeling multiple cycles of protein-less dynamics of DNA strands dissociation and re-association.

The disclosed technology performs the systematic analysis of DNA strands displacement reactions using a suite of nano-devices specifically designed for discovery and characterization of the protein-independent mechanisms governing DNA double helix dynamics. The experiments employed a uniquely broad panel of toehold-less and toehold-bearing nano-devices including conventional DNA double helix, DNA double helix containing inosine and 5-methyl-cytosine nucleotides, four way junction (4WJ) DNA nano-systems, and a self-sustaining nano-device in which repeated continuous cycles of capture and release of the same DNA strands was achieved. One of the unique features of inosine-based nano-devices is the thermodynamic resemblance of molecular bonds of naturally-occurring wobble base pairing, including G:U, I:U, I:A, and I:C bonds. Notably, thermodynamically similar bonds can be formed in DNA double helix in vivo as a result of C/5mC/5hmC deamination, suggesting that DNA double helices containing G:U, G:T, and G-5hmU bonds should manifest increased sensitivity to invading strands and high likelihood of transitions between double-stranded and single-stranded states.

In some embodiments, the disclosed technology utilizes an inosine-based partial strand displacement scheme in the context of DNA four way junctions (4WJ) modeling structural motifs of DNA replication and providing a model system for accurate analytical determination of DNA strand displacement reaction kinetics. Nano-devices demonstrating on-demand dissociation and re-association of DNA strands in response to induced 4WJ expansion and contraction cycles were developed using this approach. Similar to the conventional DNA double helix, controlled on-demand induction of 4WJ expansion and contraction cycles was triggered by addition into system of toehold-bearing invading strands. RNA or DNA invading strands containing C/G toehold sequences induced 15-fold faster DNA strand displacement reactions compared to the A/T toehold-bearing invading sequences. Invading strands with toehold sequences containing A/C/G and T bases manifest intermediate DNA strand displacement kinetics. These results are in agreement with the reported curves for toehold saturation in a publication by Zhang et al., "Control of DNA Strand Displacement Kinetics Using Toehold Exchange," *J. Am. Chem. Soc.* 131(47): 17303-17314 (2009). The best-fit values from their 3-step model were kn=$6.0 \times 10^6$ M-1 s-1 ($\varepsilon \approx 3$) for toeholds composed C/G bases, kn=$3.0 \times 10^6$ M-1 s-1 for a typical sequence containing A/C/G and T bases ($\varepsilon \approx 4$), and kn=$4.0 \times 10^5$ M-1 s-1 for A/T only toehold sequences ($\varepsilon \approx 5$). For comparison the function Pc(n,b) was plotted as multiples of the aforementioned values as kfPb(n,b).

Marked differences in kinetics of strands displacement are apparent for sequences having a toehold length n=1, which is expected to occur in genomes very frequently as a result of the spontaneous methyl-cytosine deamination reactions of CpG sequences. The CpG sites are hypermutable because the C of CpGs is considered a preferred site of DNA methylation, and methyl-C(mC) is prone to mutate to T via spontaneous deamination. The net result is that CpGs are replaced over time by TpG/CpAs sequences and the overall mCpGs mutation rate is estimated at 10-50 times the rate of C in any other context, or of any other base in the genome. It was reported that ~25% of all methylation events identified in hESC were in a non-CG context. Methylation in non-CG contexts seems specific to ESC because non-CG methylation disappeared upon induced differentiation of the hESC. These data suggest that the mutation-driving mechanism caused by the spontaneous deamination of mC to T may be relevant to the non-canonical methylation events occurring in hESC at non-CG (e.g., CHH and CHG, where H is any base) sequences.

CpG methylation and deamination play a highly important role in the inactivation of transposons and protecting mammalian genomes from their harmful mutational activity. Methylation and deamination of CpGs embedded within Alu transposons in the human genome resulted in generation of thousands of p53-binding sites with the preferred core motif composed of CpA and TpG dinucleotides. It has been demonstrated that that CpG deamination events may create TF binding sites with much higher efficiency than other single nucleotide mutational events. Evolutionary analysis of TF binding sites in ESC is consistent with the idea that CpG deamination is a major contributor to creation of novel binding sites for NANOG, NANOG, OCT4, and CTCF. These naturally-occurring genome editing mechanisms were recently linked to the creation of the unique to human transcription factor-binding sites. They may play an important selection-supported biological role in human evolution by markedly increasing a combinatorial regulatory complexity of individual genomes and enhancing phenotypic diversity of individual cells within populations.

Genome editing mechanisms, defined as changes of DNA sequences altering the Watson-Creek base pairing, are not limited to the spontaneous 5mC deamination. Recent experiments demonstrated that in physiological conditions DNA sequence undergoes major structural changes, which markedly affect double helix dynamics and functions. These structural modifications of DNA sequences are due to activity of TET and APOBEC enzyme families. Coupled with base excision repair, they function to erase DNA methylation marks and recover cytosine bases, thus reconstituting the conventional structure of DNA double helix. Because 5mC is the primary target of this regulatory pathway, the corresponding changes of DNA sequences can be defined as DNA methylation-associated genome editing mechanisms. Genome editing mechanisms, which are attributed to the elevated rate of spontaneous deamination of 5mC and increased enzymatic activity of the APOBEC family of cytidine deaminases, were implicated as a major source of mutations in humans. These mutation signatures, characterized, in part, by prominence of C>T substitutions, are present in 29 out of 30 different types of human cancers. The prevalence of this type of mutations, defined as the percentage of samples from data set of 7,042 cancers in which the signature contributed significant number of somatic mutations, exceeds 60% in human cancer samples, reaching 68% of all mutations in some cancer samples.

Transitions between B- and Z-DNA conformations result in major structural changes of DNA double helix at the B-Z junctions where the base pairing is broken and two bases are extruded from the double helix, thus creating DNA double helices containing single nucleotide toeholds. Notably, similar structural changes were observed during the crystal structure and molecular dynamics studies of interactions of DNA double helix with 5mC-DNA-binding proteins. The 5hmC base is flipped out of the DNA double helix and the 5hmC hydroxyl group participates in hydrogen bonding stabilizing the interactions of 5hmC-modified DNA with the SET and RING-associated domain of the Uhrf1 protein. X-ray diffraction determination of the high-resolution structures of the palindromic Dickerson dodecamer containing either 5hmC or 5mC instead of either the 2nd or 3rd cytosine demonstrated that cytosine methylation appears non-mutagenic since neither the helical structure nor the thermodynamics of DNA double helix are changed. Taken together, these data suggest that polymerases cannot distinguish 5hmC and 5mC modifications from unmodified cytosine.

Bivalent ions significantly enhance the transition of DNA double helix from B to Z conformations. The effect is markedly (1000-fold) higher on DNA sequences containing 5mC and is readily detectable at physiological concentrations of bivalent ions. This disclosure document suggests that invading RNA molecules interact more efficiently with DNA double helix in Z conformation. Endogenous RNAs may function as efficient inducers of DNA double helix transitions from double-stranded to single-stranded states at genomic loci containing either conventional cytosine or 5-methyl-cytosine nucleotides. Several lines of experimental evidence support the notion that this model reflects biologically relevant regulatory mechanisms. Cytosine methylation appears to decrease kinetics of DNA strand displacement reactions in response to invading RNA molecules, thus decreasing the likelihood of transition from double-stranded to single-stranded states of DNA double helix. These observations are in agreement with the results of high resolution melting experiments demonstrating that methylated DNA has increased thermal stability and 5-methylcytosine hydroxylation reduces DNA thermal stability. Consistently, spectroscopic and calorimetric analyses have revealed that 5hmC introduction reverses the stabilizing effect of 5-methylcytosine on double-stranded DNA. The inhibitory effect of cytosine methylation may be reversed and sensitivity of DNA double helix to the invading RNA molecules is increased in the presence of bivalent ions at physiological concentrations.

The disclosed technology has potentially significant translational implications. Discovery of architectural principles for design and engineering of analytical nano-devices manifesting ~200,000-fold improvement in sensitivity of detection and discrimination of nucleic acid molecules at a single nucleotide resolution should pave the way for a wide range of diagnostic and therapeutic applications. The disclosed technology is ready for the immediate implementation in vitro. Most recent experiments demonstrating the stability and bioactivity of DNA/RNA hybrids in vivo support the feasibility of the assessment of its utility in animal studies and clinical trials in the near future. Importantly, CG-rich and CpG sequences and active transcription have been associated with the early RTZ, TSS, and ZDR in multiple independent studies utilizing either genome-wide approaches or analyses of specific genomic regions. Toehold-containing CG-rich DNA double helix manifest higher sensitivity to invading nucleic acids compared to AT-rich DNA sequences and the marked differences are observed between conventional and toehold-bearing DNA nano-devices having single base toeholds. Results disclosed herein suggest that increased kinetics of DNA strand displacement induced by CG-rich invading strands and variable responsiveness of 5mC-based DNA double helix to invading RNA molecules may reflect common molecular mechanisms underlying these observations. RNA-guided DNA strands displacement reactions in vivo are most likely to occur during a rapid transient DNA unwrapping off the histone surface. Nucleosomal DNA undergoes rapid spontaneous unwrapping/rewrapping cycles: it remains fully wrapped for ~250 ms before unwrapping and rewrapping within ~10-50 ms. Spontaneous conformational changes of nucleosomes leading to a transient lift of a DNA stretch from the histone surface and a site exposure for sequence-specific DNA binding proteins are likely to occur at the genomic loci harboring "nascent" chromatin lacking linker histone H1. Genome-wide pervasive transcription continually generates small non-coding RNAs from up to 90% of human genome, including TSS, enhancers, and sites of replication origin, making RNA molecules particularly attractive candidates to function as invading strands inducing DNA strand displacement reactions associated with many biological processes.

Figure 1:
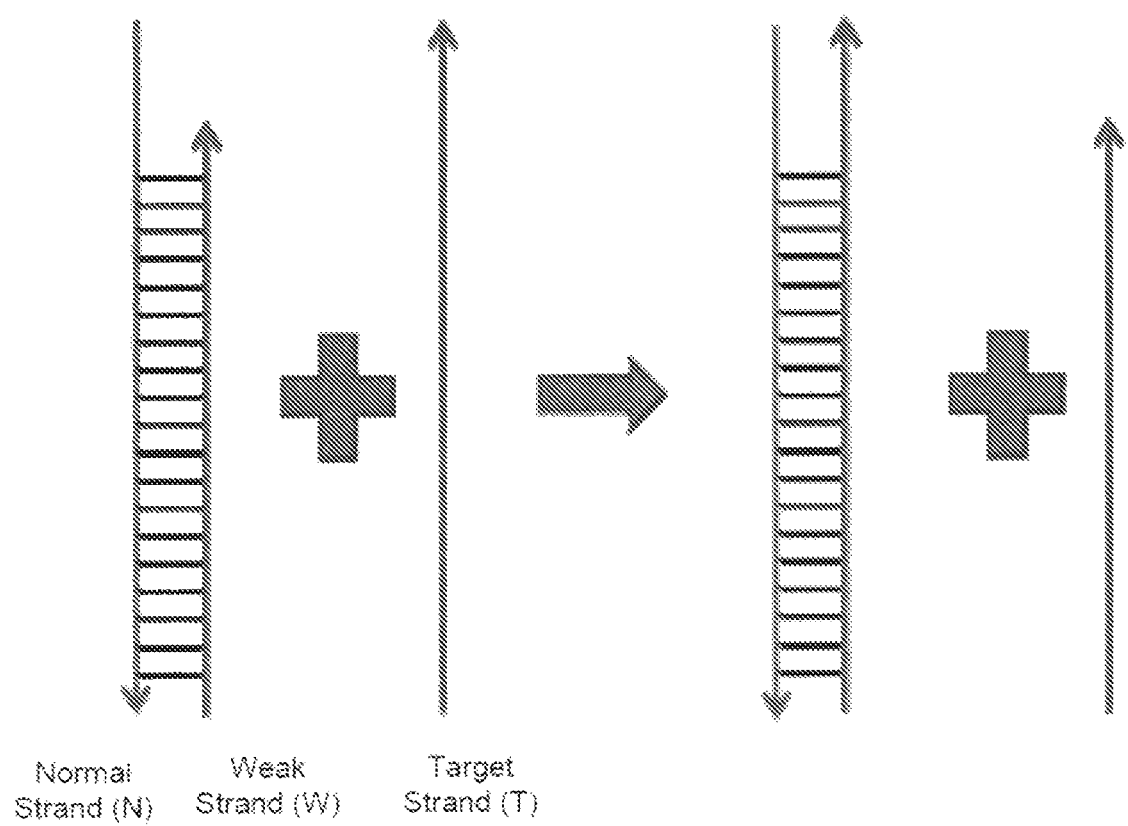
FIG. 1 illustrates an example of the scheme of operation of a DNA zipper.

An example scheme of strand displacement and single mismatch detection is shown in FIG. 1. DNA zipper is prepared by hybridization of two complementary strands (a normal strand and a weak strand). The normal strand has a prolonged toehold; while the weak strand is shorter than the normal strand by one or more nucleotide and/or contains one or more guanines (G) substituted with inosine (I) to lessen the affinity between the two strands. In the example illustrated by FIG. 1, the normal strand has a toehold part of 7 nt and its total length is 47 nt. The weak strand is 40 nt and 4 guanines are substituted with inosine (I). The 47-nt strand is called normal strand (N) and 40 nt strand is called weak strand (W) as it contains I to weaken the affinity. As shown in FIG. 1, when 47 nt of target strand (T), which is fully complementary with N, is introduced to the DNA zipper, it displaces W and hybridizes with N. Reducing the hybridization affinity between the N strand and the W strand can be achieved by replacing guanine(s) with inosine(s), including a toehold part, or both. The hybridization affinity can be modified because more guanines replacement by inosines or a longer toehold part results in weaker hybridization affinity between the strands. For example, if W does not contain I, hybridization affinity between W and N becomes too strong to displace W with T with the 7 nt of toehold; without I, it requires longer toehold to displace W strand by T. Thus the strand displacement can be summarized as [N:W]+T→[N:T]+W.

Figure 2:
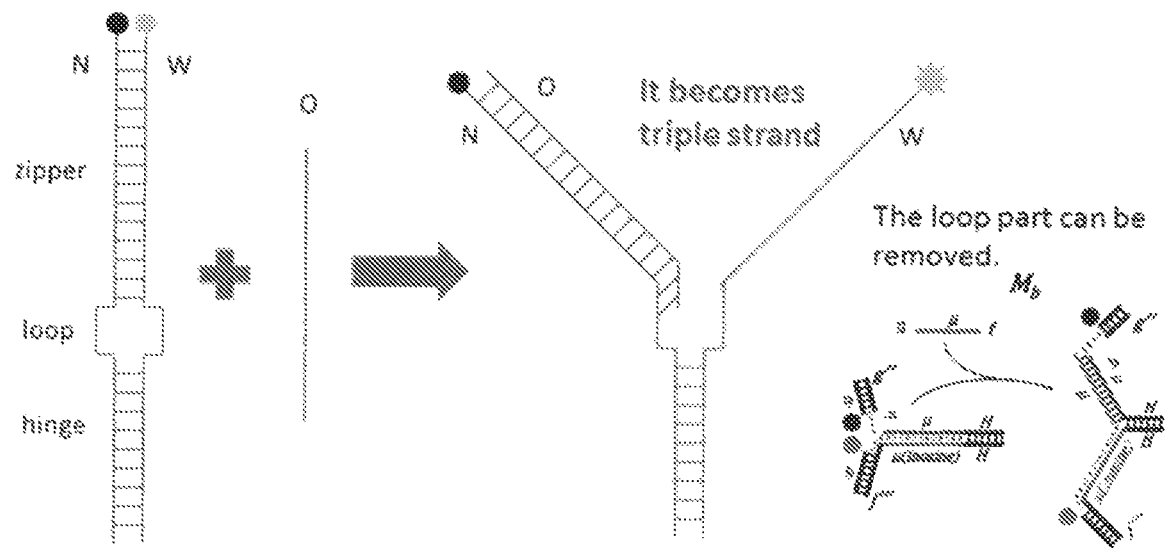
FIG. 2 illustrates a diagram of DNA zipper-based tweezers operable as a single nucleotide polymorphism (SNP) probe.

Another example scheme of strand displacement and single mismatch detection is shown in FIG. 2. DNA zipper-based DNA tweezers are prepared by the hybridization of two complementary strands. N and W strands consist of zipper, loop and hinge parts. The strands of the zipper and hinge parts are complementary and hybridized to each other, while the strands of the loop part are non-complementary and remain unhybridized. FIG. 2 shows an illustrative diagram of DNA zipper-based tweezers operable as a single nucleotide polymorphism (SNP) probe. The example DNA tweezers device shown in FIG. 2 includes a zipper structure bound by a hinge. In operation, for example, the zipper structure can be opened (e.g., unzipped) to form a triple stranded structure and undergo an increase in negative charge. In some implementations, for example, the DNA zipper-based tweezers device can be configured to have a length capable of reversibility.

Figure 3:
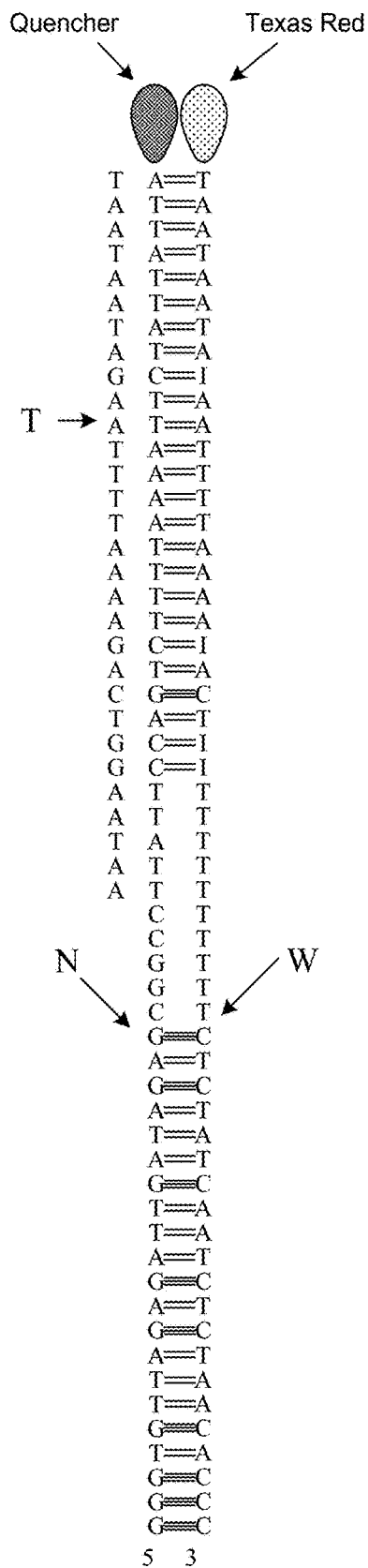
FIG. 3 shows an example of the structure of DNA tweezers with the specific sequence. The complementary target strand with a single mismatch has T instead of G in the middle of the sequence. The N strand has a toehold and the W strand contains 4 inosines (I). The quencher and Texas red fluorophore are also shown.
Figure 4:
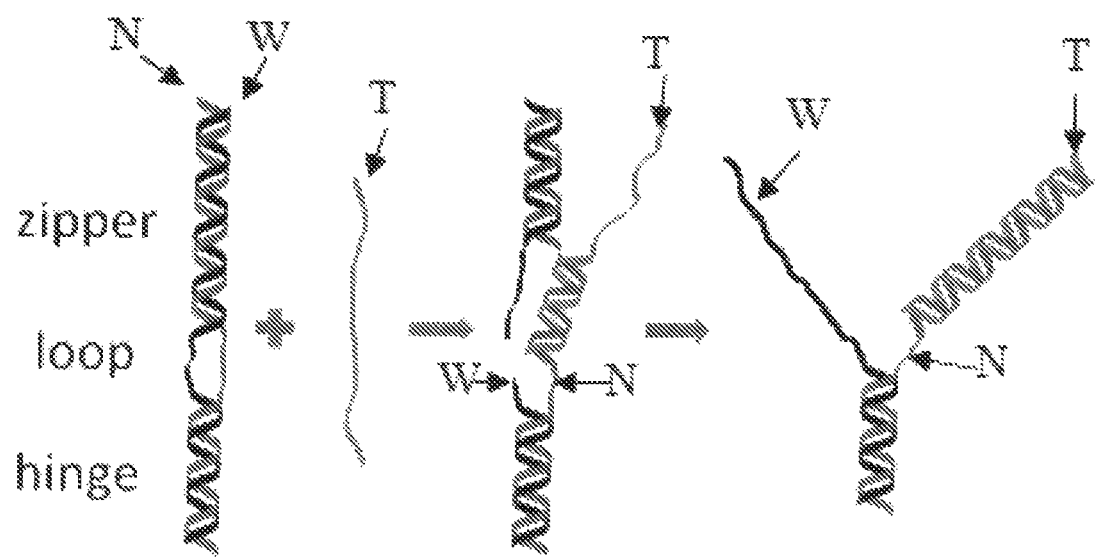
FIG. 4 illustrates the DNA tweezers probe action. In one example, the normal strand (N) contains 10 nt of loop. When the perfect-match target strand (T) approaches the DNA tweezers, the target strand (T) displaces the weak strand (W) by binding to the loop. The tweezers remain bound by the hinge, thus forming a triple-stranded complex.

In some embodiments, both normal and weak strands (N and W) are 57 nt, and the N and W strands are complementary to each other except for 10 nt of loop part in the middle of the DNA tweezers. W strand contains 4 guanines which are substituted with inosines (I) to lessen the affinity between the two strands. The structure of the DNA tweezers with the specific sequence is shown in FIG. 3. As shown in FIG. 4, when 30 nt of target strand (T), which is fully complementary with N and 5 nt of the loop part on N, is introduced to DNA tweezers, it displaces W and hybridizes with N. Even though the displacement happens, the hinge part is not dissociated and remains binding with the DNA tweezers such that the triple stranded complex is formed. The hybridization affinity between the N and W strands is reduced by replacement of guanine(s) with inosine(s), introducing a longer toehold part, or both.

In some embodiments, an example of the probe design on the graphene chip is shown in FIG. 58. In this embodiment, the sensing results in transition from double-stranded state to a single stranded-state of the probes on the chip and decrease of resistivity. This approach has several advantages, including simplicity of the probe design and optimization; each individual chip will be fine-tuned for exact background calibration before operation. Thus, disclosed herein is a probe that utilizes strand displacement reaction to sense, detect, discriminate, observe, quantify, measure, and report the presence of a specific nucleic acid molecule. In some embodiments, at least one strand of the probe is a DNA molecule. In some embodiments, at least one strand of the probe is an RNA molecule. In some embodiments, the probe comprises a DNA/RNA hybrid molecule. Also disclosed is a device that utilizes strand displacement reaction to sense, detect, discriminate, observe, quantify, measure, and report the presence of a specific nucleic acid molecule.

The probe design utilizing principle(s) of strand displacement reactions for sensing, detection, discrimination, observation, quantification, measurement, and reporting the presence of a nucleic acid molecule. The probe design includes one or more of the following elements to enable and facilitate the strand displacement reactions: i) toehold extension; ii) chemical modification of strand monomers; and iii) structural changes of interacting strands (such as stem-loops, etc.). The probe design results in changes of conductance of electrical signals due to strand displacement reaction.

The probe design can be optimized for sensing a nucleic acid molecule utilizing strand displacement reaction in a solution. Additionally, the sensor design can be improved by placing the optimized probe for strand displacement reaction on a solid phase.

Detection by Fluorescence Labeling

Figure 5:
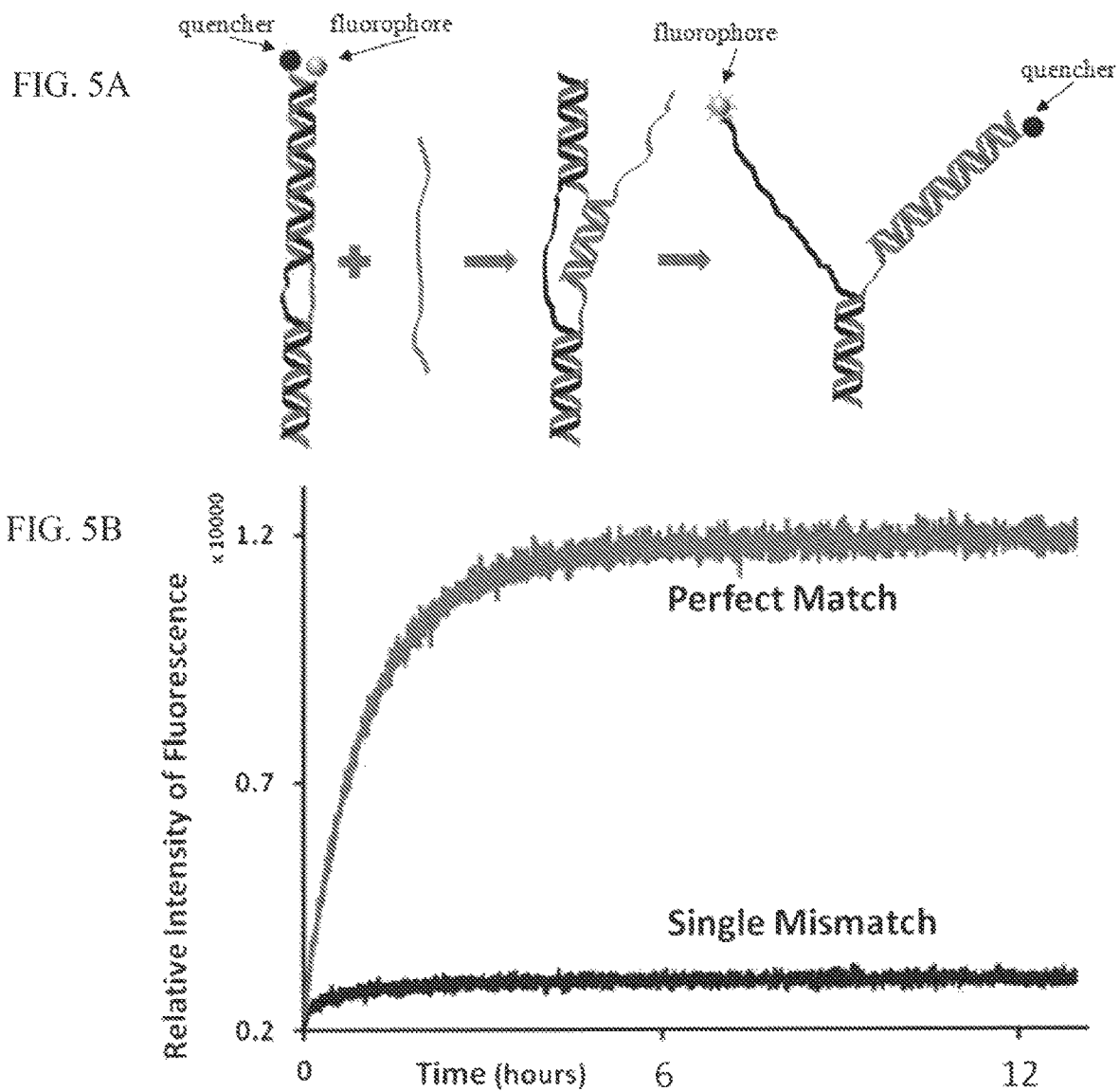
FIG. 5 illustrates single-mismatch detection using fluorescently labeled nucleotides.

In some embodiments, strand displacement can be monitored over time with fluorescence labeling (FIG. 5 and FIG. 33). As illustrated by FIG. 5, a fluorescent label, such as a Texas Red fluorophore is labeled at the end of W strand and a fluorescence quencher is at the end of N. The quencher absorbed emission from the fluorescence when it was adjacent to fluorescence label, thus causing fluorescence to be quenched upon the hybridization of N and W strands. When the perfect match T strand is added to the sample, strand displacement happens quickly, thereby separating the fluorophore and quencher, causing a brighter fluorescence signal. However, when the T strand having one or more mismatches is added, strand displacement happens at a much slower rate and much lower fluorescence signals are measured compared to a perfect match T strand. The formation and operation of the probes, such as DNA zippers and DNA tweezers, with perfect match T strand and T strands with one or more mismatches can be proven by DNA gel electrophoresis as well.

Detection by Graphene FET

In some embodiments, the binding of target nucleic acid molecules to the nucleic acid probes can be detected by electrical sensors using a graphene FET chip and the electrical signals can be transmitted wireless. For example, the nucleic acid probes can be attached to the surface of the graphene FET chip as follows: 1-Pyrenebutanoic acid succinimidyl ester (PASE) can be used to link graphene and amino group at the N-terminal of a nucleic acid probe. The pyrene group of PASE and graphene is attracted to each other with π-π stacking interaction and the amino group at N and amide bond on PASE can be covalently linked. See FIG. 35.

In one example, 30-nucleotide long DNA strands can be immobilized onto the graphene surface, by the π-π stacking with the probe DNA strand. The surface of each graphene chip can be saturated with a probe DNA resulting in a measured increase in the resistance of the graphene. The target DNA, which is complementary to the probe DNA, is the DNA to be detected. When the target DNA hybridizes to the probe DNA, it causes the π-π stacking of the pyrene label on the DNA with the graphene to be critically weakened. This results in the detachment of the probe/target duplex from the graphene surface resulting in a decrease in the measured resistance of the graphene.

Figure 6:
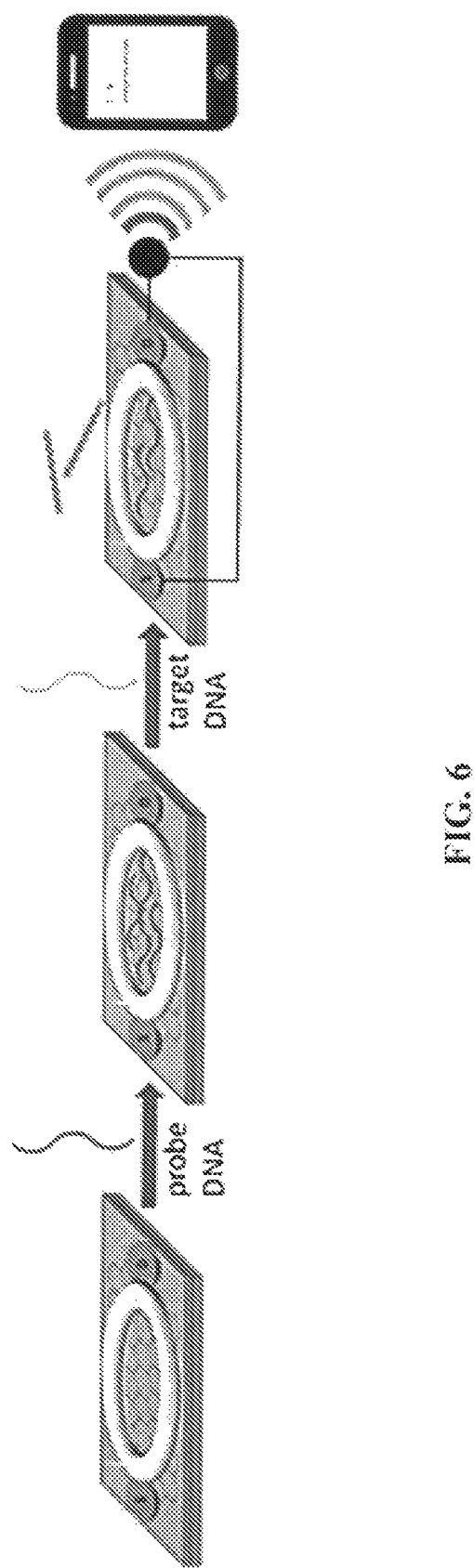
FIG. 6 shows an example of the overall scheme of a nano-sensor according to some embodiments.

As shown in FIG. 6, when probe DNA 102 is treated on the surface, DNA and graphene are attracted by π-π stacking interaction, which results in increase of resistance of the channel. When target DNA 104 is added consecutively, it binds to the probe DNA and forms double helix 106. As a result, π-π stacking interaction becomes significantly weakened, thus double helix 106 leave surface, resistance is decreased.

Fabrication of Graphene FET Chip

Figure 7:
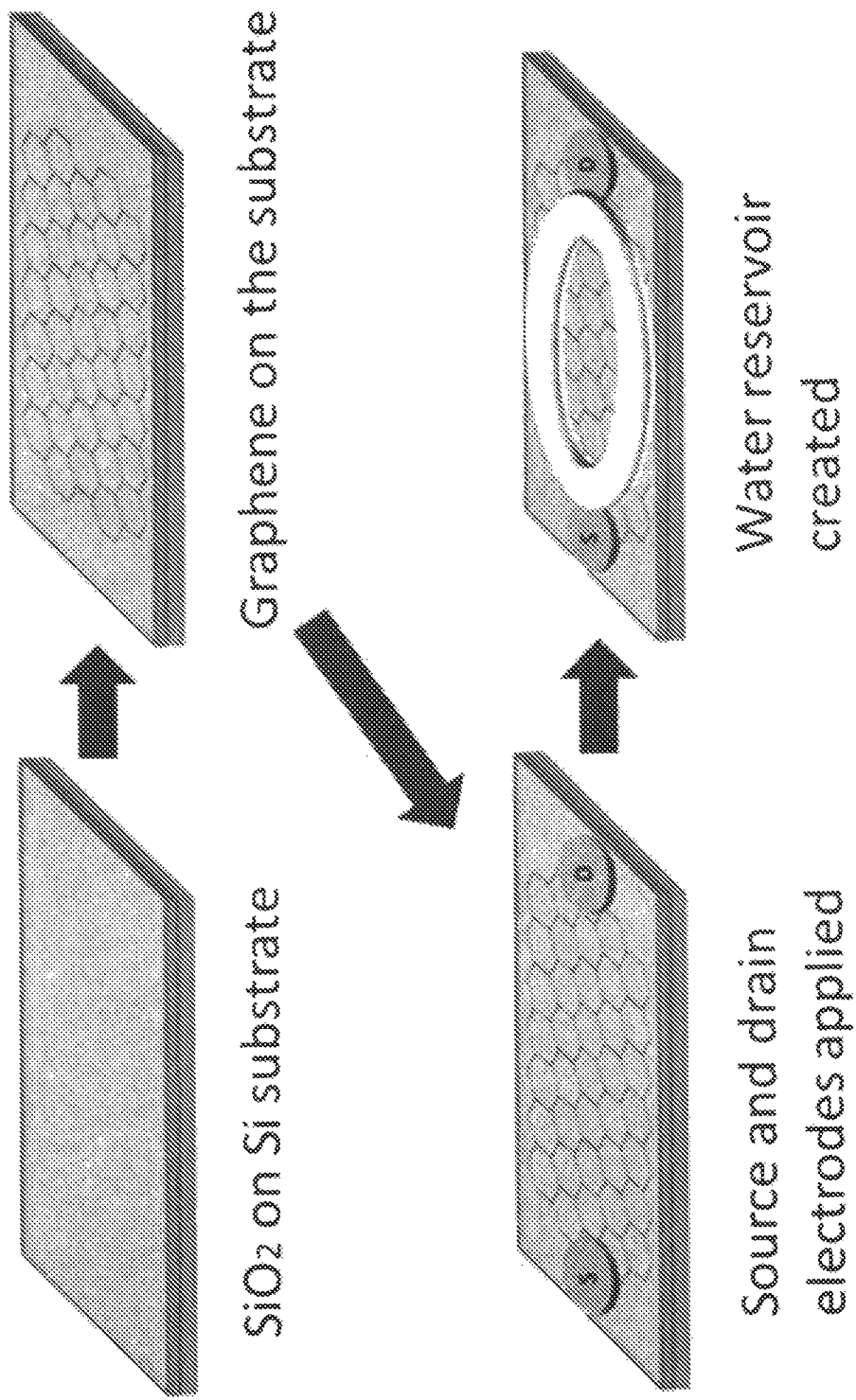
FIG. 7 illustrates an example of the scheme of fabrication of graphene FET.

As illustrated in FIG. 7, a graphene FET with two electrodes and a liquid gate chamber can be fabricated to examine electrical sensing of a target nucleic acid using the nucleic acid probes disclosed herein. For example, a graphene FET can be fabricated by transferring a graphene channel (4 mm×6 mm) onto a silicon oxide-coated wafer using an established method, as illustrated by FIG. 7. The source and drain electrodes can be applied by silver paste and silicone rubber can be used to insulate the electrodes and create a solution reservoir.

Functionalization of Nucleic Acid Probes on Graphene FET Chip

In some embodiments, the nucleic acid probes are brought into contact with the surface of the graphene FET chip such that the probes are attached to the surface of the graphene FET chip. Optionally, the surface of the chip is saturated with the nucleic acid probes. Subsequently, the nucleic acid molecules to be tested, including target nucleic acid molecules, are introduced and allowed to bind to the probes such that electrical measurements can be taken. For example, the probe and target nucleic acid molecules are treated by dropping appropriate concentrations of each in the reservoir on the graphene FET chip for a sufficient period of time, e.g., for an hour, to allow the probes to bind to the surface of the FET chip or to allow the target molecules to bind to the probes. The chip is then rinsed gently with a buffer, e.g., phosphate buffered saline (PBS). All volumes of treated samples, including the probes and the targets can be as small as about 90 µL.

Electrical Measurement

In some embodiments, I-V curves and resistance can be measured in a semiconductor parameter analyzer equipped with a probe station. Silver wire can be used as an electrode, which applies gate voltage (Vg) to the 12.5 mM $MgCl_2$/30 mM Tris buffer solution. Tests can also conducted with 1×PBS buffer solution. Vg can be swept from −0.5 to 1 V, and drain-source voltage (Vds) can be between 0.05 and 0.3 V. Drain-source current (Ids) can be measured at an assigned Vds. Resistances can be measured between 0 and 100 mV of Vds.

In some embodiments, after measurements on the probe station, resistance measurements can be simultaneously performed using a standard digital multi-meter (DMM) (Fluke 175 True RMS multimeter) and connected to the smartphone via the wireless system. The source voltage can be swept between 0 and 0.5 V. Current values can be converted into a voltage signal by introducing a pull-up resistor of 1 kΩ. The potential difference which corresponds to 1000 times the current value can be measured by the device. This data can be sent to a smartphone for further data processing. Voltage values can be plotted against their respective current values with a trend line. Gradient of the trend line represents resistance of the entire circuit with the resistivity of device obtained by subtracting the resistance of the other components, 1 kΩ pull-up resistor and 10 kΩ filtering resistor.

Wireless Communication

Figure 8:
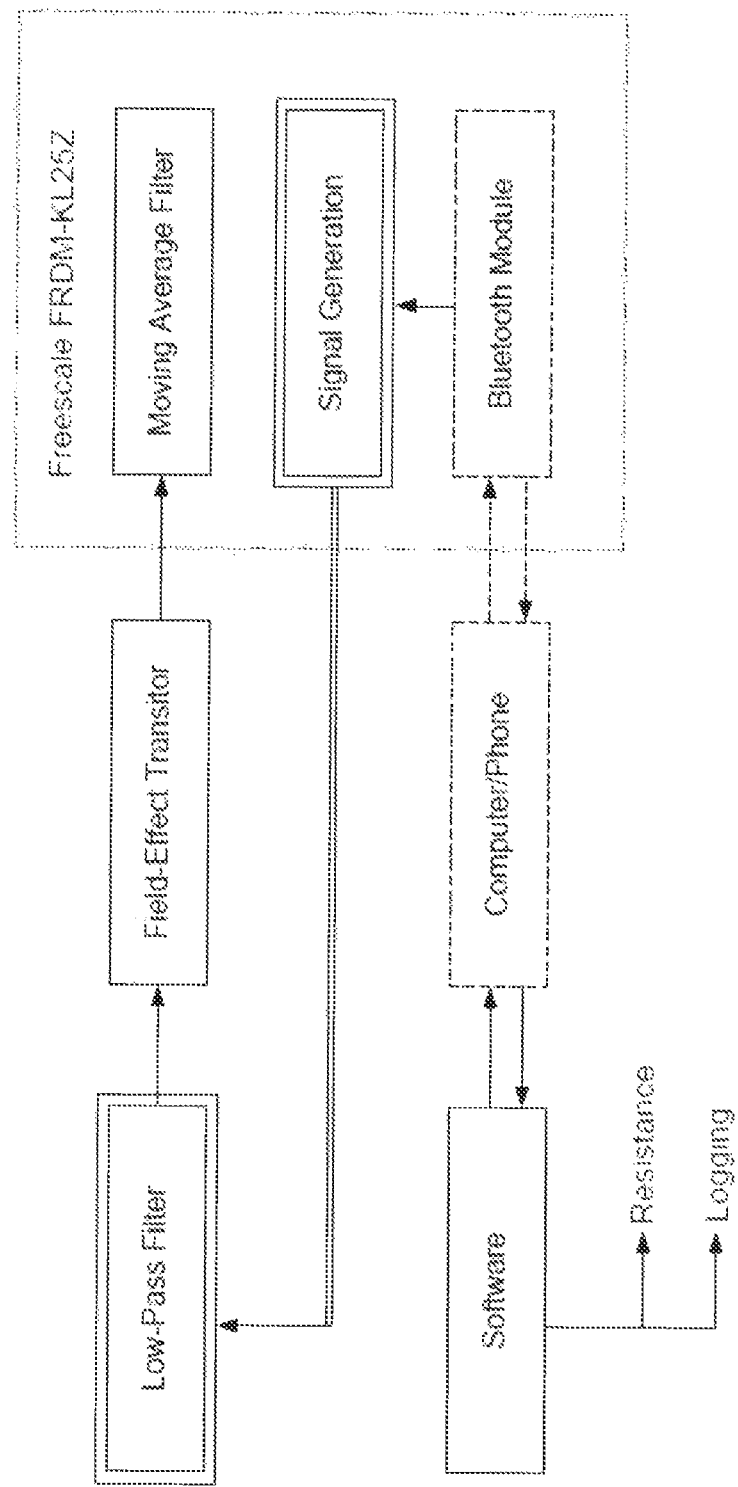
FIG. 8 shows an example of the top-level design of the device according to some embodiments.
Figure 9:
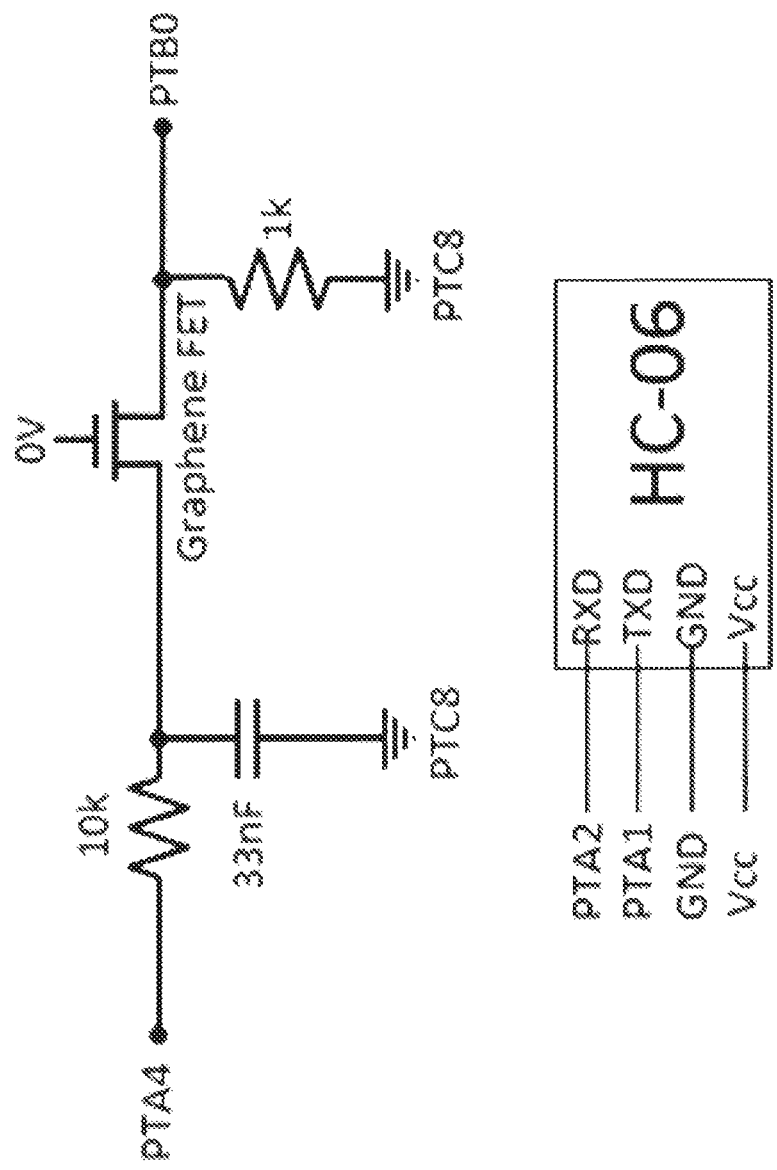
FIG. 9 shows an example of the low-level circuit design of the device according to some embodiments.

The graphene chip can be integrated into a proprietary wireless system using a microcontroller board. A flow chart of the top-level design of graphene chips communication with a smartphone is presented in FIG. 8 with different operation aspects highlighted (dashed: communication, double-lined: signal generation, single-lined: measurement). The low-level design is presented in FIG. 9. In some embodiments, the microcontroller board can be a Freescale FRDM-KL25Z with serial support, I2C and UART communication protocols. It also provides Pulse-Width-Modulation (PWM) signal output and Analogue-to-Digital Converter (ADC) allowing the board to generate and read analogue signals. The analytical performance of the integrated wireless biosensor platform is validated by demonstrating that electrical signals, such as current and voltage, are reliably received and quantitatively processed using wireless communication to personal electronic devices, laptops and smartphones, for further analysis and reporting.

Figure 10:
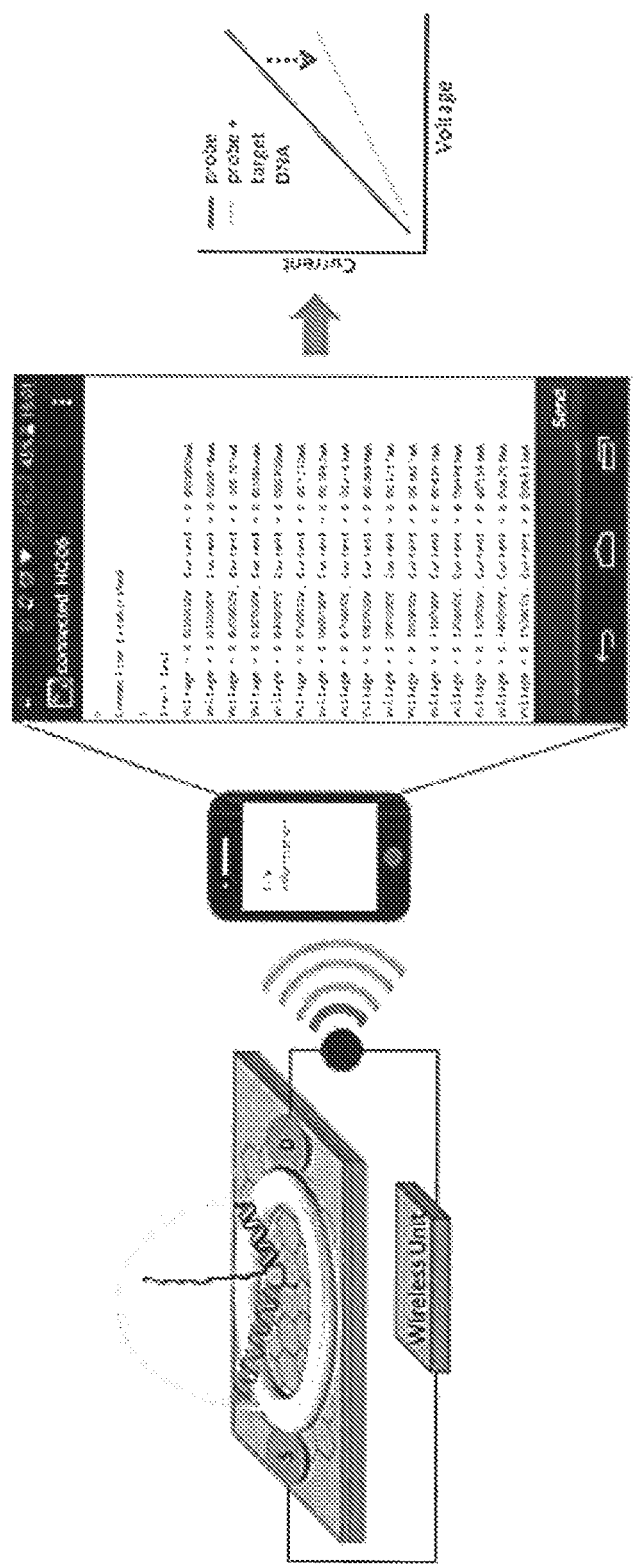
FIG. 10 shows an example of the scheme of data transmission from the biosensor chip to a smartphone. Electrical voltage and current data are transmitted to a smartphone for further processing to obtain resistance values. The magnified screenshot of Bluetooth terminal shows data received by the Smartphone during a test demonstrating communication between device and phone. The data is interpreted as I-V graph which shows resistance changes before and after the detection of DNA.

In some embodiments, communication can be established through the HC-06 Bluetooth module. The HC-06 module communicates with the FRDM-KL25Z using the Serial RS-232 communication protocol while pairing with user electronics, phones and computers, over the Bluetooth communication standard. FIG. 10 shows the scheme of data transmission from the biosensor chip to a smartphone. Electrical voltage and current data are transmitted to a smartphone for further processing to obtain resistance values. The magnified screenshot of Bluetooth terminal shows data received by the Smartphone during a test demonstrating communication between device and phone. The data is interpreted as I-V graph which shows resistance changes before and after the detection of DNA. The HC-06 module supports Bluetooth communication baud rates up to 115200 bps, a baud rate of 9600 bps can be used for communication with the smartphone device.

Generation of Wireless Signal

The FRDM-KL25Z microcontroller board can generate a digital approximation of an analogue signal using pulse-width-modulation (PWM). Typically, PWM signals give a relatively good representation of an analogue signal because most electronic appliances do not react to relatively small voltage changes, however, because of the electrolysis of aqueous solutions the graphene system is sensitive to significant voltage changes. The microcontroller board creates the PWM signal by switching the voltage digitally (between the only two modes) off (0 V) and on (3.3 V) producing an analogue signal determined by the time averaging 0 V and 3.3 V over each period interval. For example, to produce a PWM analog signal of 1 V, the microcontroller board generates a signal of 0 V for 70% of the time and 3.3 V signal for 30% of the time. The nature of PWM signals can therefore cause the DNA-chip to experience a voltage of 3.3V regardless of how small the "analogue" signal generated by the microcontroller board. This bias voltage can cause electrolysis of the aqueous electrolytes and its effect on the system is evident in I-V plot of the system before low-pass filtering.

Figure 11:
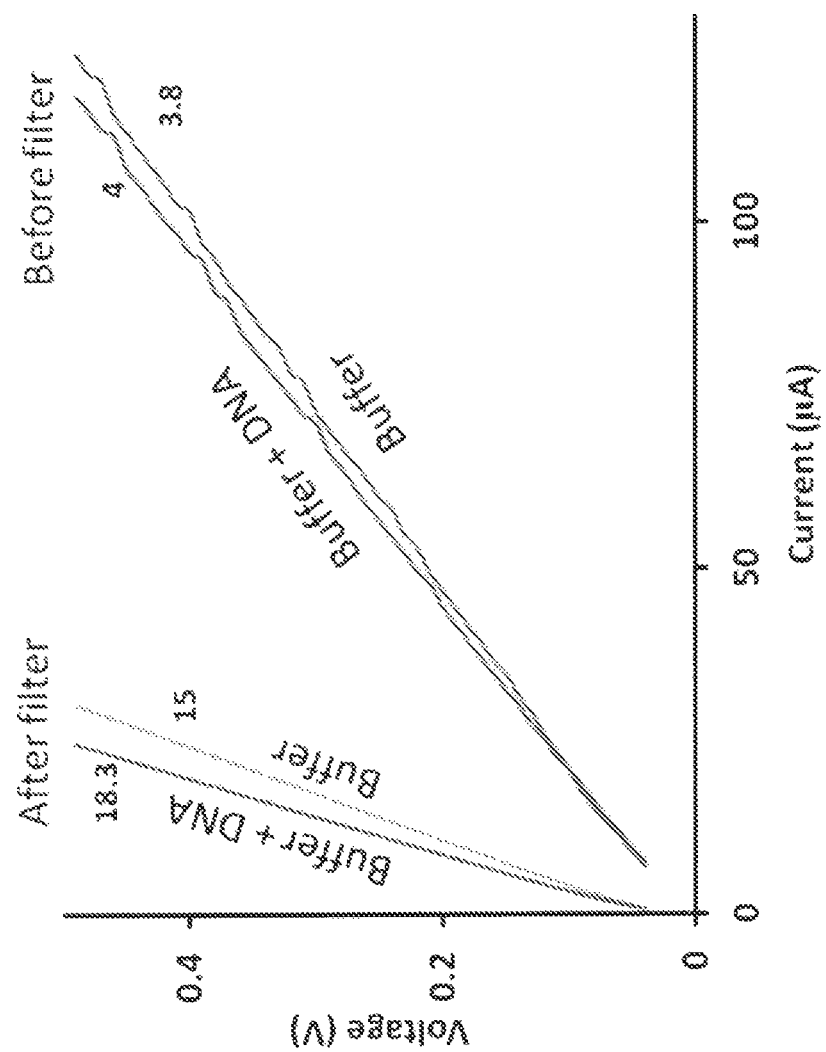
FIG. 11 shows I-V graphs comparing resistivity changes when DNA is added, before and after low-pass Filtering is performed. When the measurements were done without passing the PWM signal through a low-pass filter, similar resistance values, 0.0038MΩ and 0.004MΩ, illustrate the detachment of DNA from graphene surface regardless of how small the "analogue" signal generated by the device was. This is due to the nature of PWM signals, subjecting the DNA to 3.3V regardless of the "analogue" signal generated. When the measurements were done after passing the PWM signal through a low-pass filter, the change in resistance values, 0.0183MΩ to 0.015MΩ was more significant as compared to that of without low-pass filtering. This implies that applying a voltage of 3.3V caused DNA to detach from the graphene surface. Filtering was implemented in this device to ensure accurate measurement. RC low-pass filter with τ=330 μs was used. Numbers beside lines represent resistance in kΩ.

FIG. 11 shows an example I-V graph comparing resistivity changes when DNA is added, before and after low-pass filtering is performed, wherein numbers beside lines represent resistance in kΩ. When the measurements are done without passing the PWM signal through a low-pass filter, similar resistance values, 0.0038MΩ and 0.004MΩ, illustrate the detachment of DNA from graphene surface regardless of how small the "analogue" signal generated by the device is. This is due to the nature of PWM signals, subjecting the DNA to 3.3V regardless of the "analogue" signal generated. When the measurements are done after passing the PWM signal through a low-pass filter, the change in resistance values, 0.0183MΩ to 0.015MΩ is more significant as compared to that without low-pass filtering. This implies that applying a voltage of 3.3V causes DNA to detach from the graphene surface. In some embodiments, filtering can be implemented in this device to ensure accurate measurement. In some embodiments, RC low-pass filter with τ=330 μs can be used.

Figure 12:
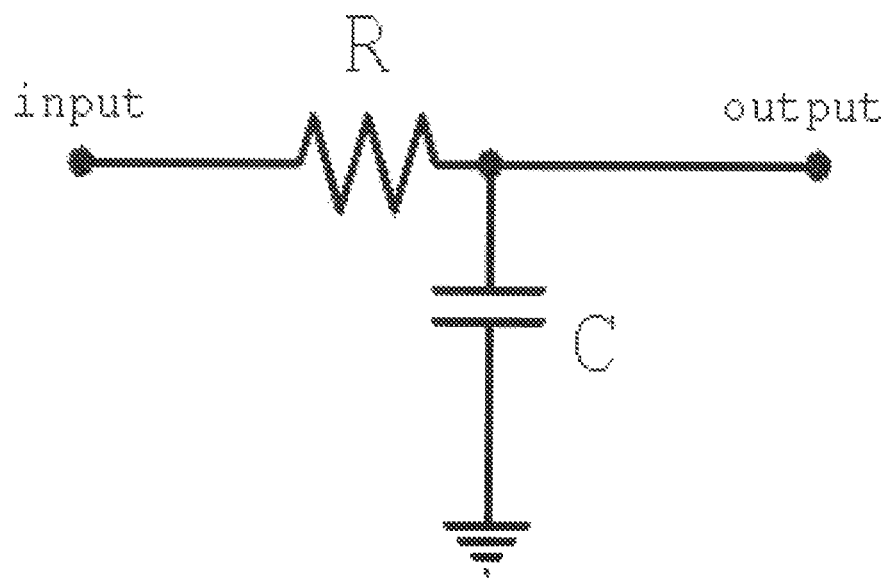
FIG. 12 illustrates an example of the circuit diagram of a 1st order resistor-Capacitor (RC) low-pass filter.

The effect from the 3.3 V spikes can be removed from the system by implementing a simple 1st order Resistance-Capacitor (RC) low-pass filter with the shown configuration, as shown in FIG. 12. An RC filter is characterized by its time constant (τ) which is defined as the time required to charge the capacitor to the fraction 1/e of its maximum charge, as shown in Eq. (1).

$$\tau = RC \qquad \text{Eq. (1)}$$

To determine the values of R and C, the PWM value can be 0.1V and PWM period can be 200 s. Time period where PWM signal is 3.3V ("high"):

$$t = \frac{0.1\ V}{3.3\ V} * 200 \mu s = 6.06 \mu s \qquad \text{Eq. (2)}$$

Calculate time constant required for $V_{out}$=0.1V using Eq. 3 to obtain Eq. 4:

$$V_{out} = V_{in}\left(1 - e^{\frac{-t}{\tau}}\right) \qquad \text{Eq. (3)}$$

$$\tau = \frac{-t}{\ln\left(1 - \frac{V_{out}}{V_{in}}\right)} \qquad \text{Eq. (4)}$$

τ can be further calculated as $$\tau = \frac{-6.06\ \mu s}{\ln\left(1 - \frac{0.1\ V}{3.3\ V}\right)} = 197\ \mu s \qquad \text{Eq. (5)}$$

A low-pass RC filter can be constructed using a 5 kΩ resistor and a 33 nF capacitor, using values R=5 kΩ and C=33 nF:

$$\tau = 5\ k\Omega * 33\ nF = 165\ \mu s \qquad \text{Eq. (6)}$$

Figure 13:
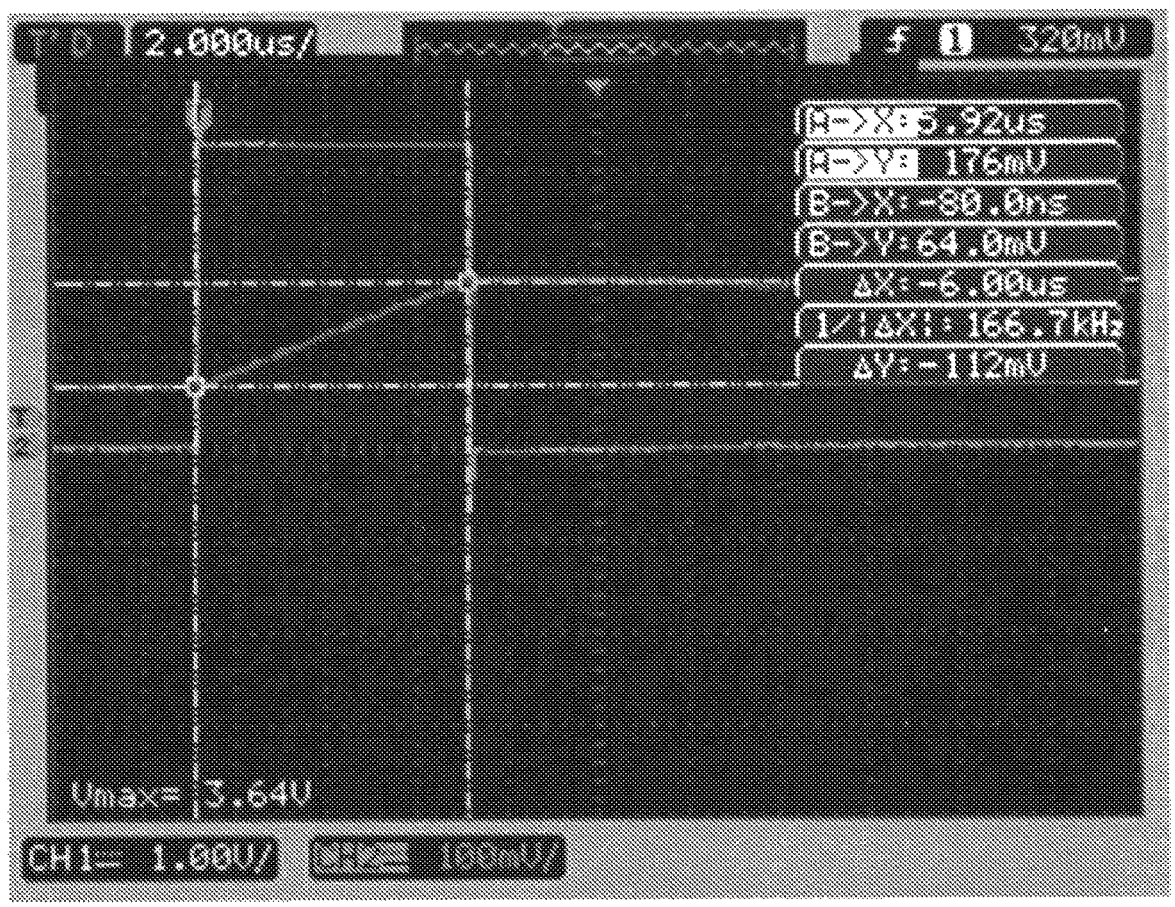
FIG. 13 shows an example of oscilloscope measurement of input voltage and filtered voltage with voltage levels measured to illustrate changes in the voltage applied to DNA before and after filtering. RC Low-Pass filter with τ=165 μs.

FIG. 13 shows an oscilloscope measurement of input voltage 502 and filtered voltage 504 with voltage levels measured to illustrate changes in the voltage applied to DNA before and after filtering. RC Low-Pass filter can have τ=165 μs. Initially, a measurement of $V_{out}$=0.1 V can be observed. However, as illustrated by cursors A and B in FIG. 13, $V_{out}$ varies from 0.176V to 0.064V. This huge range of $V_{out}$ values is undesirable as the graphene FET should be subjected to a more constant voltage. This can be achieved by increasing the time constant of the RC filter. The RC filter used in this study has a 10 kΩ, resistor and a 33 nF capacitor.

Figure 14:
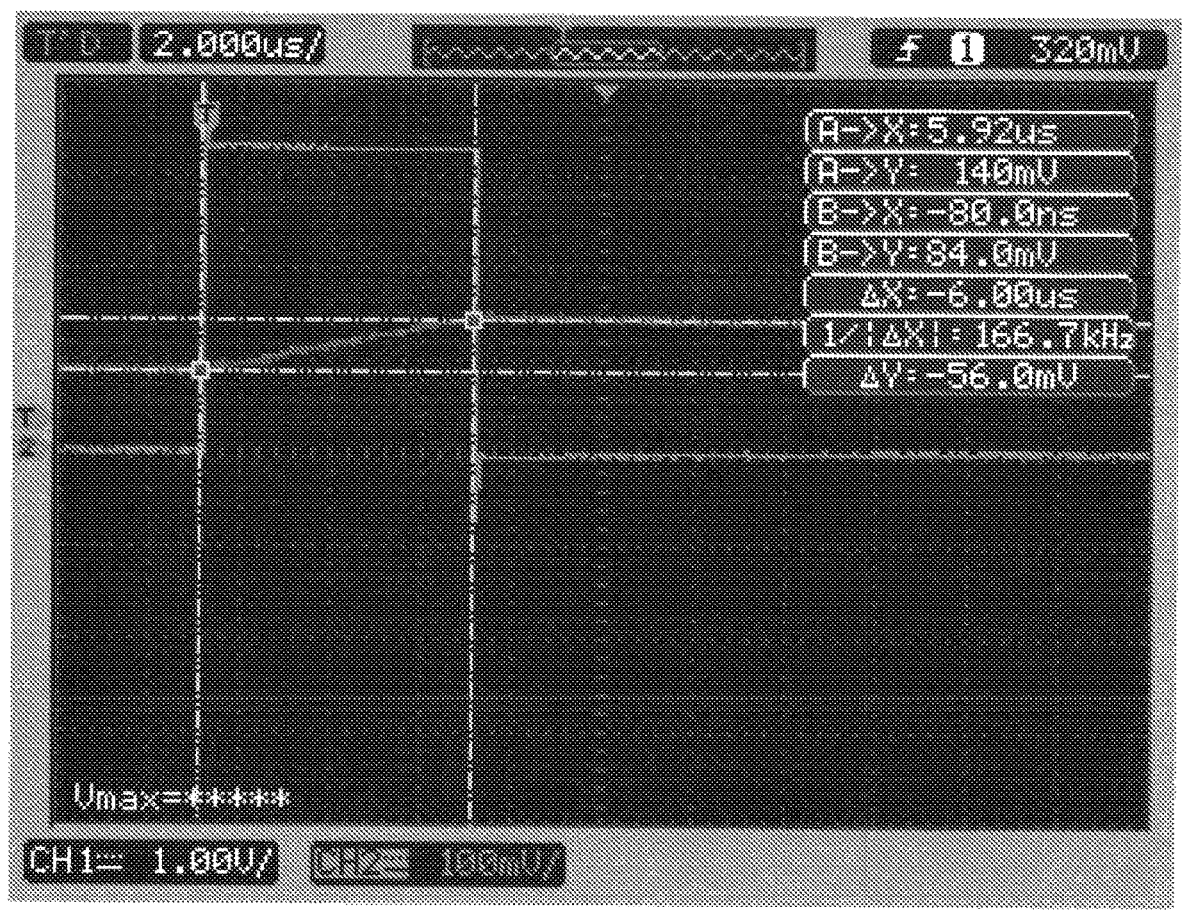
FIG. 14 shows an example of oscilloscope measurement of input voltage and filtered voltage with voltage levels measured to illustrate changes in the voltage applied to DNA before and after filtering. RC Low-Pass filter with τ=330 μs.

FIG. 14 shows an oscilloscope measurement of input voltage 602 and filtered voltage 604 with voltage levels measured to illustrate changes in the voltage applied to DNA before and after filtering. RC Low-Pass filter with τ=330ρs. FIG. 14 also illustrates that these RC values reduce the range of $V_{out}$ to 0.14 V-0.084 V. This configuration gives the same DMM measurement of $V_{out}$=0.1V as the previous RC filter but with a smaller $V_{out}$ variation. The RC filter acts as a Digital-to-Analogue converter (DAC) to the PWM signal generating a $V_{out}$ of 0.1V. Filtering reduces the peak voltage experienced by the graphene FET to 0.14V instead of the original 3.3V. Resistivity of nucleic acid attached graphene FET is measured and illustrated in FIG. 11. The results suggest that in the aqueous electrolyte system, nucleic acid attached to the graphene surface is stable from detachment.

Evaluation of Measurement System

The FRDM-KL25Z microcontroller board provides five analogue-to-digital converters (ADC) to measure analogue signals. The board can only measure voltages; therefore, requiring currents to be converted into voltage signals before it can be measured. In some embodiments, currents over a range of voltage values can be recorded to examine the resistance of graphene FETs. Current values can be converted to voltage levels by using a 1 kΩ pull-up resistor between the graphene FET and ground. They can be then obtained by measuring the voltage across the resistor and converting it to current values using ohm's law. These results can be then plotted on an I-V graph with the gradient of the trend line representing resistance of the entire circuit. The use of a trend line rejects measurement noise and reduces the impact of anomalous data points.

$$\text{Estimated measurement} = \frac{\text{Device measurement}}{E(\text{Noise})} \quad \text{Eq. (10)}$$

Simulation can be conducted using 2000-6000Ω resistance values. The values follow a Gaussian distributed to simulate measurements from human populations. In some embodiments, noise of −2.2% to 10.91% can be added to these resistances. Measurement noise is assumed to be uniformly distributed.

TABLE 2

Resistance values measured by device and specialized equipment and changes in estimated measurement noise

| Data Points | 1 | 2 | 3 | 4 | 5 | 6 | 7 | 8 | 9 |
|---|---|---|---|---|---|---|---|---|---|
| Device(Ω) | 3894.4 | 5059.8 | 4775.9 | 3916.9 | 7320 | 3413.2 | 2038.5 | 3644.3 | 5883.4 |
| Accurate(Ω) | 3780 | 4980 | 4850 | 3780 | 7080 | 3210 | 1850 | 3440 | 5800 |
| Noise | 1.0303 | 1.0160 | 0.9847 | 1.0362 | 1.0339 | 1.0633 | 1.1019 | 1.0594 | 1.0144 |
| E(Noise) | 1.0303 | 1.0231 | 1.0103 | 1.0168 | 1.0202 | 1.0274 | 1.0380 | 1.0407 | 1.0378 |

Figure 15:
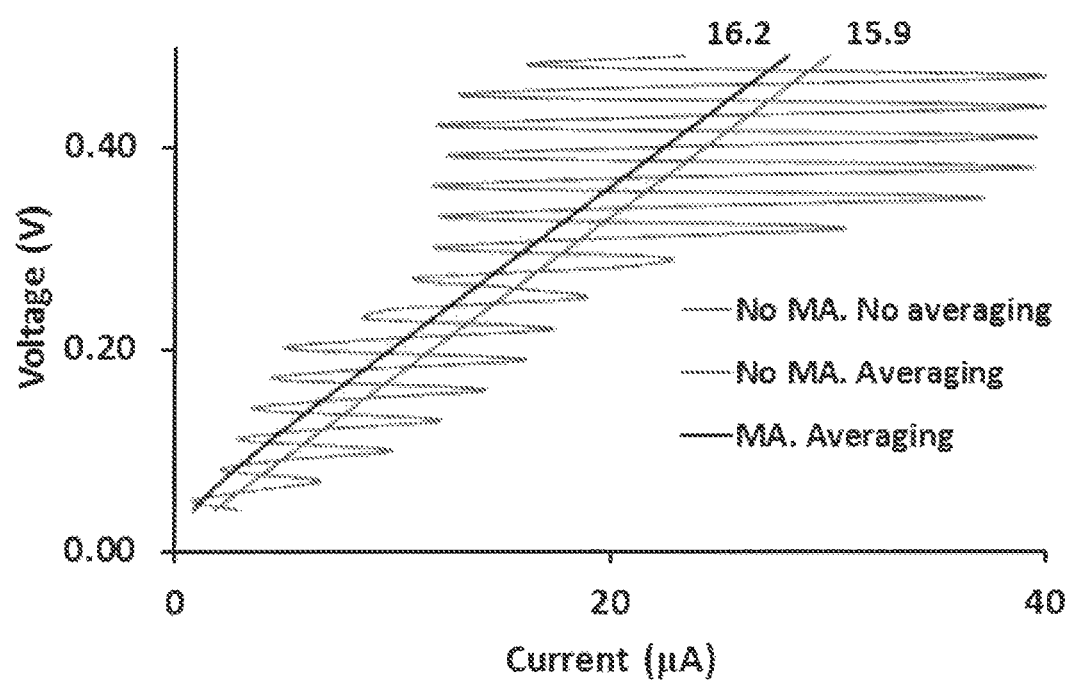
FIG. 15 shows an example of I-V curve of 5 k resistor measured by the device before and after applying the various filtering techniques, averaging of 10000 samples taken and a $2^{nd}$ order Moving-Average filter. Filtering techniques show huge improvements in measurement accuracy. Final device design has both averaging and the Moving-Average filter implemented. Gradient of the trend line of the data points corresponds to resistance. Device measured a total resistance of 0.0162 MΩ and 0.0159 MΩ. Removing the resistance contributions from the low-pass filter and sense resistor gives a measured resistance of 5.2 kΩ and 4.9 kΩ respectively. Numbers above lines represent resistance in kΩ.

In addition, to reduce noise in the voltage measurement by the FRDM-KL25Z microcontroller board, in some embodiments, every data point was taken as an average over 10000 samples measured. FIG. 15 shows the improvement from signal averaging. FIG. 15 shows an I-V curve of 5 k resistor measured by the device before and after applying the various filtering techniques, averaging of 10000 samples taken and a 2nd order Moving-Average filter. Numbers above lines represent resistance in kΩ. Filtering techniques show huge improvements in measurement accuracy. Final device design has both averaging and the Moving-Average filter implemented. Gradient of the trend line of the data points corresponds to resistance. Device measured a total resistance of 0.0162 MΩ and 0.0159 MΩ. Removing the resistance contributions from the low-pass filter and sense resistor gives a measured resistance of 5.2 kΩ and 4.9 kΩ respectively. Measured values vary drastically when no averaging was done with almost no information to be extracted from the measured values. To further improve measurement accuracy, a 2nd order moving average filter can be implemented as:

$$V(t) = \frac{[V(t) + V(t-1) + V(t-2)]}{3} \quad \text{Eq. (7)}$$

This filtering further improves measured values, filtering minor measurement inaccuracies (+0.35%).

Post Measurement Processing

The Root Mean Squared Error (RMSE) can be used as the measure of accuracy, with smaller RMSE values corresponding to better accuracy. The operation of the algorithm is simulated using 25 accurate measurements made through the course of this research.

$$\text{Noise} = \frac{\text{Device measurement}}{\text{Accurate measurement}} \quad \text{Eq. (8)}$$

$$E(\text{Noise})_{new} = \frac{[(E(\text{Noise})_{previous} * (\text{Data Points} - 1)) + \text{Noise}]}{\text{Data Points}} \quad \text{Eq. (9)}$$

Noise is then removed from device measurements for the next 1000 measurements.

Figure 16:
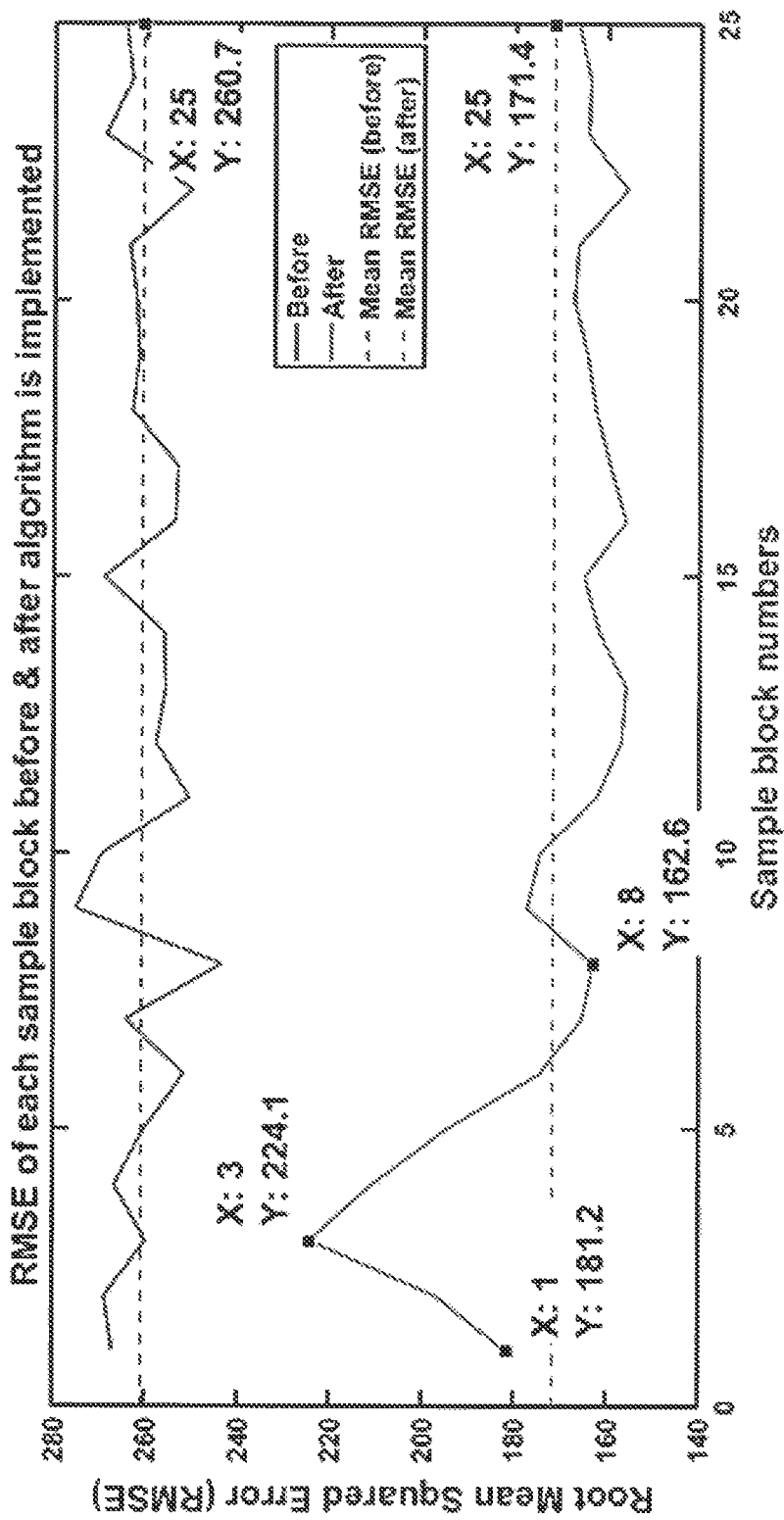
FIG. 16 shows an example of a plot comparing RMSE of 1000-sample blocks before and after implementation of algorithm to minimize noise.

FIG. 16 shows a plot comparing RMSE of 1000-sample blocks before and after implementation of algorithm to minimize noise. From FIG. 16, data with no processing done shows an average RMSE of 260.7 while average RMSE of processed data is 171.4 giving a 34.25% improvement in accuracy. By nature of this algorithm, more accurate data points result in increased accuracy for each 1000-sample blocks. This is because more accurate data points allow better modelling of the measurement noise levels to be removed from device measurements. This is evident in FIG. 16 where RMSE for the first few blocks are relatively high and fluctuates drastically. As the number of accurate data points increases to 11, RMSE values start to decrease and stabilize.

Figure 17:
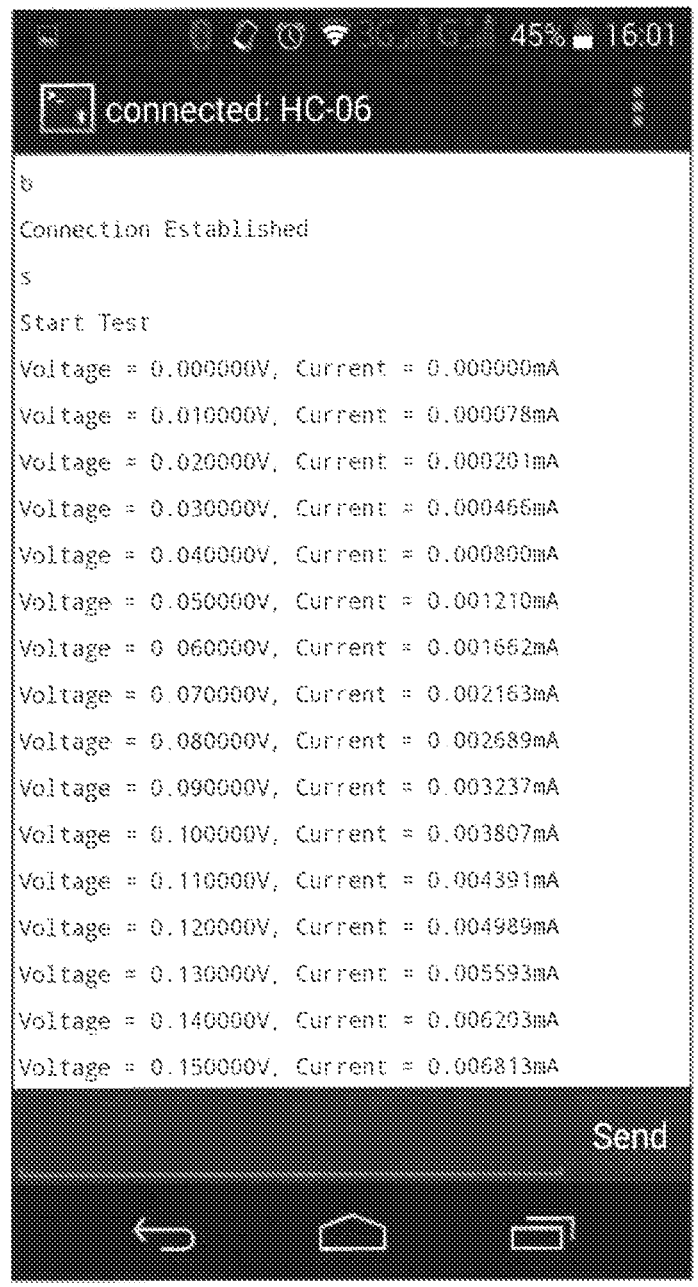
FIG. 17 shows an example of a screenshot of Bluetooth terminal showing data received by the Smartphone during a test demonstrating communication between device and phone.

Using the wireless setup, the data can be transferred to both personal computer and smartphone. The examples of the screenshots are shown in FIG. 10 and FIG. 17. Electrical detection of biomolecule can substitute the fluorescence-based microarray, which would lead to better accessibility to patients. It also can contribute to end-user-friendly platforms such as wearable or implantable biosensor. For those purpose, enhancement of specificity and wireless communication capability disclosed herein are needed. As such, the development and implementation of the technology would allow more affordable and accurate diagnosis of diseases including cancer and degenerative, genetic, and other various disorders.

DNA Sensing Data Analysis

The binding of the nucleic acid probe is observed by an increase in the resistivity of the graphene FET. In some embodiments, to test the operation of specific DNA detection, target DNA, which is the complementary strand to probe DNA, can be added in increasing concentrations. Decreased levels of resistivity indicates binding of the two DNA strands causing them to detach from the graphene surface. Higher concentrations of target DNA results in a greater decrease in resistivity implying more DNA strands binding together, detaching from the graphene surface in the process. This phenomenon demonstrates the ability of this device to detect DNA and offers a possible method to detect specific DNA sequences by using appropriate probe DNA sequences. FIG. 18 shows three sets of tests conducted to verify this observation. Resistance changes depending on various experimental conditions. FIG. 18A shows an example of raw data set of resistance change induced by DNA. FIG. 18B shows statistical data of resistance changes due to DNA detection, wherein R0 is resistance of the pristine graphene. Complementary target DNA hybridizes with probe, leaving the surface of graphene; thus the resistance is decreased. On the other hand, non-complementary DNA does not decrease the resistance. FIG. 18C shows normalized resistance demonstrating clear discrimination between complementary and non-complementary target strands. R2 is resistance of non-complementary and R1 is of complementary. All three sets of data show the same trend in resistance changes, confirming the validity and reliability of the data. In the control experiment, non-complementary sequence can be used as the target DNA. In contrast to complementary target DNA strands, non-complementary DNA strands do not hybridize with probe DNA strands, leaving probe DNA strands attached to the graphene surface. The normalized resistance shown in FIG. 18C is calculated by:

$$R_{normalized} = \frac{\frac{R_{non-complementary}}{R_{probe}} - \frac{R_{complementary}}{R_{probe}}}{\frac{R_{complementary}}{R_{probe}}} \quad \text{Eq. (8)}$$

where $R_{non-complementary}$ and $R_{complementary}$ are the resistance values with non-complementary and complementary target DNA for each of the experimental conditions and Rprobe is the maximum resistance when probe DNA is treated on the sensor.

Implementation of the Disclosed Technology

The disclosed and other embodiments and the functional operations described in this document, such as measurements, data collection, and data processing, can be implemented in digital electronic circuitry, or in computer software, firmware, or hardware, including the structures disclosed in this document and their structural equivalents, or in combinations of one or more of them. The relevant operations for the disclosed and other embodiments can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Example Applications of the Disclosed Technology and Devices

The disclosed technology and nano-sensor devices have a number of applications including microarrays; biomolecular sensors for in vitro and in vivo uses; implantable biosensors for continuing real time monitoring of biomolecules in the body of humans or animals; digital biosensors; wireless biosensors; and nanobiosensors. Specifically, the disclosed technology enables, in one useful aspect, a cheaper, faster and portable nucleic acid sensing technique and device for detecting nucleic acid damage or mutation in early stages for global health management.

WORKING EXAMPLES

The following examples illustrate various embodiments of the technology disclosed in this document. By no means the following examples limit the scope of the invention in any way.

Nano-Sensors for Visual-Based Detection

Example 1 Materials and Method

Chemicals and buffer solutions were obtained from Sigma Aldrich (Saint Louis, Mo.). All DNA constructs were obtained from IDT (Coralville, Iowa). DNA ladders were from Promega (Madison, Wis.). DNA gels were from Lonza (Walkersville, Md.). Nano-gold particles were from BBI (UK). TEM grids were from Ted Pella (Redding, Calif.). All the DNA sequences used appear in Table 3 below.

TABLE 3

| | Sequences of the DNA Nano-Devices | SEQ ID NO: |
|---|---|---|
| L | 5'-GCC ATA GTT AGA GCA TGC GCC ATA GTI ITT TTI TTT ITT ITT IIT TTI ITT TIT TIT IIT TIT ITC CCT TCC GAA TGC AGC TGC CAT TCC GAA TGC-3' | 18 |
| R | 5'-CGC AAT CCA CCG ATC ATC CGC AAT CCA AAT CTC CCA ACC ACA ACA AAC CAA ACC AAC AAC AAA CAA CAC CAC TAT GGC GCA TGC TCT AAC TAT GGC-3' | 19 |
| F | 5'-GGT GTT GTT TGT TGT TGG TTT GGT TTG TTG TGG TTT TTA GAT TTG GAT TGA AGT GAG CGT-3' | 20 |
| C | 5'-ACG CTC ACT TAA ATC TAA AAA CCA CAA CAA ACC AAA CCA ACA ACA AAC-3' | 21 |
| T | 5'-AAG GGA CCC AAC CAC AA-3' | 22 |
| T-SH | 5'-/5ThioMC6-D/ttt ttt AAG GGA CCC AAC CAC AA-3' | 23 |
| T-FQ | 5'-/FAM Q/ttt ttt AA GGA CCC AAC CAC AA-3' | 24 |
| A1 | 5'-CGG ATG ATC GGT GGA TTG CG-3' | 25 |
| A2 | 5'-GCA TTC GGA ATG GCA GCT GCA TTC-3' | 26 |
| A2-FAM | 5'-GCA TTC GGA ATG GCA GCT GCA TTC ttt/FAM/-3' | 27 |
| A1-SH | 5'-CGG ATG ATC GGT GGA TTG CG ttt/3ThioMC3-D/-3' | 28 |
| A2-SH | 5'-/5ThioMC6-D/tGCA TTC GGA ATG GCA GCT GCA TTC-3' | 29 |
| L | 5'-GCC ATA GTT AGA GCA TGC GCC ATA GTI ITI TTI TTT ITT ITT IIT TTI ITT TIT TIT IIT TII ITC CCT TCC GAA TGC AGC TGC CAT TCC GAA TGC-3' | 18 |
| R | 5'-CGC AAT CCA CCG ATC ATC CGC AAT CCA AAT CTC CCA ACC ACA ACA AAC CAA ACC AAC AAC AAA CAA CAC CAC TAT GGC GCA TGC TCT AAC TAT GGC-3' | 19 |
| F | 5'-GGT GTT GTT TGT TGT TGG TTT GGT TTG TTG TGG TTT TTA GAT TTG GAT TGA AGT GAG CGT-3' | 20 |
| F-no mismatch | 5'-GGT GTT GTT TGT TGT TGG TTT GGT TTG TTG TGG TTG GGA GAT TTG GAT TGA AGT GAG CGT-3' | 30 |
| F-6 mismatches | 5'-GGT GTT GTT TGT TGT TGG TTT GGT TTG TT ATA ATT AAA AGA TTT G GAT TGA AGT GAG CGT-3' | 31 |
| F-12 mismatches | 5'-GGT GTT GTT TGT TAT TAA TTT AAT TTA TT ATA ATT AAA AGA TTT G GAT TGA AGT GAG CGT-3' | 32 |
| AF | 5'-ACG CTC ACT TCA ATC CAA ATC TAA AAA CCA CAA CAA ACC AAA CCA ACA ACA A-3' | 33 |
| T | 5'-AAG GGA CCC AAC CAC AA-3' | 22 |
| T-SH | 5'-/5ThioMC6-D/TTT TTT TAA GGG ACC AAC CAA-3' | 34 |
| T-FQ | 5'-/FAM Q/TTT TTT TAA GGG ACC AAC CAA-3' | 35 |
| T-FAM | 5'-/FAM/TTT TTT TAA GGG ACC AAC CAA-3' | 36 |
| A1 | 5'-CGG ATG ATC GGT GGA TTG CG-3' | 25 |
| A2 | 5'-GCA TTC GGA ATG GCA GCT GCA TTC-3' | 26 |
| A2-FAM | 5'-GCA TTC GGA ATG GCA GCT GCA TTC GGT/FAM/-3' | 37 |
| A1-SH | 5'-CGG ATG ATC GGT GGA TTG CG TTT/3ThioMC3-D/-3' | 28 |
| A2-SH | 5'-/5ThioMC6-D/TGC ATT CGG AAT GGC AGC TGC ATT C-3' | 29 |

Device Description of DNA Capture and Release

In some embodiments, disclosed herein is a DNA device that captures and releases a specific DNA strand repeatedly, named "Capture and Release device" (CR device). The operation of the carrier depends upon mismatches between strands. Given that hybridization energy depends on strand length and temperature, the reaction between different strands can be precisely manipulated. By controlling the number of mismatches and hybridization length, the disclosed DNA device allows repeated capture and release of the same DNA strands while simultaneously being sensitive to nucleotide mismatches.

Figure 19:
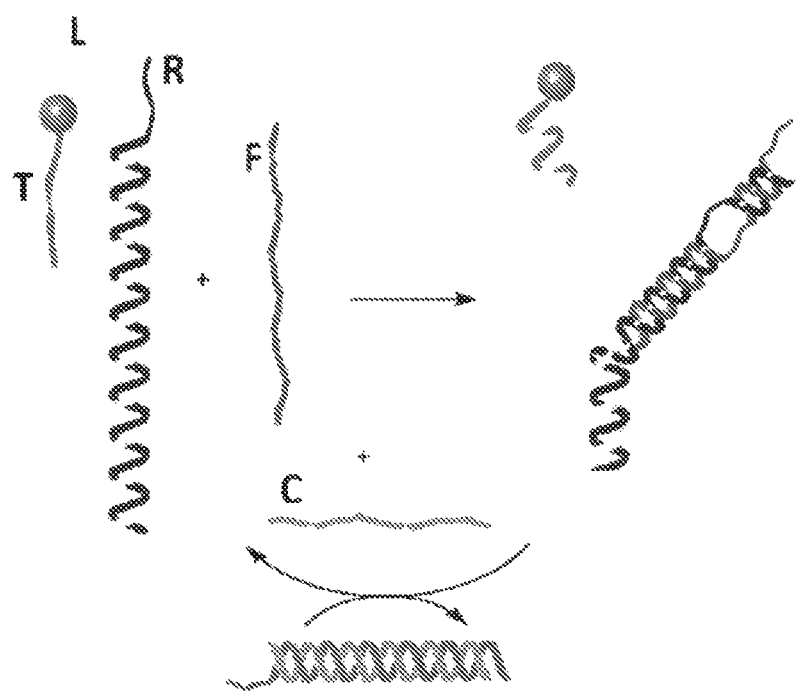
FIG. 19 illustrates an example of a design of a self-sustaining continually cycling capture-and-release DNA nano-device for modelling and mechanistic analysis of DNA double helix nano-dynamics in accordance with some embodiments described herein.
Figure 20:
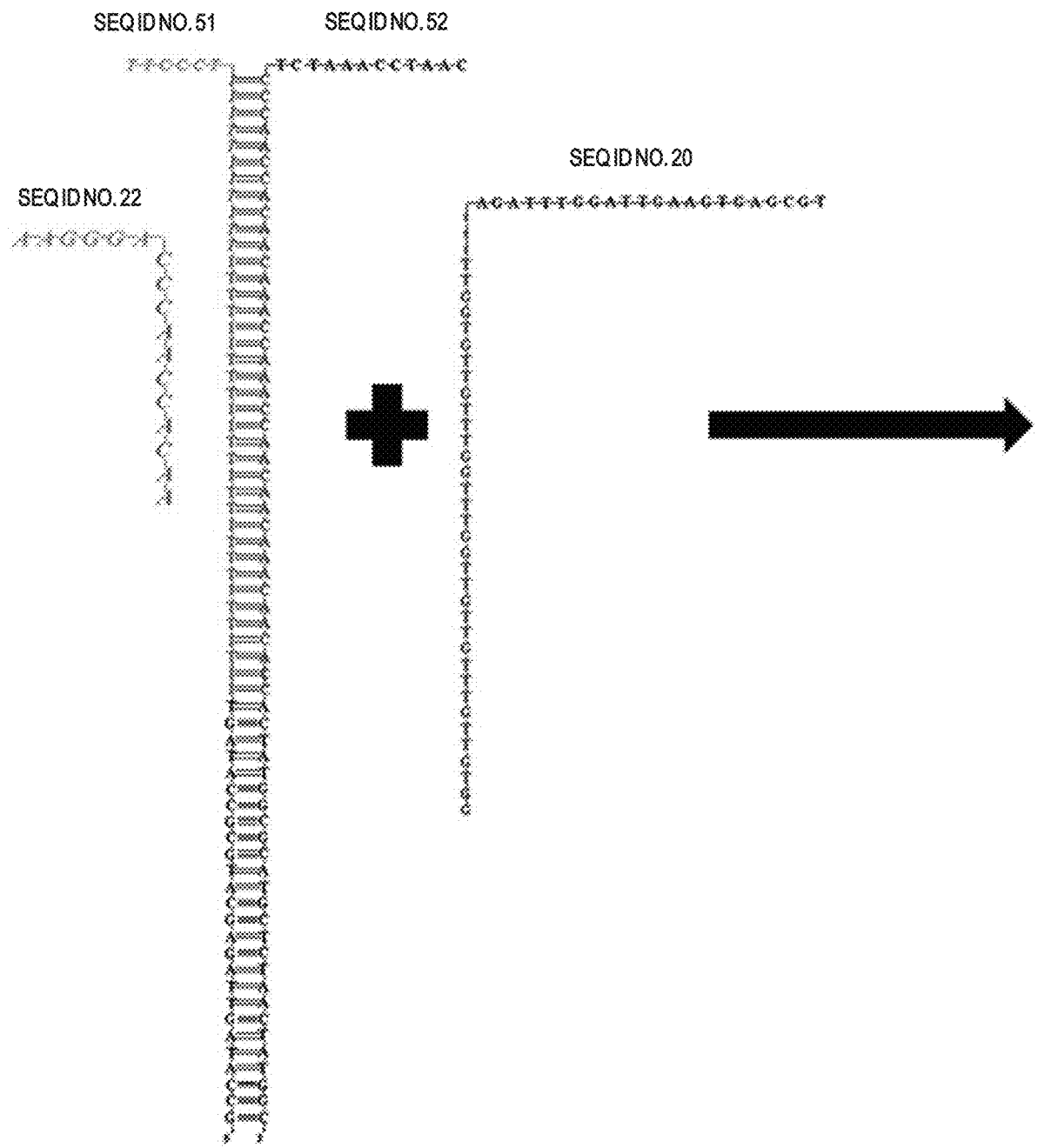
FIG. 20 shows the specific sequences and schematic of the DNA strands used in an example capture and release device.
Figure 20:
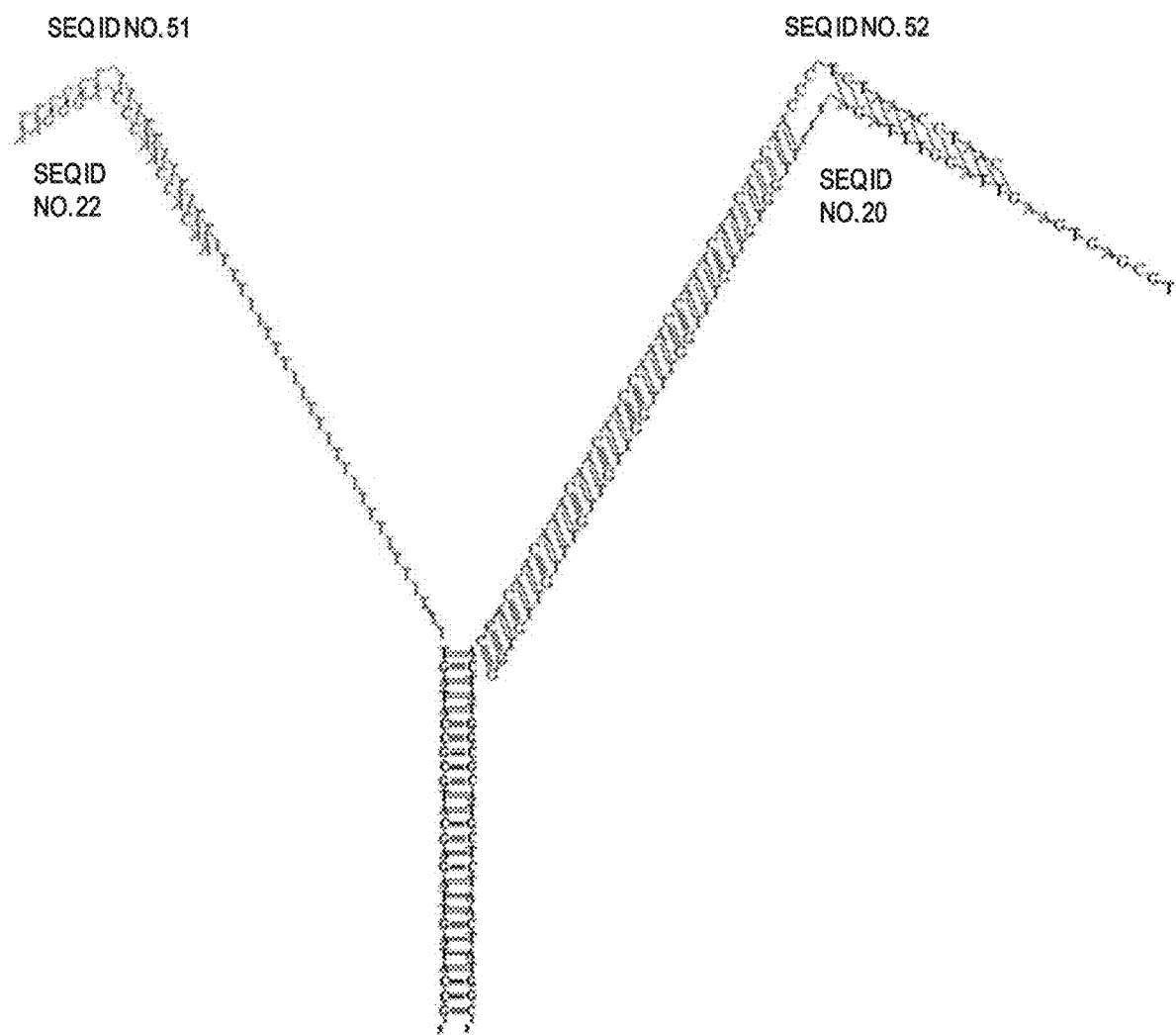
Figure 20:
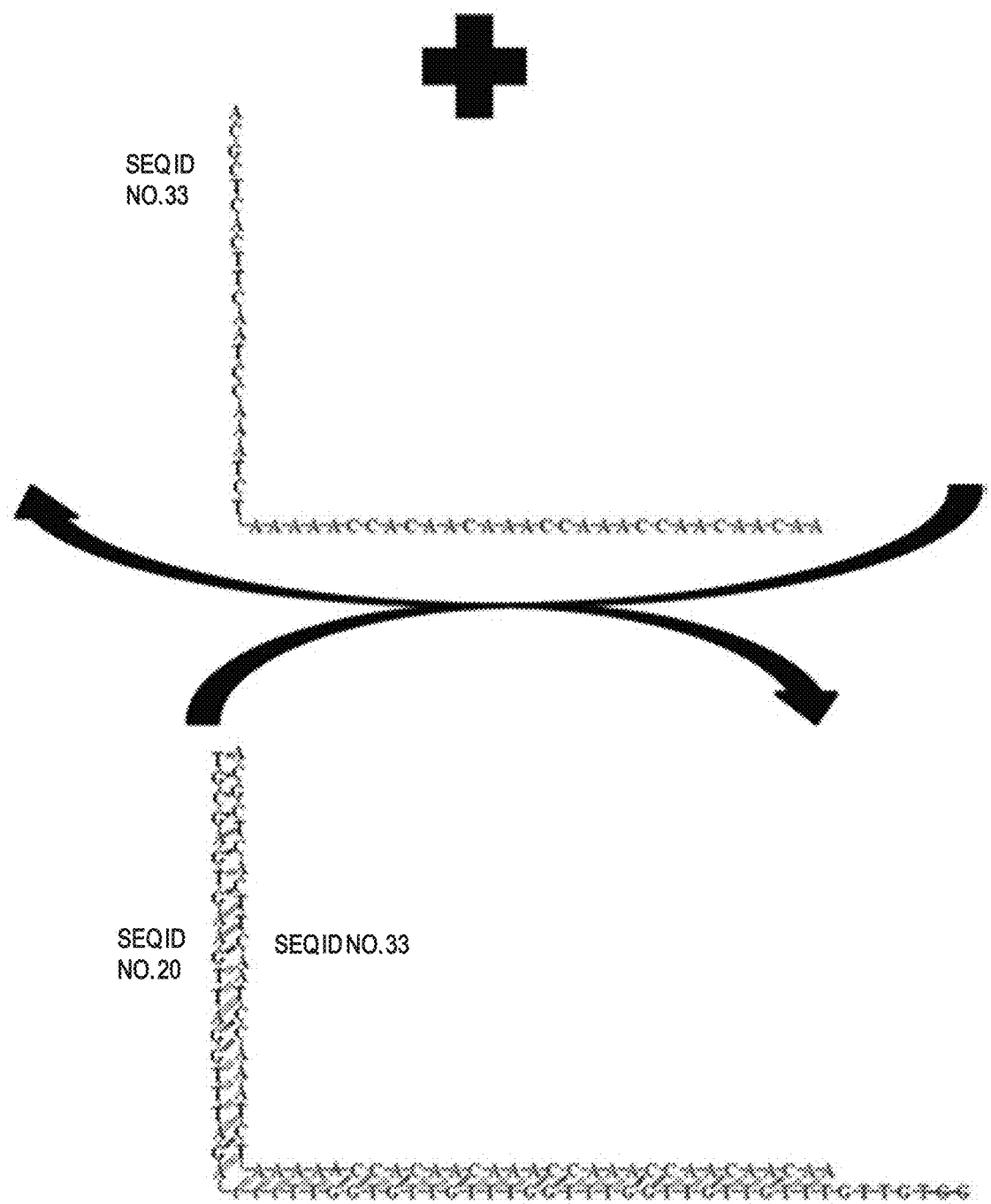

In some embodiments, the device consists of three parts, a right side (R), a left side (L) and a targeted capture and release strand (T). R and L are complimentary to one another (FIGS. 19 and 20). T is complimentary to part of L, however, it does not possess enough energy to displace R and hybridize to L spontaneously due to controlled mismatches. At the initial state, R and L are hybridized and T is floating freely in the same system. The fuel strand (F) is complimentary to part of R and partially displaces L when it hybridizes with R, after it is introduced to the system. After addition of F, R and L remain partially bound together in a hinge region, to keep the device intact. The R and L strands with a hinge are called "tweezers". The introduction of F allows the displaced portion of L to freely hybridize to T, which is already present in the system. The anti-fuel strand (AF) neutralizes F as they are complimentary. Removal of F results in R and L re-hybridizing evicting T from its hybridization state, such that it again enters a single stranded state. Accordingly, the device captures T when F is introduced, and releases it when AF is present. One full cycle of F and AF addition returns the device and T to their initial states. F-AF pairs are waste byproducts of each cycle. A fluorescence probe can be tagged to L and a fluorescence quencher can be attached to T and the activity is monitored in the spectrometer. Moreover, to demonstrate its mechanical application, Gold nanoparticles (AuNPs) can be attached to tweezers and T.

Figure 22:
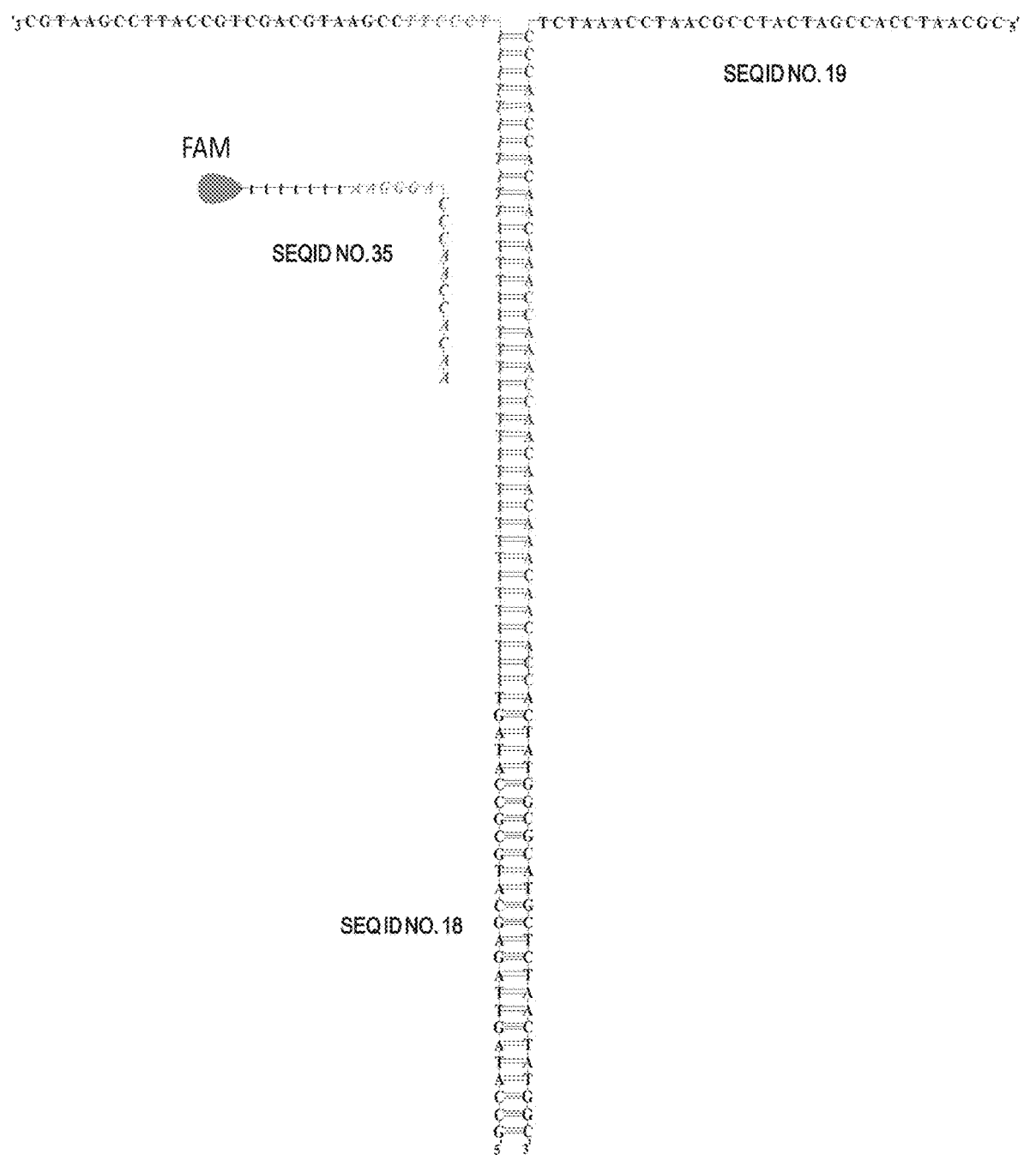
Figure 23:
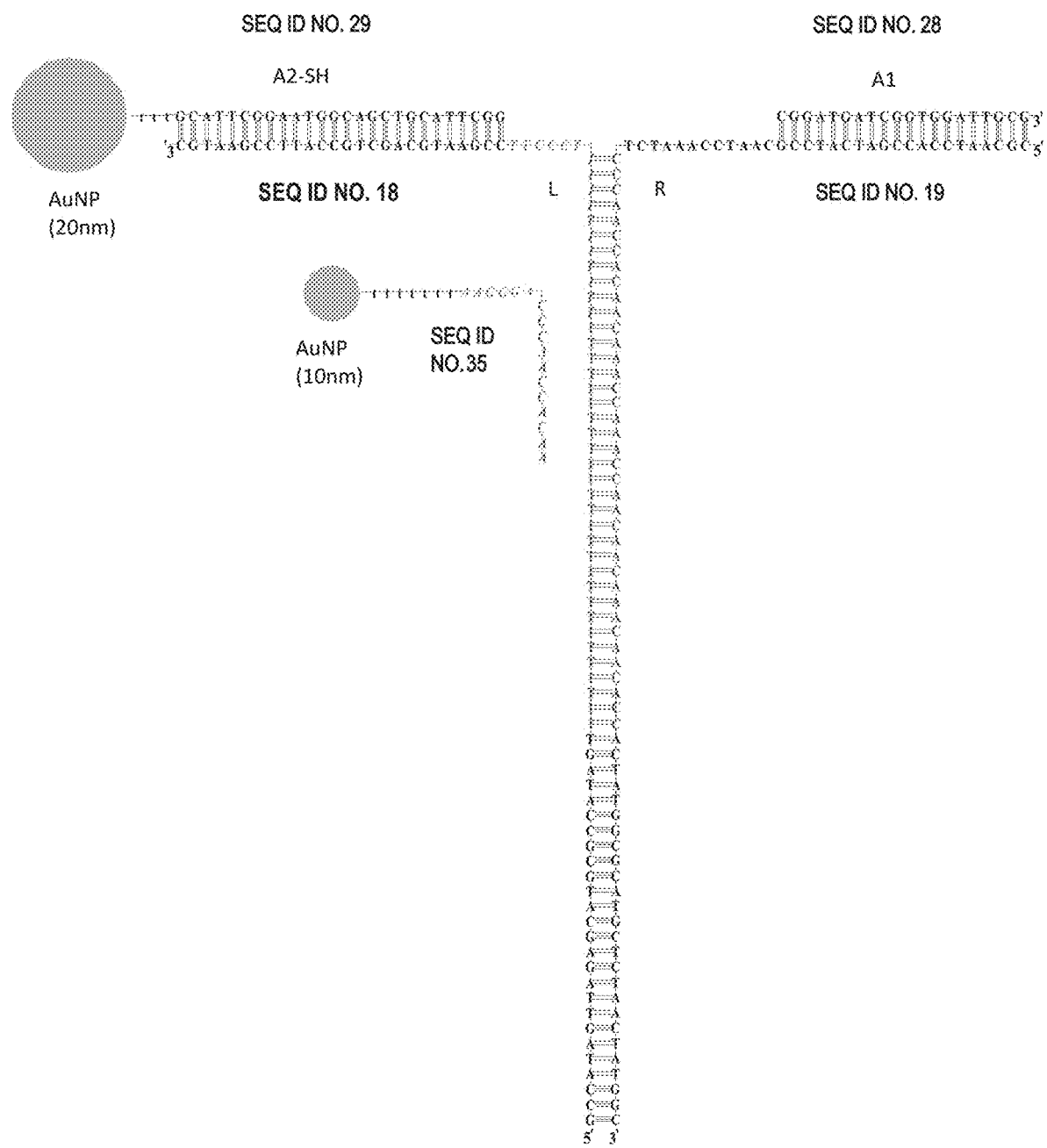
FIG. 23 shows an example schematic of the DNA attachment to the AuNP used in the TEM experiments.
Figure 23:
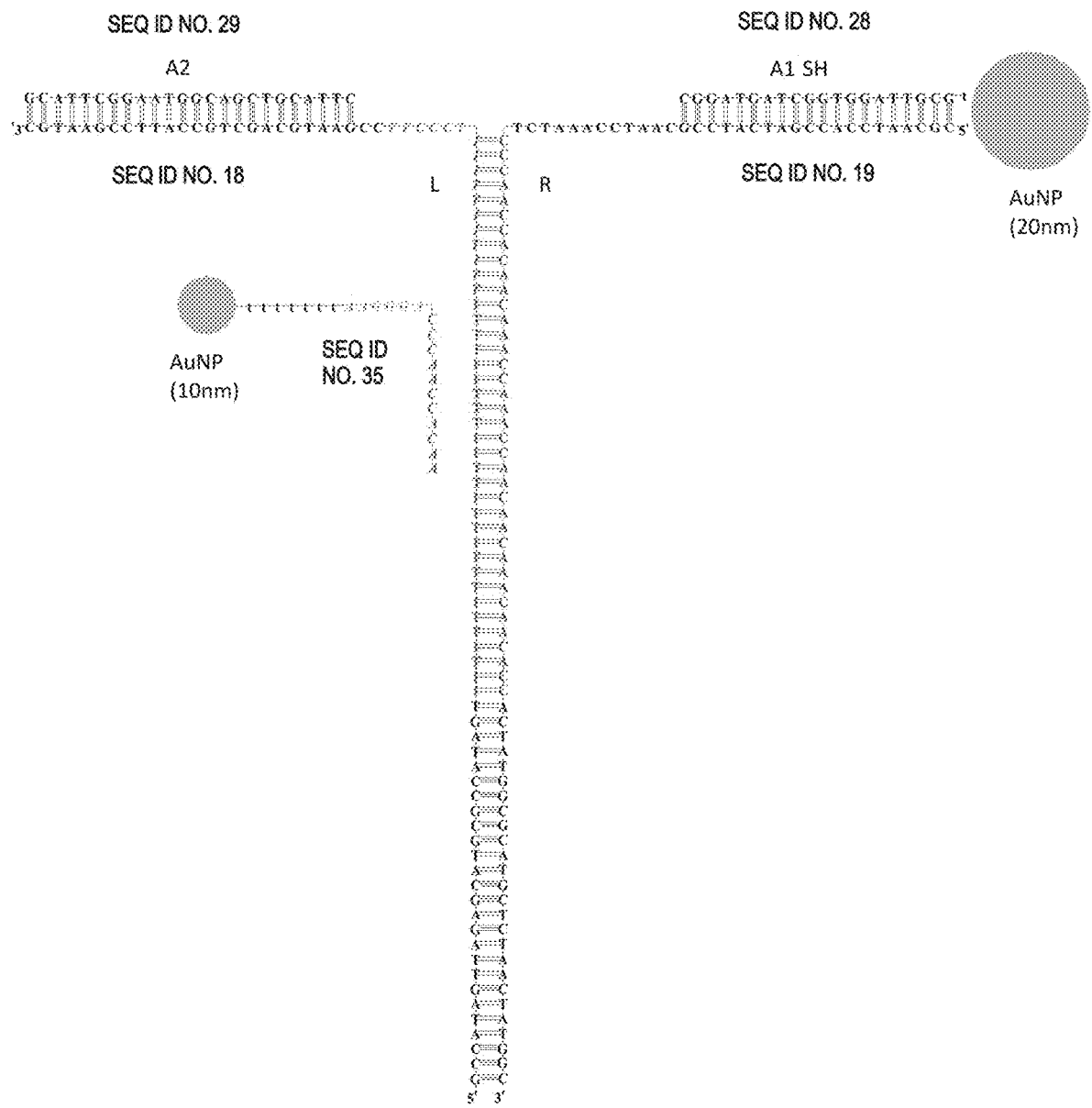

In one example, R and L had 90 nucleotides (nt), which were complimentary to each other over the entire length. R and L had additional toeholds of 10 nt (5' end for R) and 6 nt (3' end for L), respectively. Thus, the total length for R and L were 100 nt and 96 nt. 26 nt bound R and L, and 20 nt and 24 nt of extended arm parts existed at the end of R and L from toeholds, respectively. In another example, R and L had 64 nucleotides (nt), which were complimentary to each other over the entire length. R and L had additional toeholds of 12 nt (5' end for R) and 6 nt (3' end for L), respectively. Thus, the total length were 76 nt and 70 nt. Among the 64 nt that were complimentary between R and L, 26 nt formed the hinge binding R and L at all times. Extensions were added on to the toehold for binding of fluorophore or thiol containing strands. See FIGS. 21-23.

The toeholds were not complimentary to each other to allow for operation of the device. T was 17 nt and complimentary to L such that it was complimentary over the 6 nt of the toehold on L. The device was designed such that the short 6 nt toehold on the L strand had too weak an affinity for the T strand when at a controlled temperature and concentration. This limited hybridization of T and L when L was hybridized to R. F had 60 nt and two toeholds, one was complimentary to a toehold of R, and the other one was complimentary to a toehold for AF, the anti-fueling strand. AF was 54 nt and 12 nt were a toehold for F strand. Alternatively, AF was 52 nt and 10 nt were a toehold for F strand. Theoretically, F should be complimentary to T and AF should be complimentary to L. Interactions between these strands could disrupt the desirable operation of the device. To prevent these undesirable interactions, F had 3 consecutive nt of mismatch to R and T, which was 36-38 nt from 5' end of F (FIG. 20). This mismatch reduced affinity between F and T significantly, while still maintaining affinity between F and R. This allowed only 6 nt, 7 nt or 8 nt to be consecutively complimentary between F and T, lessening the hybridization energy. R had 10 or 12 nt and 35 nt of complimentary portion with F, including 3 nt of mismatched sequence between R and F. To reduce another interruption from AF and L, 6 nt or 8 nt sequence of AF was truncated from the end of the strands to decrease the total energy. Also, substitution of deoxyinosine for deoxyguanine on L, lessened the interaction energy between AF and L compared to the energy between F and AF. Specific configuration of the device with base pairings is illustrated in FIG. 20. The overall operation can be summarized as: [L:R]+T+F→[R:F, L:T] (capturing), [R:F,L:T]+AF→[L:R]+T+[F:AF] (releasing).

Fluorescence Observation of Device Activity

Figure 21:
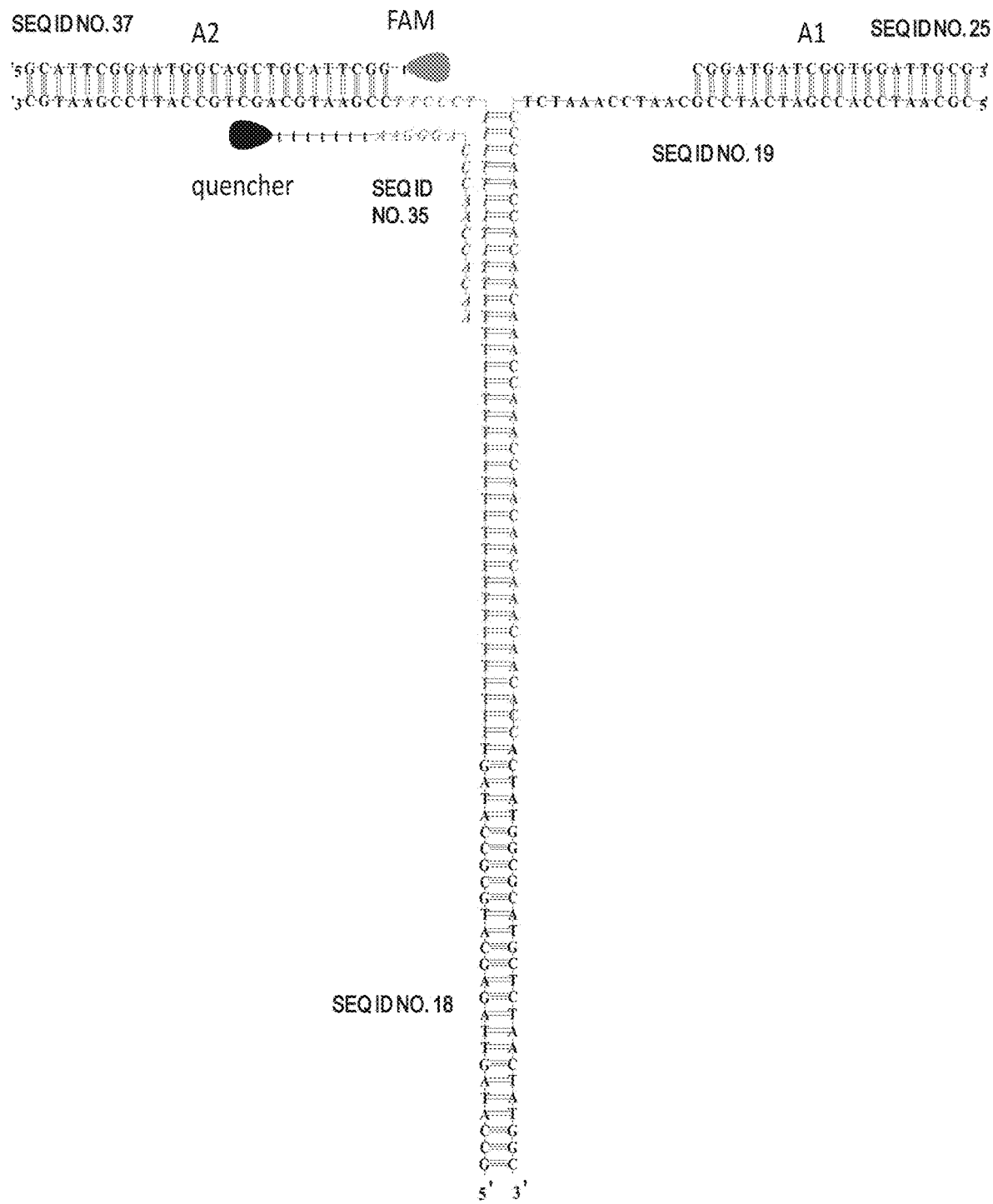
FIG. 21 shows an example schematic of the DNA strands used for the fluorescence experiments.

Operation of the device was monitored over time by fluorescent probes. Fluorescent probes were tagged to L, while a fluorescence quencher was attached to T (FIG. 21). Upon hybridization, quenching of the probe was achieved. Measurements were visualized using a Tecan Infinite 200 M plate reading spectrometer (San Jose, Calif.). Excitation/Emission of FAM were observed at 495/520 nm. Each experiment began with a 50 µl sample volume with a device concentration of 250 nM in black 96 well plates. Alternatively, the device concentration was 150 nM (e.g., 150 nM of tweezers and 450 nM of T). Clear microplate sealing films were applied over the sample wells to avoid evaporation. Experiments were conducted on DNA samples, which were dissolved in nuclease free reaction buffer (30 mM Tris-HCL, 160 mM NaCl, pH 8.0). Capturing and releasing were dependent upon temperature and concentration, thus experiments were conducted at 27° C., 35° C. and 40° C. with 250 nM of samples. Measurements were also done with 60 nM, 250 nM and 1 µM at 35° C. With an optimal condition from those variations, 3 cycles of consecutive operations were observed. Basal fluorescence of each sample was measured before running. F was added to sample walls at concentration of 4 times of the device for the first capture of T. AF was added at 8 times of the device for releasing. F and AF would neutralize each leaving excess AF to float freely in the sample. For successive openings of the tweezers, F was added to the same sample walls 8 times of the devices to bind the remaining C. All measurements were normalized by dividing by the basal (unquenched) fluorescence level.

Transmission Electron Microscopy of Capturing and Releasing

Figure 24:
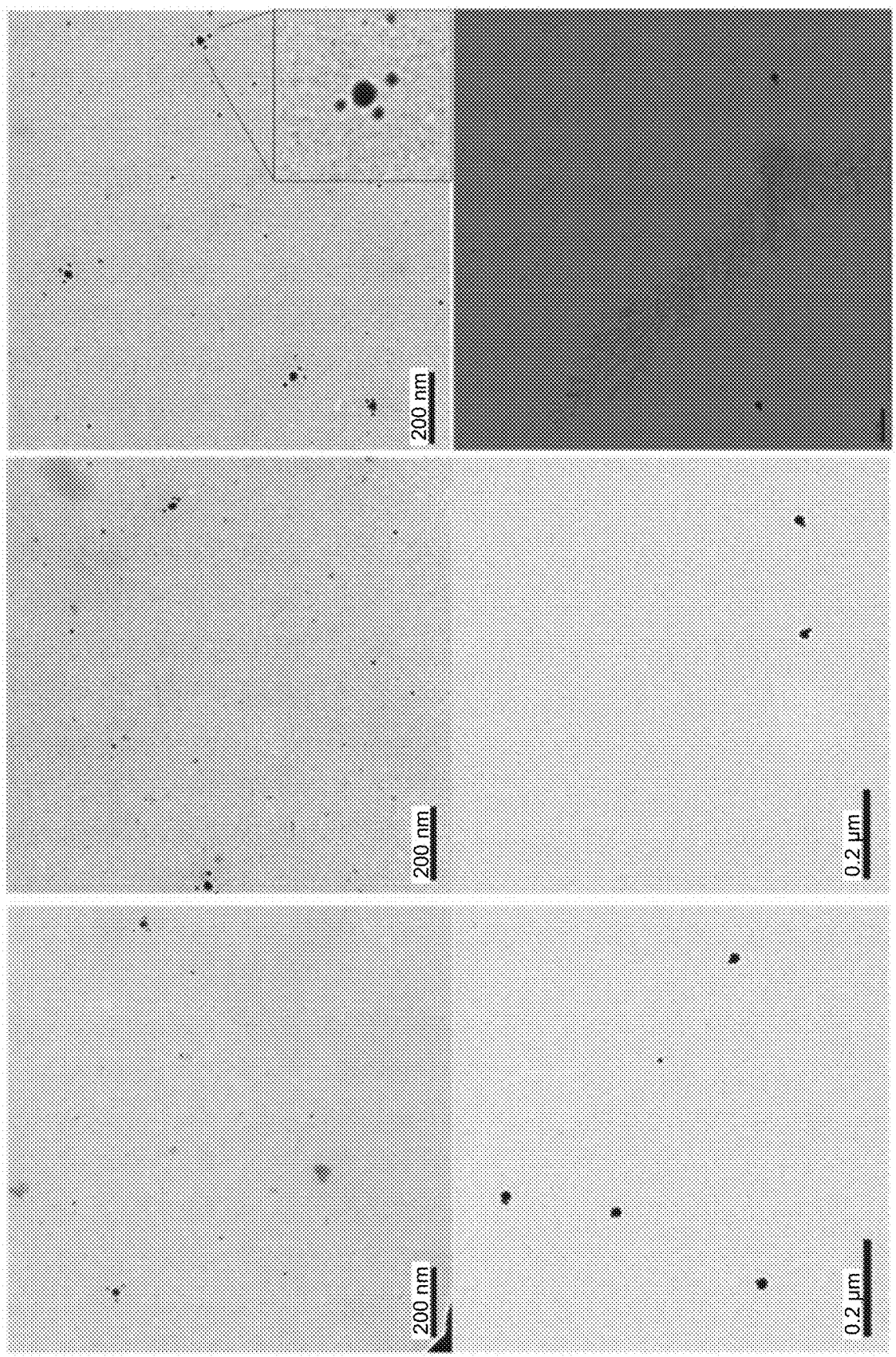
FIG. 24 shows additional TEM images of AuNP functionalized devices. The ratios of the tweezers and the AuNPs are 3:1 for the top panel and 1:1 for the bottom panel.

Operation of the devices was also seen by transmission electron microscopy (TEM, JEOL 1200 EX II TEM). The DNA sequences were elongated by adding thiol containing arms (A) to R and L, enabling DNA to attach to Gold-nano particle (AuNP [d=10-20 nm]) for TEM visualization. The arm parts for L (A1-SH, Table 3) were 20 nt and for R (A2-SH, Table 3) was 24 nt. Citrate-coating of AuNPs was replaced by phosphine to improve stability in buffer solution. Phosphine (bis(p-sulfonateophenil)phenylphosphine dihydrate dipotassuim salt) was added to AuNPs and gently stirred overnight. AuNP samples were suspended with buffer solution and centrifuged. This was repeated 3 times. The disulfide functional groups were cleaved by addition of tris(2-carboxyethyl)phosphine (TCEP) slurry to samples. After 1 hour of mixture, the cleaved samples were purified using Pierce spin cup paper filter. Freshly cleaved DNA samples were then mixed with the AuNPs samples in different ratios. For 1:1 ratios of device to AuNP, thiol groups were attached to L arms, and for 3:1 ratios, it was done on R side (FIG. 24). After 24 hours, the samples were diluted in buffer and centrifuged 3 times to remove residual DNAs which were not attached to AuNPs. The same protocol was used to attach AuNP to F. AuNP samples and F were mixed at 35° C. with 250 nM or 150 nM devices and 1 µM target strands (or 600 nM fuel strands) and reacted overnight. Samples were pipetted onto carbon film and formvar TEM grids. Excess liquid was wiped with paper wipes after 15 minutes at 35° C. on the hot plate. The images were collected with a JEOL 1200 EX II TEM.

Gel Electrophoresis Analysis of Capturing

Capture and release states were verified by DNA gel electrophoresis. The same extended devices used in the Transmission Electron Microscopy experiments were run on the gel (FIG. 25). The double helix conformation of [L:R] (closed tweezers), [L, R:F] (F-tweezers hybridization) and [L:T, F:R] (capturing state) were created at room temperature. Samples were mixed as described in the fluorescent experiment with 1:1:4 for [L, R:F] and 1:2:4:1 for [L:T, F:R]. Samples were reacted overnight to confirm the maximum data collection. To differentiate two opened bands, the fluorescent probe was labeled only to T. Double helixes were stained by Ethidium Bromide (EtBr) and helixes with T were shown as both EtBr and fluorescence. DNA gel electrophoresis was performed with 4% agarose gel at 5V/cm in TBE buffer and temperature was kept at room temperature. Data were collected from FX-Imager Pro Plus and Quantity One software package (Bio-Rad).

Example 2 a Single Nucleotide Toehold is Sufficient to Markedly Enhance DNA Strand Displacement Kinetics Conventional DNA double helix requires modifications such as single-strand toeholds or replacement of deoxyinosine instead of deoxyguanine to display readily detectable strands' displacement. The effect of toehold lengths on kinetics of strand displacement of DNA nano-devices having sequences that were engineered using either conventional nucleotides or inosine-based DNA double helix designs were analyzed. Activity of the devices was continually monitored and recorded using time-lapse fluorescence detection. Performance of devices was evaluated based on measurements of kinetics of strands' displacement reactions and difference in performance was estimated by calculating the ratios of kinetics' values for each experimental condition.

FIGS. 26A-26D illustrate inosine-based DNA nano-devices representing sensitive and efficient model system for experimental analyses of protein-less DNA double helix dynamics in accordance with some embodiments described herein.

Figure 26A:
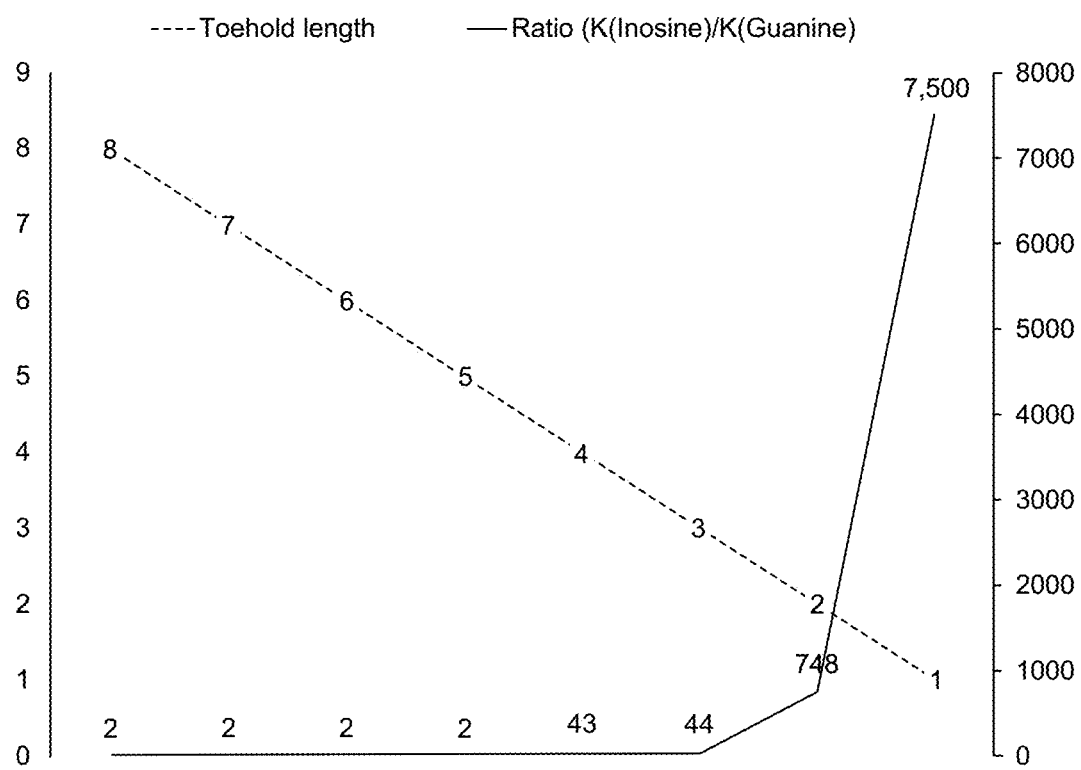
FIGS. 26A-26D illustrate inosine-based DNA nano-devices representing sensitive and efficient model system for experimental analyses of protein-less DNA double helix dynamics in accordance with some embodiments described herein.
Figure 26B:
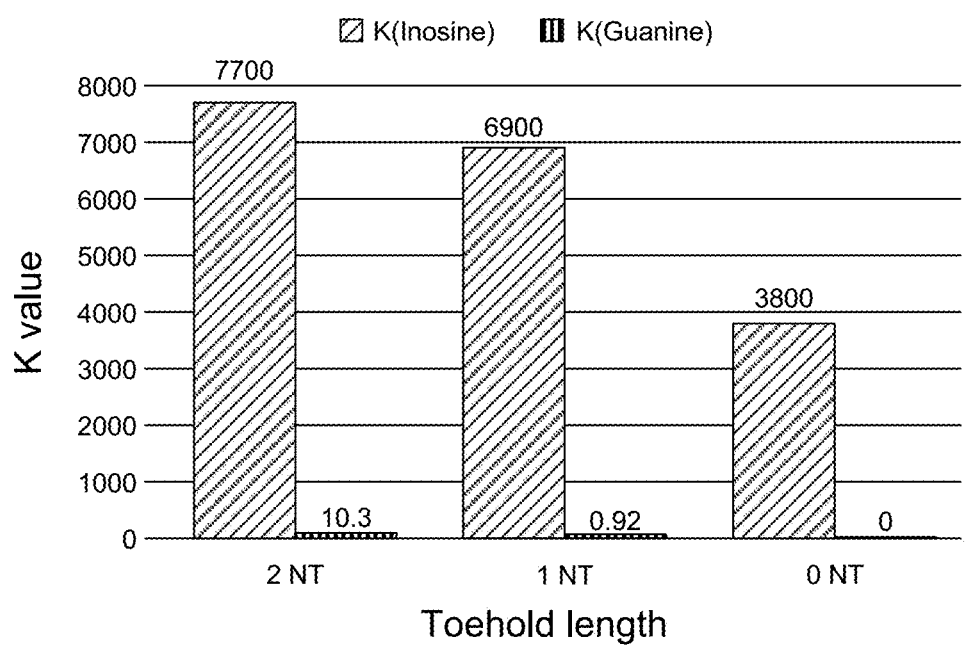
Figure 26C:
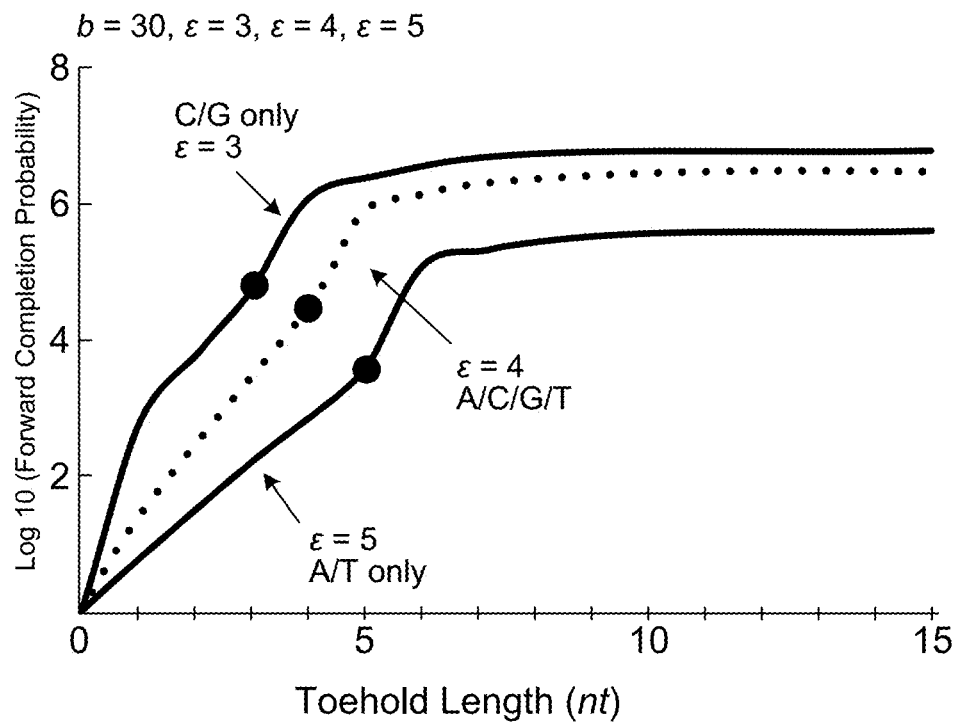
Figure 26D:
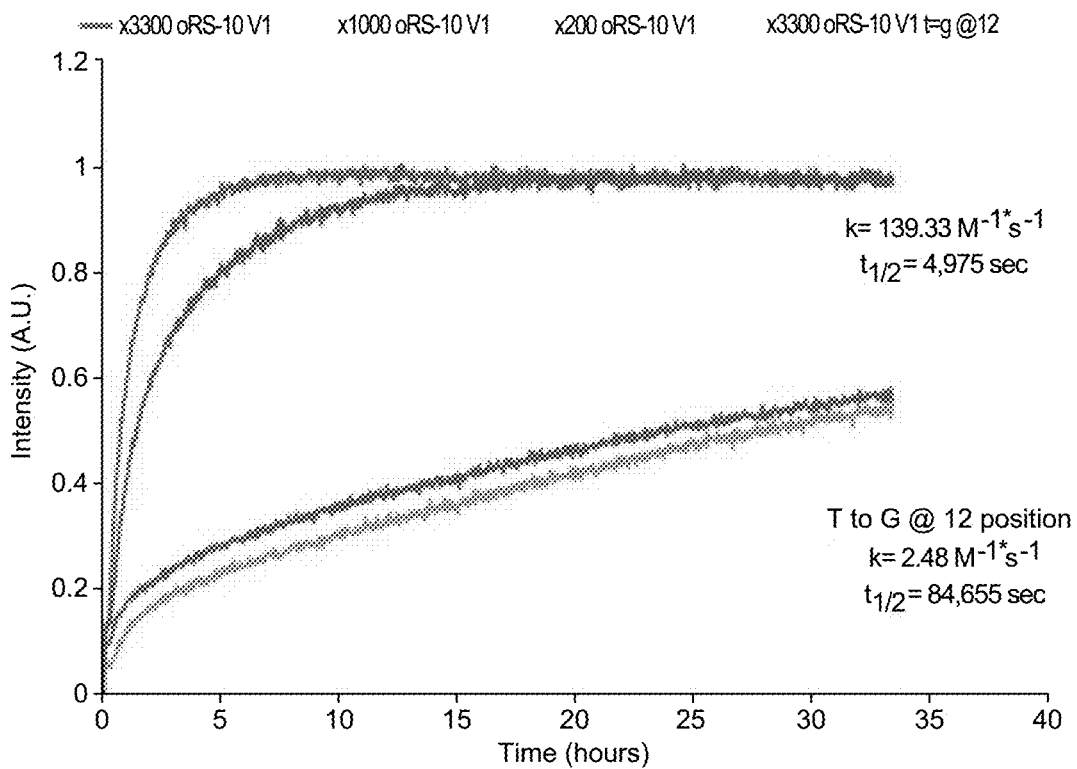

Time-lapse analysis of DNA double helix dynamics based on kinetics of strand displacement reactions revealed a superior performance of inosine-based DNA nano-devices compared to conventional double helix designs and introduction of a single nucleotide toehold further enhances the kinetics of strands' displacement (FIGS. 26A and 26B). Enhanced kinetics of strand displacement reactions of C/G double helix (FIG. 26C) and diminished strand displacement kinetics by invading strands containing a single nucleotide mismatch (FIG. 26D).

Inosine-based devices displayed a superior performance regardless of toehold lengths. Notably, introduction of a single nucleotide toehold into devices was sufficient to enhance the strand displacement kinetics of both inosine-based and conventional DNA double helices. However, inosine-based DNA nano-device harboring a single nucleotide toehold was ~7,500-fold more efficient in sensing invading strands compared to similar devices engineered using the conventional DNA double helix design, as shown in FIGS. 26A-26D. Invading strands containing C/G toehold sequences appeared to induce consistently faster DNA strand displacement reactions compared to the A/T toehold-bearing invading sequences as shown in FIGS. 26A-26D.

These results demonstrate that inosine-based DNA nano-devices represent a superior experimental system for analysis of DNA double helix dynamics compared to conventional double helix designs and introduction of a single nucleotide toehold further enhances the kinetics of strands' displacement.

Table 4 below lists examples of some top performing nano-sensors for detection and discrimination of nucleic acids at a single nucleotide resolution.

TABLE 4

Examples of nano-sensors for detection and discrimination of nucleic acids at a single nucleotide resolution

| Invading strand | Concentration, nM | k (M−1*s−1) | $t_{1/2}$ (sec) | Nano-device sensitivity enhancement factor** |
|---|---|---|---|---|
| Nano-Device: DNA[N]:RNA[w] hybrid RS2-10 (3 nM) | | | | |
| 6 nt toehold | | | | |
| oRNA + 6 | 20 nM | 180507 | 192 | 90254 |
|  | 100 nM | 173287 | 40 | 86643 |
| oDNA + 6 | 20 nM | 132280 | 262 | 1895.1 |
|  | 100 nM | 133298 | 52 | 1909.7 |
| No toehold | | | | |
| oRNA | 500 nM | 4881 | 284 | 2440.5 |
|  | 1000 nM | 4951.1 | 140 | 2475.6 |
| oDNA | 500 nM | 6134 | 226 | 87.88 |
|  | 1000 nM | 6027.4 | 115 | 86.35 |
| Nano-Device: RNA[N]:DNA[w] hybrid RS2-10 (3 nM) | | | | |
| 6 nt toehold | | | | |
| oRNA + 6 | 10 nM | 462098 | 150 | 231049 |
|  | 30 nM | 372427 | 67 | 186213 |
| oDNA + 6 | 20 nM | 145619 | 238 | 2086.2 |
|  | 30 nM | 160475 | 146 | 2299.1 |
| No toehold | | | | |
| oRNA | 100 nM | 77705 | 92 | 38853 |
| oDNA | 100 nM | 72742 | 96 | 1042.2 |

**Calculated compared to the k values measured in the experiments with toehold-less inosine-based RS2 DNA nano-devices.

Example 3 Inosine-Based DNA Nano-Device Efficiently Discriminates Invading Strands at a Single Nucleotide Resolution For analysis of DNA double helix dynamics it is highly desirable to have an analytical system capable of discriminating sequences of nucleic acids at a single nucleotide resolution. In the next set of experiments it was determined whether the analytical performance of inosine-based DNA nano-devices was sufficient to discriminate the invading strands at a single nucleotide resolution. To accomplish this task, the invading strands complementary to the [N] strands of inosine-based [N:W] DNA nano-devices were engineered and their ability to induce strands' displacement to the invading strands containing a single nucleotide mismatch was compared. In these experiments, nano-devices and invading strands were designed to recapitulate the endogenous DNA and RNA sequences harboring disease-associate single nucleotide polymorphism (SNP) variants. Invading strands harboring a single nucleotide mismatch were ~56-fold less potent in inducing the strands displacement (FIG. 26D).

These results demonstrate that inosine-based DNA nano-devices are highly efficient in sensing and discriminating invading DNA and RNA molecules at a single nucleotide resolution, thus further supporting the utility of this system for analysis of DNA double helix dynamics. Inosine-based design of nano-devices and corresponding analytical protocols disclosed herein can be utilized for engineering and cost efficient manufacturing of nano-sensors and analytical instruments for highly reliable, sensitive, and reproducible single nucleotide polymorphism (SNP) measurements.

Example 4 Invading RNA Molecules Induce Strand Displacement Reactions of 5-Methyl-Cytosine DNA Double Helix FIGS. 27A-27D illustrate nano-dynamics of strand displacement reactions induced by invading RNA and DNA molecules in inosine-based cytosine and 5mC-conaining of DNA nano-devices in accordance with some embodiments described herein.

Figure 27A:
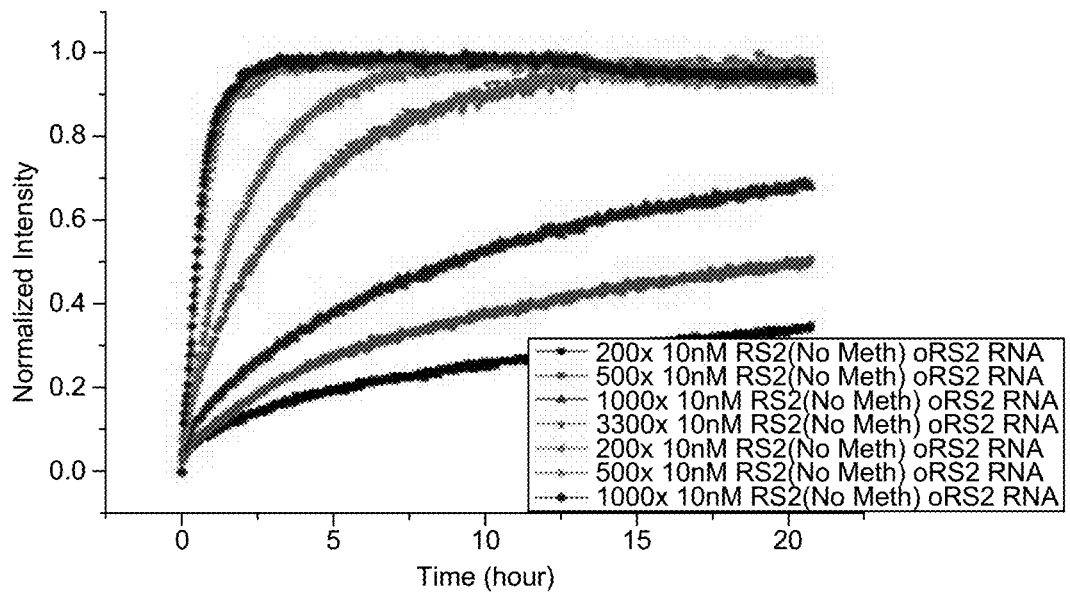
FIGS. 27A-27D illustrate nano-dynamics of strand displacement reactions induced by invading RNA and DNA molecules in inosine-based cytosine and 5mC-conaining of DNA nano-devices in accordance with some embodiments described herein.
Figure 27B:
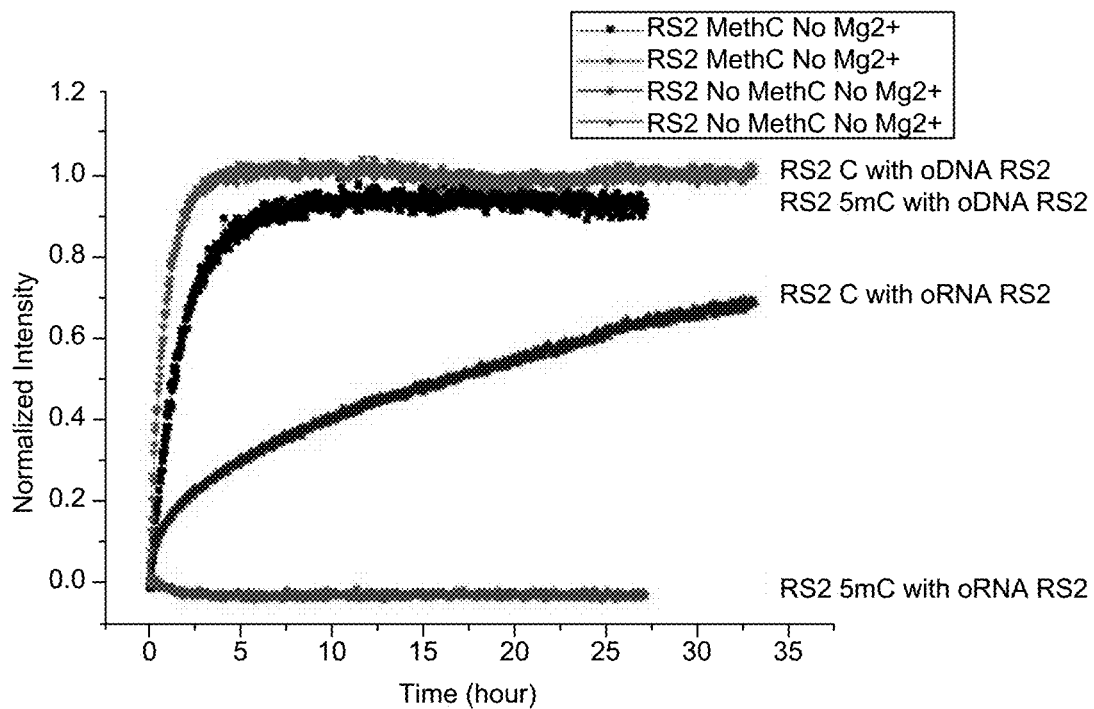
Figure 27C:
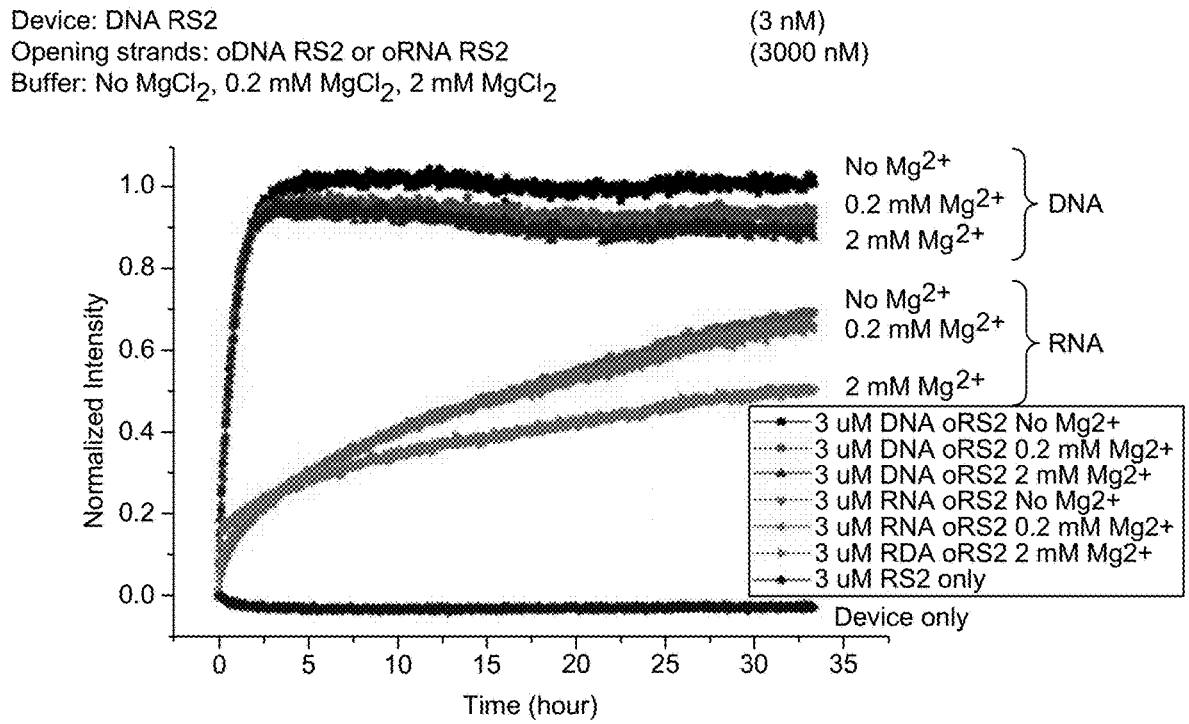
Figure 27D:
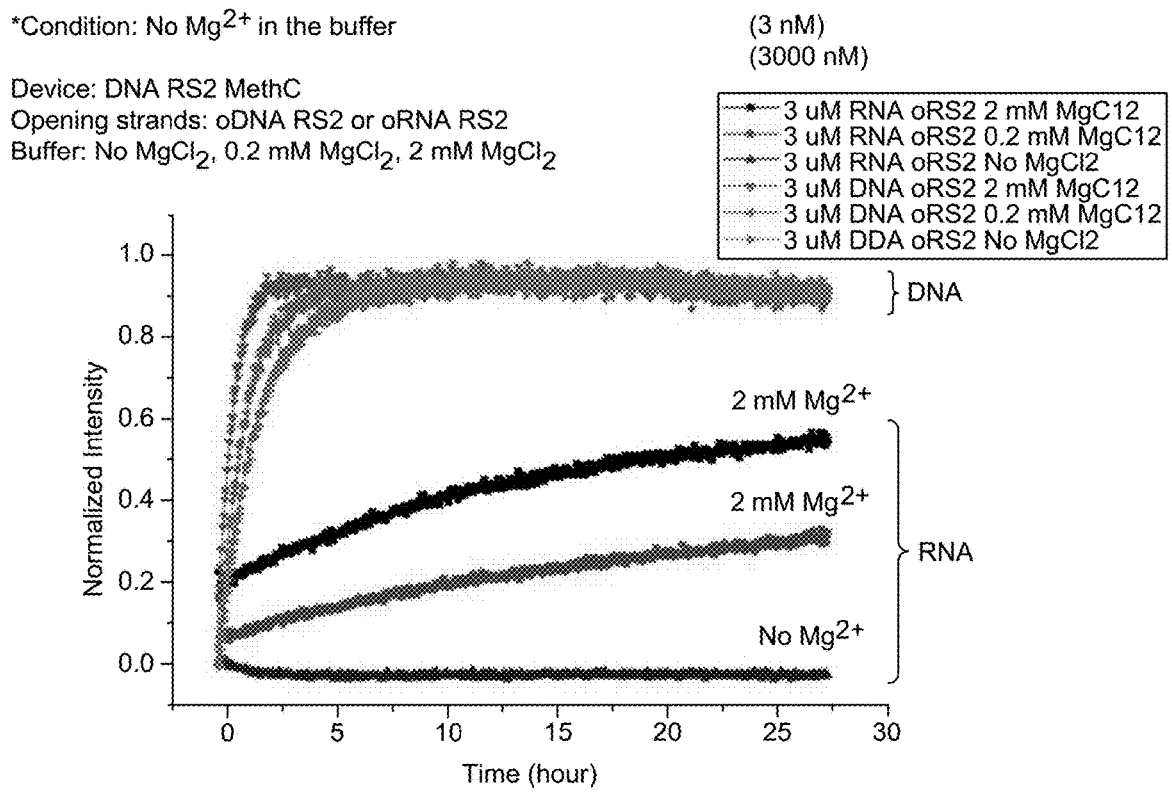

FIGS. 27A-27D show time-lapse dose-response analyses of strand displacement kinetics induced by invading RNA and DNA molecules in inosine-based (FIGS. 27A and 27C) and inosine- and 5mC-containing (as in FIGS. 27B and 27D) DNA nano-devices without (as in FIGS. 27A and 27B) and with bivalent magnesium ions (as in FIGS. 27C and 27D). Table 5 below details the results of quantitative analyses of strand displacement kinetics for corresponding experimental conditions.

TABLE 5

| Strand Displacement Kinetics | | | | |
|---|---|---|---|---|
| | oRNA RS2 | | oDNA RS2 | |
| | $t_{1/2}$ | k $(M^{-1}*s^{-1})$ | $t_{1/2}$ | k $(M^{-1}*s^{-1})$ |
| DNA | | | | |
| No MgCl$_2$ | 58675 | 3.94 | 1855 | 124.55 |
| 0.2 mM MgCl$_2$ | 60475 | 3.82 | 1975 | 116.99 |
| 2 mM MgCl$_2$ | 110215 | 2.10 | 2095 | 110.29 |
| 5 mC DNA | | | | |
| No MgCl$_2$ | n/a | n/a | 4660 | 49.26 |
| 0.2 mM MgCl$_2$ | n/a | n/a | 3010 | 76.76 |
| 2 mM MgCl$_2$ | 62418 | 3.70 | 1570 | 147.17 |

Previous experiments indicate that the kinetics of strands' displacement reactions was significantly affected by structural variations of both DNA double helix and invading strands sequences. In the next set of experiments, it was determined whether naturally-occurring chemical modifications of nucleotides' structure such as cytosine methylation would have an effect on strands' displacement reactions of DNA double helices. Toehold-less DNA nano-devices were designed and manufactured recapitulating endogenous sequences in which 5-methyl-cytosines (5mC) were substituted for cytosine nucleotides and strands displacement kinetics of 5mC-based nano-devices were compared to inosine-based nano-devices containing conventional cytosine nucleotides. Invading RNA molecules triggered a dose-dependent dissociation of DNA strands of toehold-less inosine-based nano-devices as shown in FIGS. 27A-27D. Nano-devices engineered using 5mC-based double helix designs manifested significantly slower kinetics of strands displacement reactions induced by either DNA or RNA molecules as shown in FIGS. 27A-27D. Importantly, the transition efficiency of 5mC-based DNA double helix to a single stranded state was significantly higher in the presence of the physiological concentrations of $Mg^{2+}$ as shown in FIGS. 27A-27D. This effect appeared specific for 5mC-based DNA double helix and it was particularly striking for invading RNA molecules as shown in FIGS. 27A-27D. Introduction of bivalent ions such as $Mg^{2+}$ at physiological concentrations significantly enhanced the transition of 5mC-based DNA double helix from B to Z conformation, suggesting that invading RNA molecules interacted more efficiently with DNA double helix in Z conformation.

Collectively, these data indicate that endogenous RNAs may function as efficient inducers of DNA double helix transitions from double-stranded to single-stranded states at genomic loci containing either conventional cytosine or 5-methyl-cytosine nucleotides. Further, the experiments suggest that cytosine methylation decreases kinetics of DNA strand displacement reactions in response to invading RNA molecules. This inhibitory effect of cytosine methylation may be reversed by transition of 5mC-based DNA double helix to Z conformation in the presence of bivalent ions at physiological concentrations.

Example 5 Markedly Enhanced Responsiveness to Invading RNA Molecules of Toehold-Bearing Inosine-Based Nano-Devices Containing RNA/RNA, RNA/DNA and DNA/RNA Hybrid Duplexes DNA nano-devices engineered using 5mC-based and inosine-based DNA double helix designs manifested significantly slower kinetics of strands displacement reactions induced by invading RNA molecules compared to DNA sequences as shown in FIGS. 27A-27D, suggesting that DNA/DNA binding was stronger compared to RNA/DNA binding in these systems. It was investigated whether double-stranded RNA nano-devices would display more favorable kinetics of strands displacement in response to invading RNA molecules.

Figure 28A:
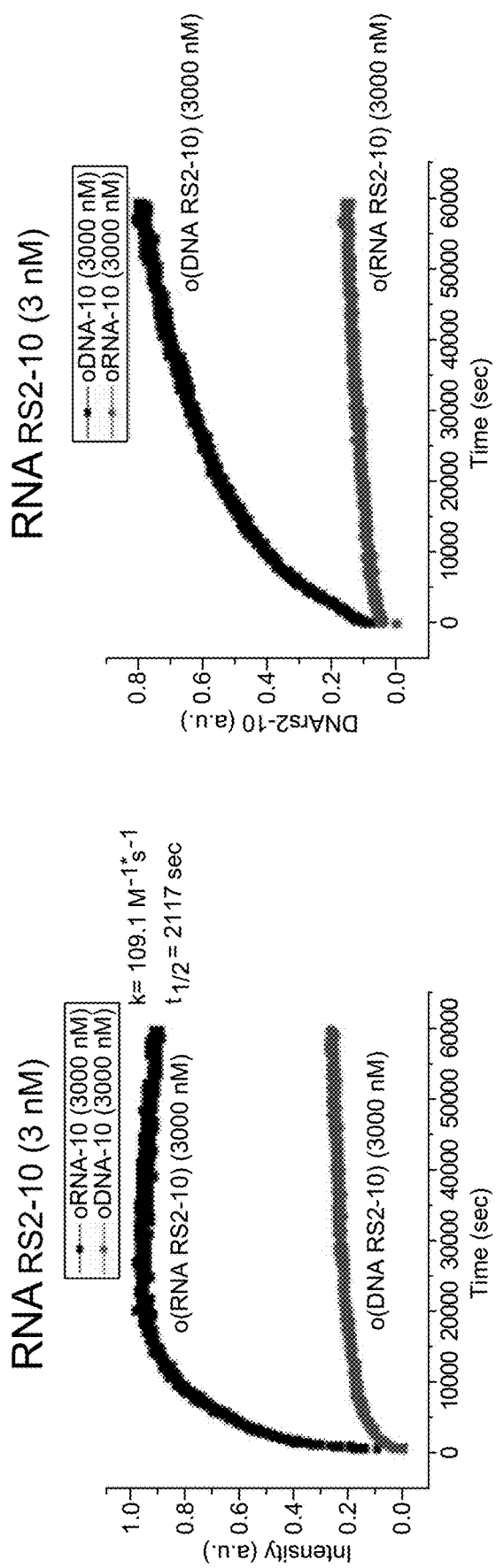
FIGS. 28A-28B illustrate enhanced performance of inosine-based double-stranded RNA nano-devices with toeholds in detecting invading RNA molecules in accordance with some embodiments described herein.
Figure 28B:
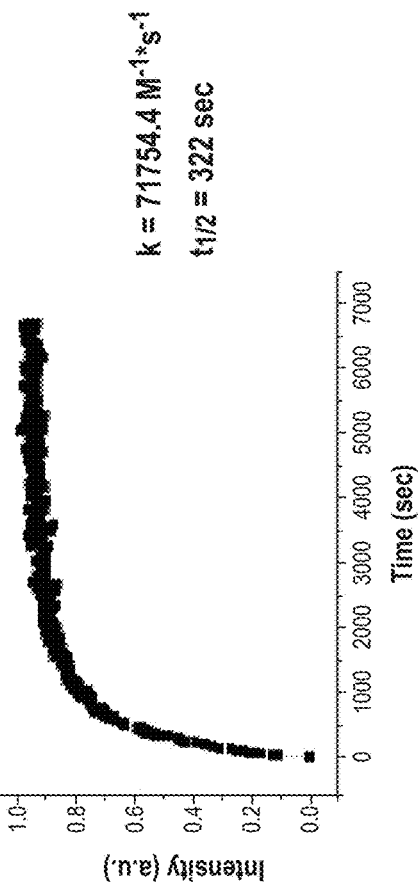

FIGS. 28A and 28B illustrate enhanced performance of inosine-based double-stranded RNA nano-devices with toeholds in detecting invading RNA molecules in accordance with some embodiments described herein.

FIG. 28A shows time-lapse analyses of strand displacement kinetics of inosine-based toehold-less double-stranded RNA (left panel in FIG. 28A) and DNA (right panel in FIG. 28A) nano-devices induced by invading RNA and DNA molecules. FIG. 28B shows time-lapse analysis of strand displacement kinetics of inosine-based double-stranded RNA nano-devices with toeholds. dsRNA and dsDNA nano-devices exhibited dramatically distinct responsiveness to the invading RNA and DNA molecules (FIG. 28A) and markedly enhanced kinetics of strand displacement reactions of inosine-based dsRNA nano-devices with toeholds in response to invading RNA molecules (FIG. 28B).

To enhance the device performance, both inosine substitution and toehold extension concepts shown in FIGS. 28A and 28B were incorporated in a design architecture. Comparisons of toehold-less DNA-based and RNA-based devices demonstrate that double-stranded RNA nano-devices manifested a superior responsiveness to invading RNA molecules which appeared to significantly outperform the strand displacement activity of corresponding DNA molecules as shown in FIGS. 28A and 28B. Notably, double-stranded inosine-based RNA/RNA hybrids-containing nano-devices with toeholds manifested nearly 40,000-fold faster kinetics of strand displacement induced by invading RNA molecules compared to DNA nano-devices, as shown in FIGS. 27A-27D and 28A-28B.

Figure 29A:
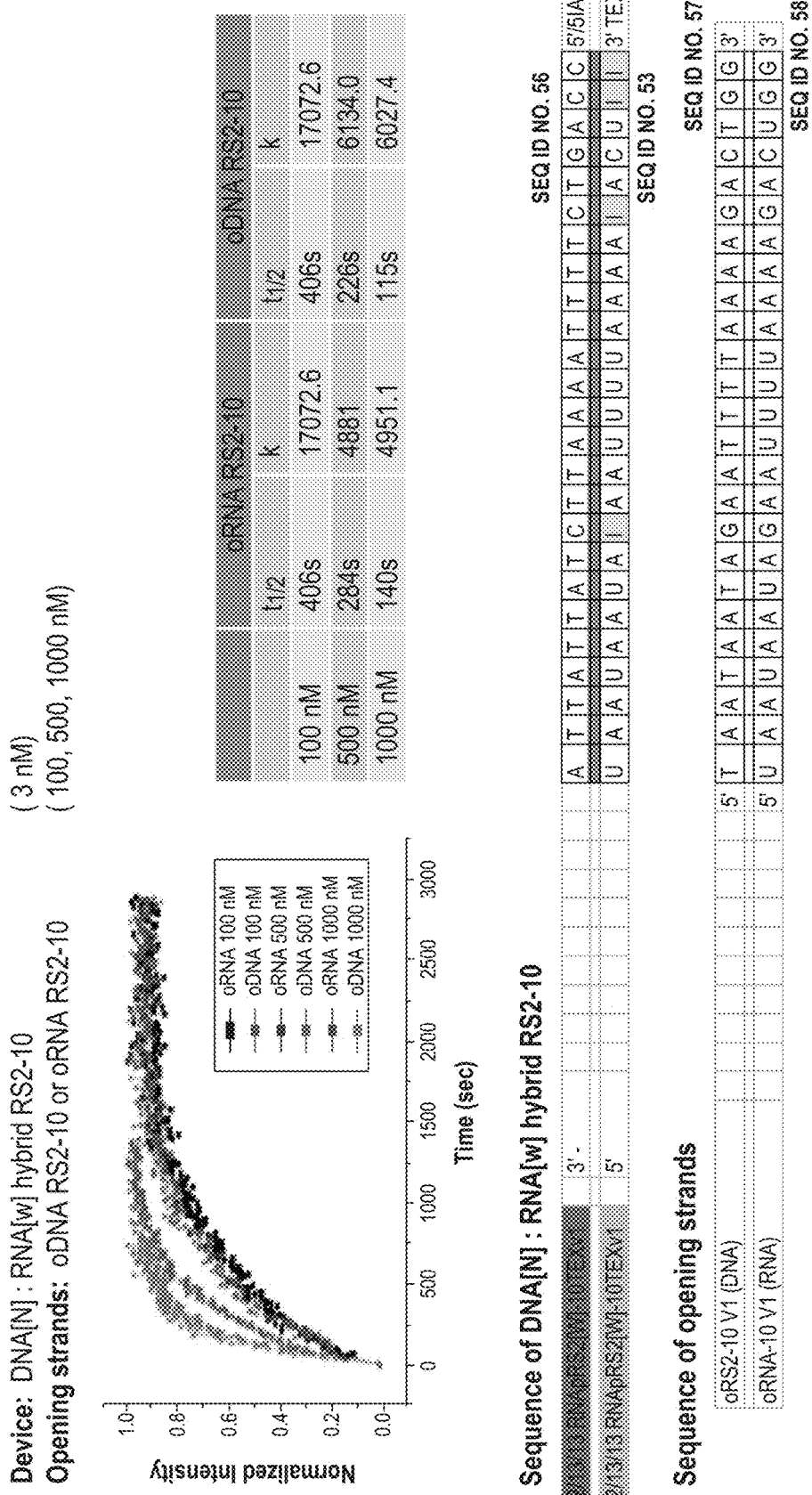
FIGS. 29A-29C illustrate markedly enhanced performance of inosine-based double-stranded RNA/DNA hybrid nano-devices with toeholds in detecting invading RNA molecules in accordance with some embodiments described herein.
Figure 29A:
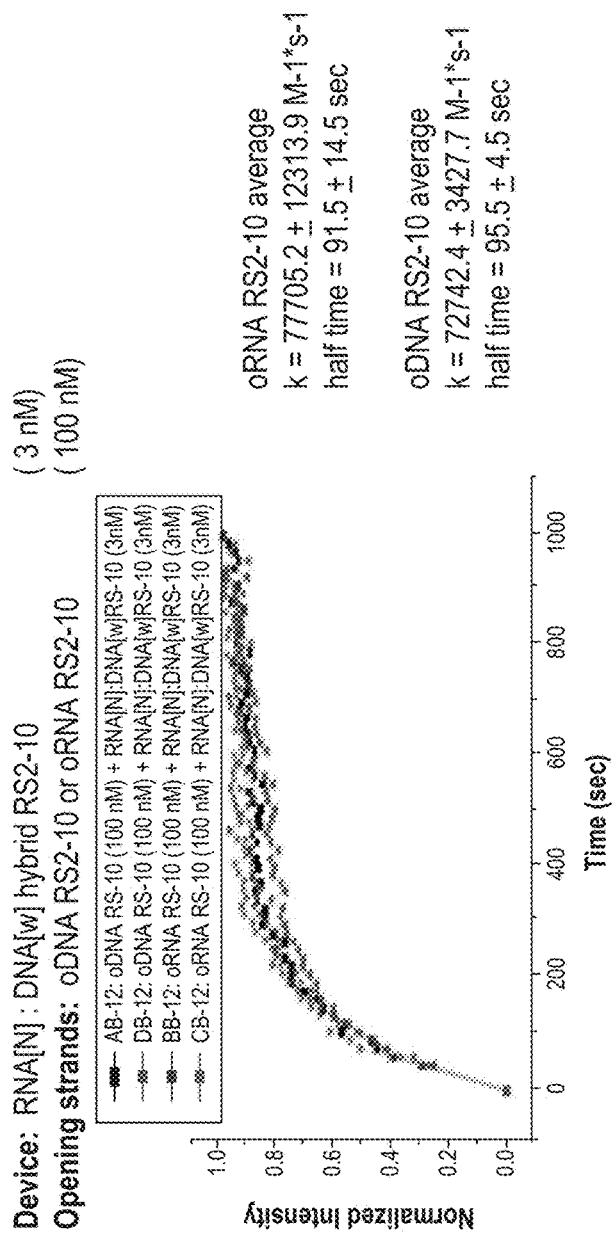
Figure 29B:
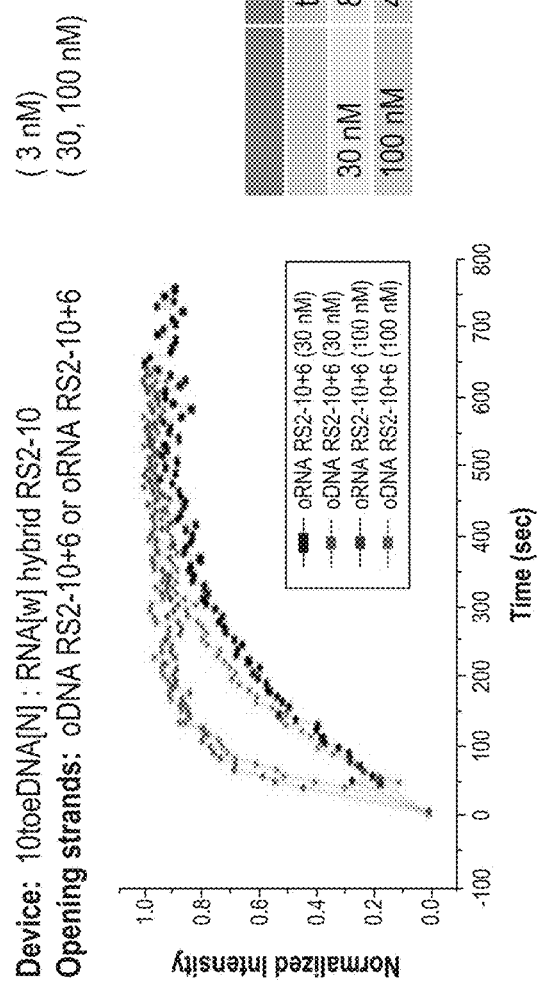
Figure 29C:
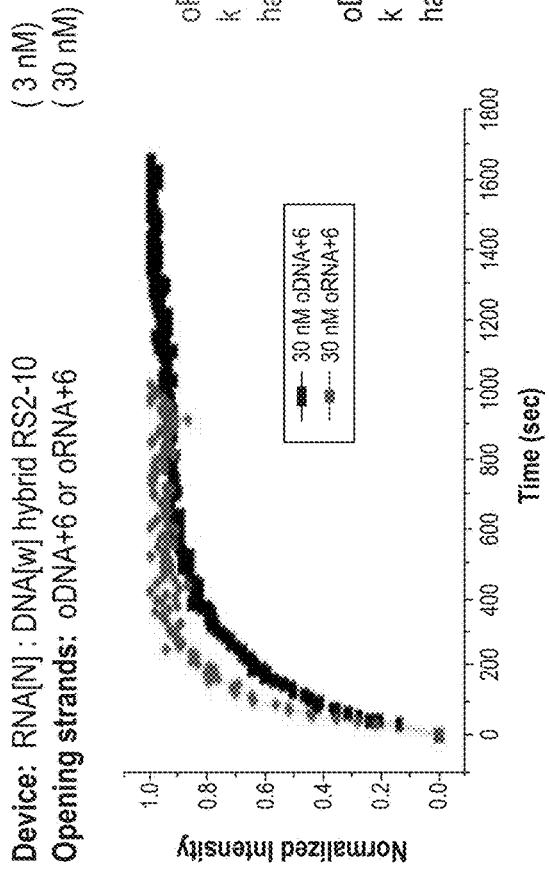

In the next set of experiments the analytical performance of nano-devices containing toehold-less and toehold-bearing DNA[N]/RNA[W] and RNA[N]/DNA[W] hybrid duplexes was investigated (FIGS. 29A-29C; Table 6). Remarkably, these experiments revealed that nano-devices containing toehold-bearing DNA[N]/RNA[W] and RNA[N]/DNA[W] nano-sensors manifested ~90,000-200,000-fold enhancement of nano-device's responsiveness to the invading RNA molecules (FIGS. 29A-29C; Table 6).

TABLE 6

Experimental Rate Constant for Toehold-Mediated Displacement Reactions Measured at 41° C. and 25° C. (in units of $M^{-1}s^{-1}$)

| w/Inosine | | w/o Inosine | |
|---|---|---|---|
| n | $B_{\{LR\}}$ $k_{\{LR\}(0,\,b)}$ k | n | $2^{nd}$-Order fit 25° C. k |
|  |  | 10 | 121000 |
| 8 | 176000 | 8 | 96100 |
| 7 | 168000 | 7 | 80600 |
| 6 | 151000 | 6 | 77100 |
| 5 | 122000 | 5 | 55200 |
| 4 | 77000 | 4 | 1790 |
| 3 | 56000 | 3 | 1270 |
| 2 | 7700 | 2 | 10.3 |
| 1 | 6900 | 1 | 0.92 |
| 0 | 3800 | 0 (BESE)* | N/A |

With inosine data: T=25° C., ε=1.4, $k_n$=1.83×10$^5$ M$^{-1}$ s$^{-1}$ (obtained from assuming a pseudo-first order reaction of n=8 as described above), $k_{\{LR\}}$ and $k_{\{L\}}$ were calculated assuming a pseudo-first order reaction. [B]=3 nM, [f]=30 nM (except for n=1,2, [B]=10 nM, [f]=100 nM and for n=0, [B]=3 nM, [f]=300 nM). †Predicted empirically as [$k_{\{L\}}$(n=1)]+[$k_{\{LR\}}$(n=0)].
Without inosine data: For T=25° C., ε=3.3, $\Delta G_\varepsilon \approx \Delta G_{base}$=−1.50 kcal/mol, $k_n$=1.24×10$^5$ M$^{-1}$ s$^{-1}$ (obtained from assuming a pseudo-first order reaction of n=10 as described), b=30 and $P_c$(10,30), [S]=3 nM, [f]=30M (except for n=3, 4, [f]=1 M, n=2, [f]=10 μM and for n=1, [f]=100 μM).

FIGS. 29A-29C illustrate markedly enhanced performance of inosine-based double-stranded RNA/DNA hybrid nano-devices with toeholds in detecting invading RNA molecules in accordance with some embodiments described herein.

FIG. 29A shows time-lapse analyses of strand displacement kinetics of inosine-based toehold-less double-stranded DNA[N]/RNA[W] (top panel) and RNA[N]/DNA[W](bottom panel) nano-devices induced by invading RNA and DNA molecules. FIGS. 29B and 29C show time-lapse analyses of strand displacement kinetics of inosine-based double-stranded DNA[N]/RNA[W] (FIG. 29B) and RNA[N]/DNA[W] (FIG. 29C) nano-devices with toeholds. The kinetics of strand displacement reactions of inosine-based ds RNA[N]/DNA[W] nano-devices with toeholds in response to invading RNA molecules was markedly enhanced (FIG. 29C).

The experiments demonstrate that the design of nano-devices for detection and quantitative analyses of RNA molecules should incorporate the architectural principles of inosine substitutions and toehold extensions during engineering and manufacturing of double-stranded RNA-based nano-sensors. Furthermore, these data suggest that the presence of antisense transcripts in biological systems may have a dramatic effect on DNA double helix dynamics: they appear to preferentially bind to complementary RNA molecules and efficiently remove RNAs from RNA/DNA hybrids triggering transition from single-stranded to double-stranded states.

Example 6 A Self-Sustaining Continually Cycling DNA Nano-Device for Modelling and Mechanistic Analysis of DNA Double Helix Dynamics It is desirable that DNA double helix dynamics of both strand dissociation and re-association reactions are continually monitored using the same DNA molecules as it occurs during DNA double helix opening and closing cycles in vivo. A simple DNA device which captured and released of specific DNA strands repeatedly during continuous cycles of operation was designed, as shown in FIG. 19. This system is referred to as a "Capture and Release device" (CR device). The device was composed of three parts, a right side (R), a left side (L) and a targeted capture and release strand (T). Desired interactions of strands were regulated by controlling the number of nucleotide mismatches, toeholds' design, inosine for guanine substitutions, and hybridization length of interacting strands. R and L were complimentary to one another. T is complimentary to part of L, however, it did not possess enough energy to displace R and hybridize to L spontaneously. At the initial state, R and L were hybridized and T was floating freely in the same system. The fuel strand (F) was complimentary to part of R and partially displaced L when it hybridized with R, after it was introduced into the system. R and L remained partially bound together in a hinge region, to keep the device intact. The introduction of F allowed the displaced portion of L to freely hybridize to T that was already present in the system. The anti-fuel strand (C, or AF in some instances) neutralized F as they were complimentary. Removal of F resulted in R and L re-hybridizing evicting T from its hybridization state, such that it again entered a single stranded state. Thus, the device captured T when F was introduced, and released it when C was present. One full cycle of F and C addition returned the device and T to their initial states. F-C pairs were waste by-products of each cycle.

To prove successful operation of this device, a fluorescence probe was tagged to L and a fluorescence quencher to T and the activity was monitored in the spectrometer. Addition of F to the system resulted in opening, and a rapid and continuous decrease of fluorescence indicating binding of T containing the quencher (see FIGS. 19 and 30A-30B). Three minutes of measurements were taken for stabilization and completion of the reaction and the closing cycle was triggered by the addition of C strand. When the device was closed after the introduction of C, the fluorescence signal increased to near the maximum, indicating that T, which contained the quencher, was released from the device as a result of F and C hybridization and R and L re-association. Successive capturing and releasing cycles at 35° C. with 250 nM device was performed (see FIGS. 19 and 30A-30B).

Subsequent addition of more F resulted in dissociation of R and L strands and recapture of the T strand. For comparisons, two control states are shown: 1) a maximum basal fluorescence of a device without any quencher; and 2) a minimum fluorescence fully quenched state of a fluorophore-containing L strand bound to a quencher-containing T strand without the rest of the device assembly (see FIGS. 19 and 30A-30B). Presence of T strand containing quencher reduced the total fluorescence level indicating some basal binding of T to L which resulted in quenching of fluorescence. The addition of the fuel strand did not result in full binding of the target strand as it did not reach the fully quenched state of the control. This occurred due to the controlled affinity of T to the device which limited strong binding. The continuing operation of the device demonstrated reliability and robustness. The devices performed efficiently the capture and release functions in 3 successive cycles. However, the cycles showed decrease of the maximum and the minimum peak of fluorescence as additional F and C were introduced into the system. This could result from poisoning of the system from residual waste, such as F-C double helixes, and could be addressed by developing waste removal protocols for extended operations of CR nano-devices.

The recycling usage of the CR device offered several practical advantages. It could significantly reduce the production and operation cost for prospective analytical applications. The CR device provided analytical benefits through its repeating operation by responding to presence of fueling and anti-fueling strands. Moreover, a microarray could be fabricated for in vitro diagnostic applications with a CR device which could be repeatedly activated and deactivated to confirm results. This would improve the sensitivity and specificity of the sensor.

Figure 30A:
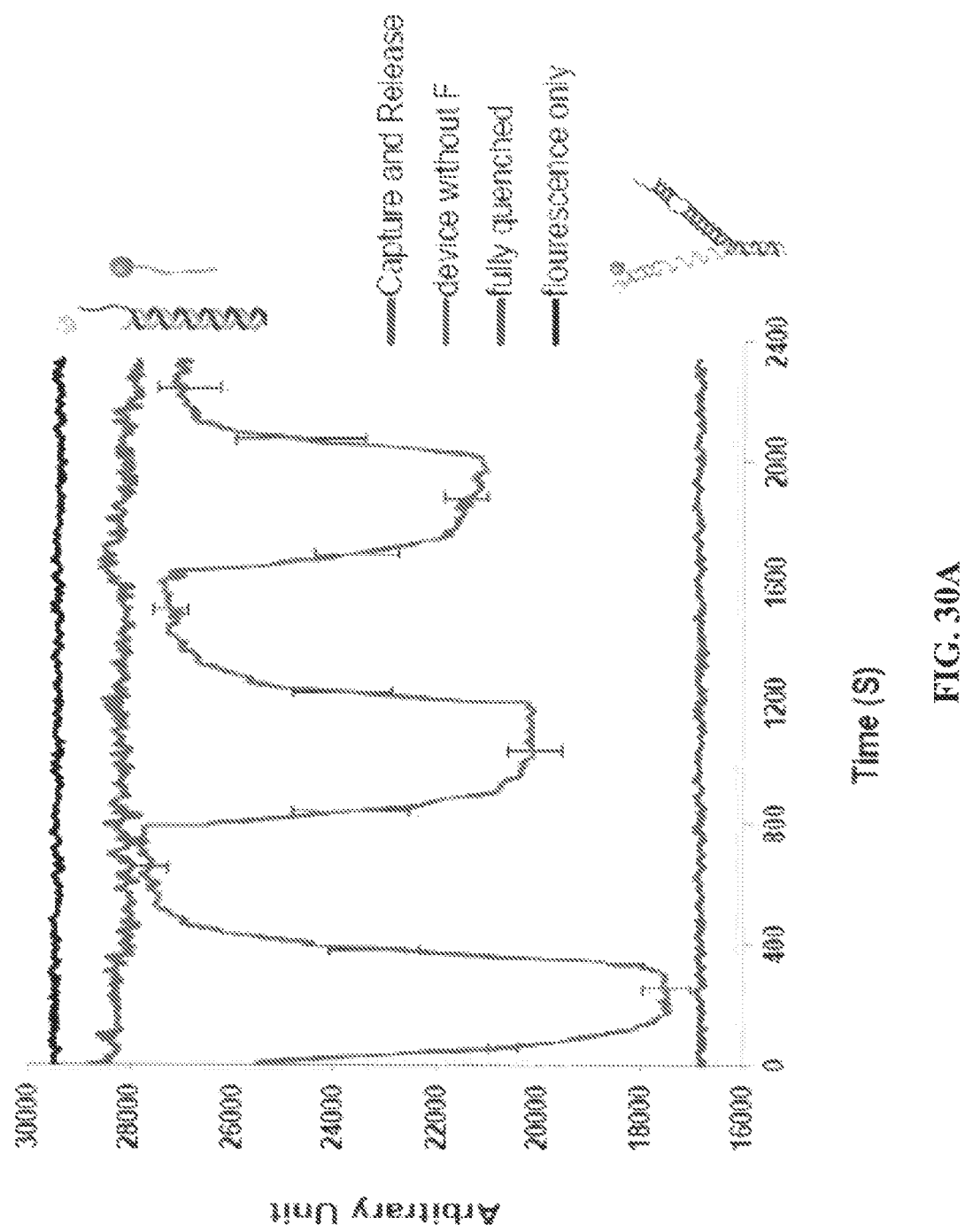
FIG. 30A shows time-lapse fluorescence analysis of successive capturing-releasing cycle at 35° C. for CR with three nucleotide mismatch. Fluorescence only, device only (device maximum fluorescence state); and fully quenched states (device minimum fluorescence state) are shown. Capture and release cycling of the target strand is also depicted.
Figure 30B:
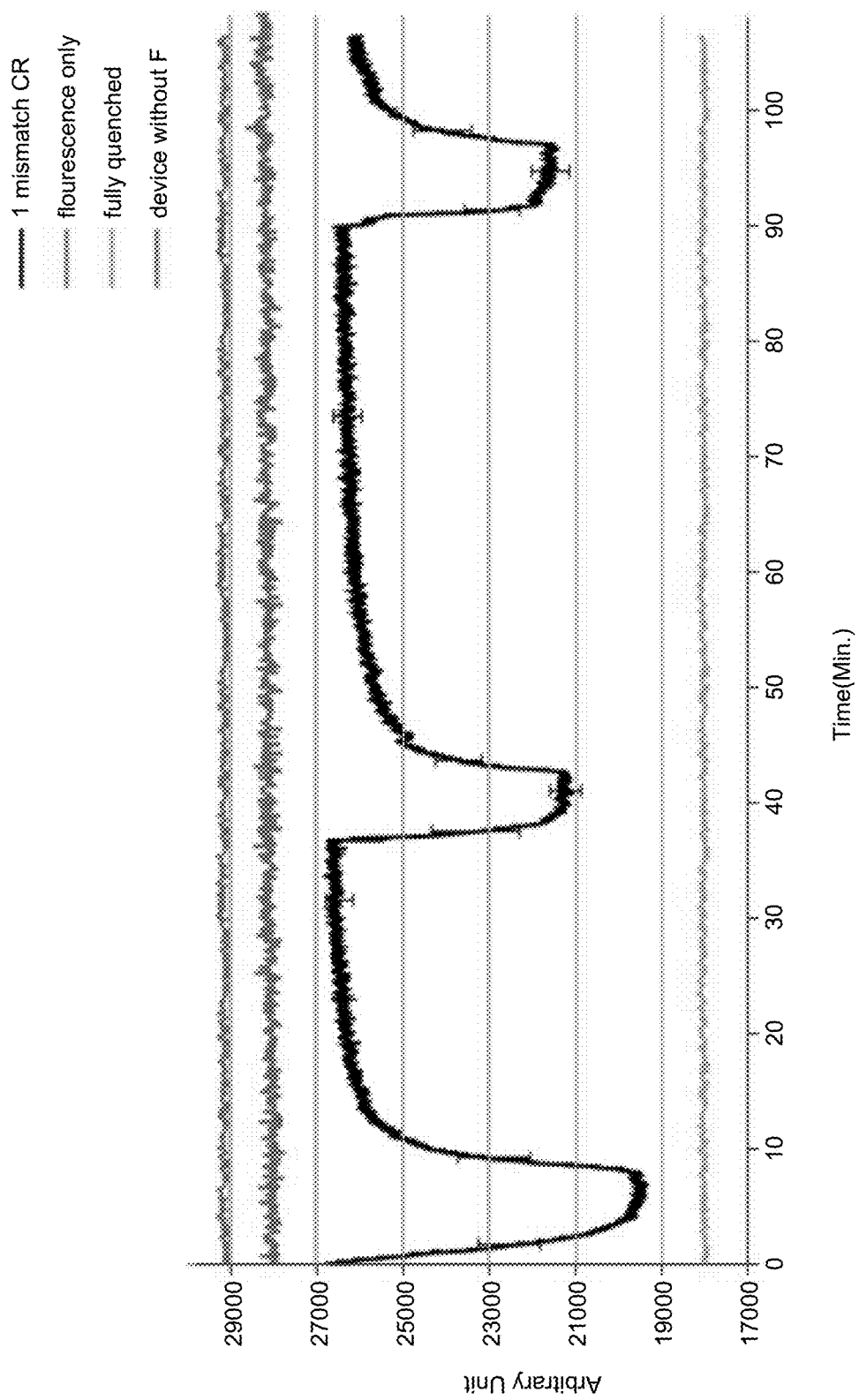
FIG. 30B shows time-lapse fluorescence analysis of successive capturing-releasing cycle at 35° C. for CR with one nucleotide mismatch.

FIGS. 19 and 30A-30B illustrate design and experimental validation of a self-sustaining continually cycling capture-and-release DNA nano-device for modelling and mechanistic analysis of DNA double helix nano-dynamics in accordance with some embodiments described herein.

FIG. 19 shows schematic of the capturing and releasing cycles of capture-and-release (CR) nano-devices. At the initial state, DNA devices and target strands (T) were not reacted in equilibrium. After adding F, F attracted part of the device (R) and the device opened. At the same time, T hybridized to L. At opened state, empty space between F and R represented 1-3 nt mismatches that reduced affinity between F and T. Adding C lead to the initial state, detaching F from R, allowing re-association of R and L and release of T. Fluorescence and quencher were tagged to observe activity of operation. Hybridization of T to L caused quenching of the fluorophore.

FIG. 30A shows time-lapse fluorescence analysis of successive capturing-releasing cycle at 35° C. for CR with three nucleotide mismatch. Fluorescence only, device only (device maximum fluorescence state); and fully quenched states (device minimum fluorescence state) are shown. Capture and release cycling of the target strand is also depicted.

FIG. 30B shows time-lapse fluorescence analysis of successive capturing-releasing cycle at 35° C. for CR with one nucleotide mismatch.

Example 7 Fluorescence Observation of Device Activity

Operation of the device was monitored over time by fluorescent probes. Fluorescent probes were tagged to L, while a fluorescence quencher was attached to T (FIG. 21). Upon hybridization, quenching of the probe was achieved. Shifting the equilibrium state of the system was required to have a self-sustaining device. The operating behavior of the device (equilibrium of the system) was a function of the temperature and concentration of the individual reactants of the system. Increasing the temperature of the system can have similar consequences on the functionality of the device as decreasing the concentrations. Thus, experiments were conducted at 27° C., 36° C., and 40° C. with 150 nM of tweezers and 450 nM of T. Measurements were also done with 40 nM, 150 nM and 450 nM of tweezers with 3× excess T at 36° C.

Figure 31B:
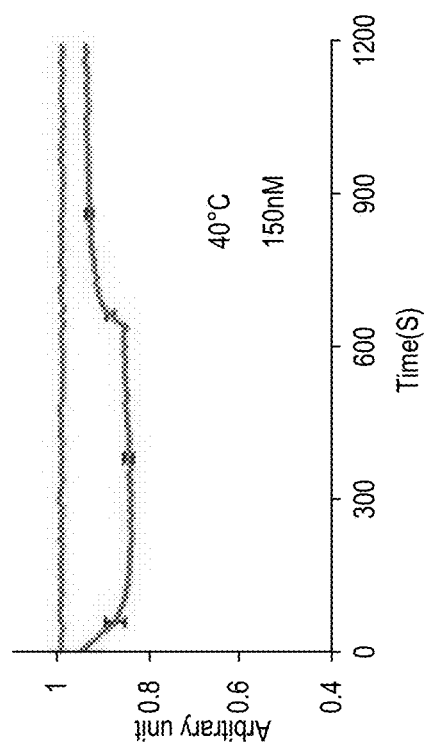
FIGS. 31A and 31B show the activity of 150 nM samples at 27° C. and 40° C. respectively.
Figure 31D:
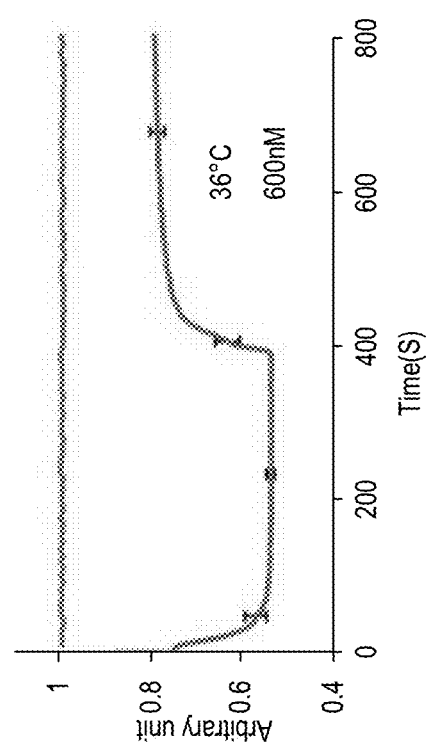
FIGS. 31C and 31D show operation at 36°
Figure 31A:
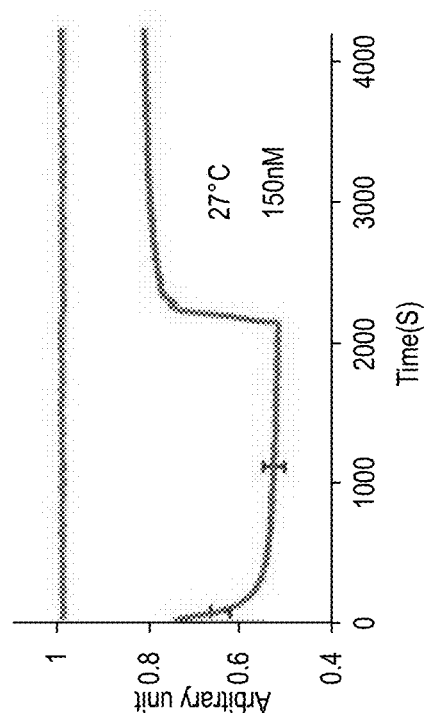

Because of the 6 nt toehold on T, the stability of the device at equilibrium increased significantly at lower temperatures (FIGS. 31A and 31B). Increasing the temperature from 27° C. to 40° C. resulted in decreased affinity between T and L. When F was added to the system, little quenching was observed at elevated temperatures. This indicates that T was unable to stably bind to L. However, at lower temperatures, the increased hybridization of T to L resulted in a reduced maximum fluorescence when the device was closed to prevent capture of T. At this lower temperature, the device showed a much greater difference between the open and closed states indicating that greater release and capture was achieved.

Figure 31C:
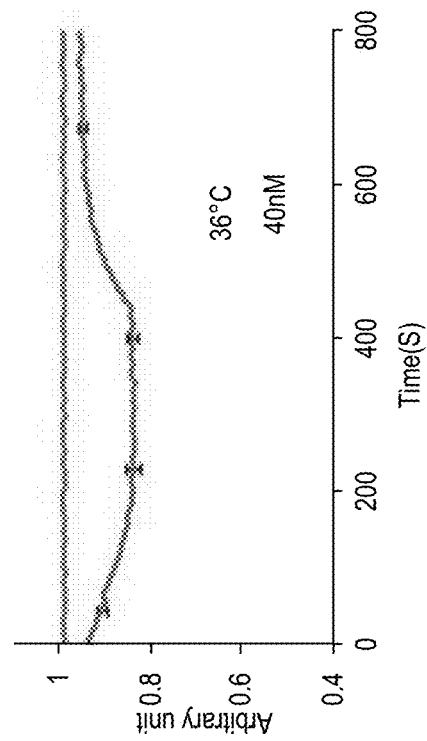

Similarly, concentration also affected the device operation. As concentration increased, greater device robustness was achieved. However, similar to at 27° C., maximum fluorescence was reduced. Low concentrations resulted in decreased affinity between T and L resulting in weak capture when the device was opened (FIG. 31C). More detectable differences between captured and released states were achieved at elevated concentration (FIG. 31D). This occurred since hybridization energy between 17 nt of T and L increased as the concentration increased. For this device to operate properly, a careful balance of concentration and temperature was required such that the maximum differences in captured and released state were detectable.

Figure 32A:
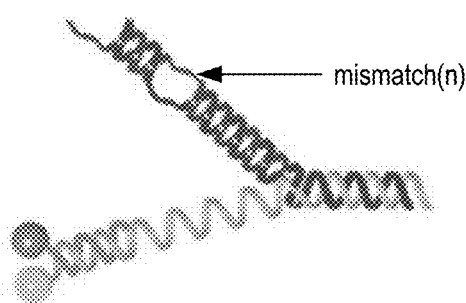
Figure 32B:
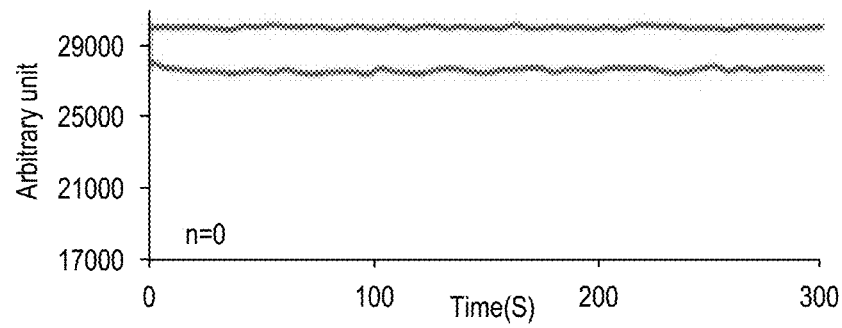
Figure 32C:
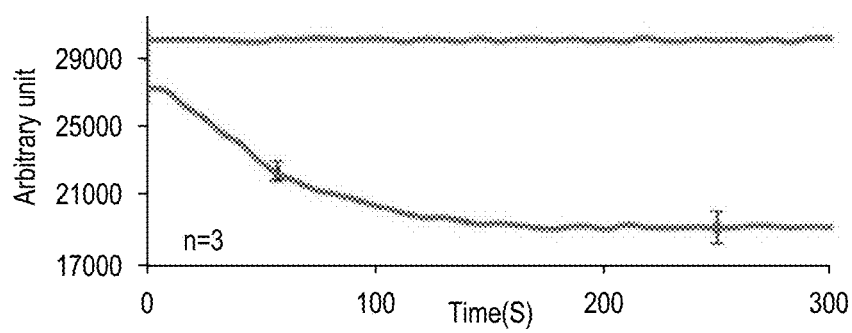
Figure 32D:
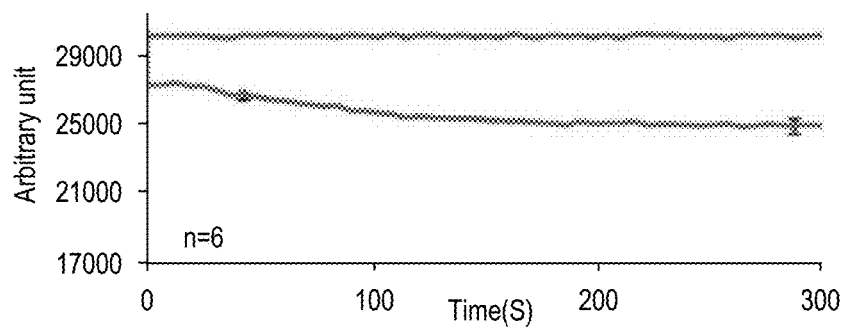
Figure 32E:
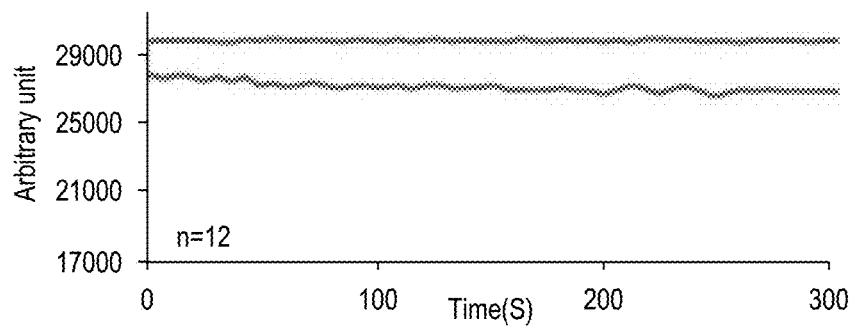

Altering the number of mismatches in F with T and R eventually lead to device inactivation. The device did not function properly when the opening strand F had more than 6 nt of mismatch or no mismatch (FIG. 32A). The mechanism of device failure changed for no mismatches and 6+ mismatches. When no mismatches were present in F, it was able to stably bind to both T and R. The excess F opened the device, but T was unable to bind to L as it stably hybridized to F. No quenching, through capture of T, was observed despite the device being opened (FIG. 32B). 1 to 3 mismatches resulted in normal device activity as T-F binding is not stable, while F and R were able to hybridize stably (FIG. 32C). Increasing the number of mismatches present in F to 6 or 12 prevented stable hybridization between F and R. F was not able to displace the L from binding to R preventing the device from opening and capturing T (FIGS. 32D and 32E).

Example 8 SNP Detection with Fluorescence Observation

In another example, the strand displacement was monitored over time with fluorescence labelling (FIG. 33). A Texas Red fluorescence was labeled at the end of W and a fluorescence quencher was at the end of N. The quencher absorbed the emission wave from the fluorescence when it was adjacent to fluorescence label, thus upon hybridization of N and W, the fluorescence was quenched. When the perfect match T was added on the sample, strand displacement happened and the fluorescence and quencher were separated each other and the signal became brighter. However, when the single mismatch T was added, strand displacement happened much slower and much lower signals were measured compared to a perfect match T. The structure of the double-stranded (DS) probe with the specific sequence is shown in FIG. 34.

N strand which was tagged with fluorescence quencher and W strand with fluorescence label were mixed in ratio of 1:1 in 1×PBS solution and annealed from 20° C. to 90° C. and cooled to 4° C. over 3-4 hours. A Texas Red having excitation maximum wavelength of 596 nm and emission maximum wavelength of 613 nm was used. Perfect match and single mismatch T strand were both suspended in 1×PBS. The hybridized DS probe was diluted in 1×PBS into 20 nM and tested using a Tecan Infinite 200 M plate reading spectrometer (San Jose, Calif.) at 27° C. with an accuracy estimated to be approximately ±1.5° C. Excitation/Emission of TEXAS red were observed at 590/620 nm. Each experiment began with a 50 µL sample volume with a device concentration of 20 nM (20 nm of DS probe and 100 nM or 300 nM of T) in black 96 well plates. Clear microplate sealing films were applied over the sample wells to avoid evaporation. The same test was conducted in 1×PBS buffer solution.

The length of the toehold affected the reaction rate and thus varied length of toeholds were tested (FIG. 36). The test with 10 nt toehold showed vague discrimination of a single mismatch because affinity between N and T was too strong with 10 nt toehold. The two strands hybridized even with the single-mismatch.

To confirm that the single mismatch T did not hybridize partially from toehold part until the mismatched point, the discrimination was verified by DNA gel electrophoresis. To perform DNA gel electrophoresis, the structure of the DS probe was modified to accumulate T to DS probe, not just exchanging their position. The operation of DS probe was not affected when W and N were bound by hinge part in that the hinge part was introduced to conform the DS probe partial-triple strand after strand displacement (FIG. 37). The gel image shows that the reacted sample with the single mismatch T stained weaker than the sample with perfect match T, meaning that the single mismatch T did not displace W effectively compared to the perfect match T (FIG. 37).

Figure 25A:
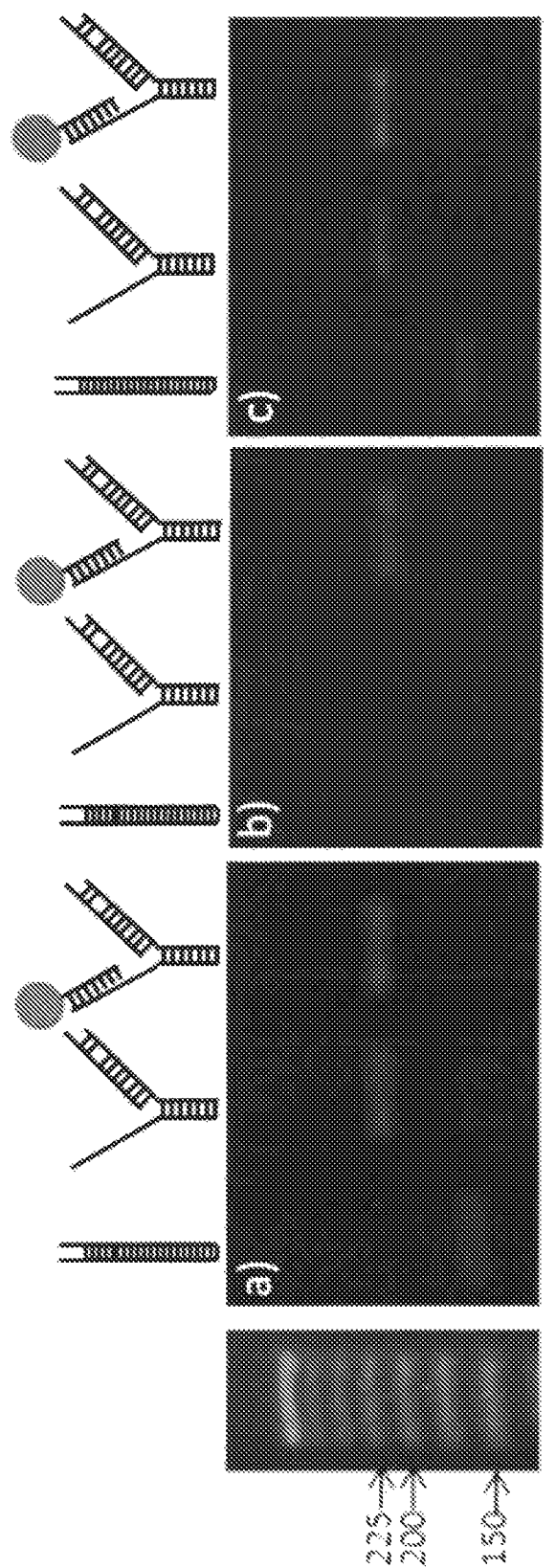
FIG. 25A shows gel electrophoresis analysis of CR device operation. For all panels (a)-(c), lane 1 is the initial state, which is the equilibrium state with closed tweezers and T without reaction. Lane 2 is opened device without T. Lane 3 is capturing state, opened tweezers with T. DNA ladder is shown to the left of the panels. Panel (a) shows that the position of the double stranded DNA was determined by EtBr staining. All three lanes appeared and the opened tweezers appeared at a higher position, indicating slower migration. Panel (b) shows that the same gel was scanned by laser to visualize the FAM. Only lane 3 shows the staining as FAM is only tagged to T. Panel (c) shows an overlay of the first two panels, confirming the capture of T only in open state.
Figure 25B:
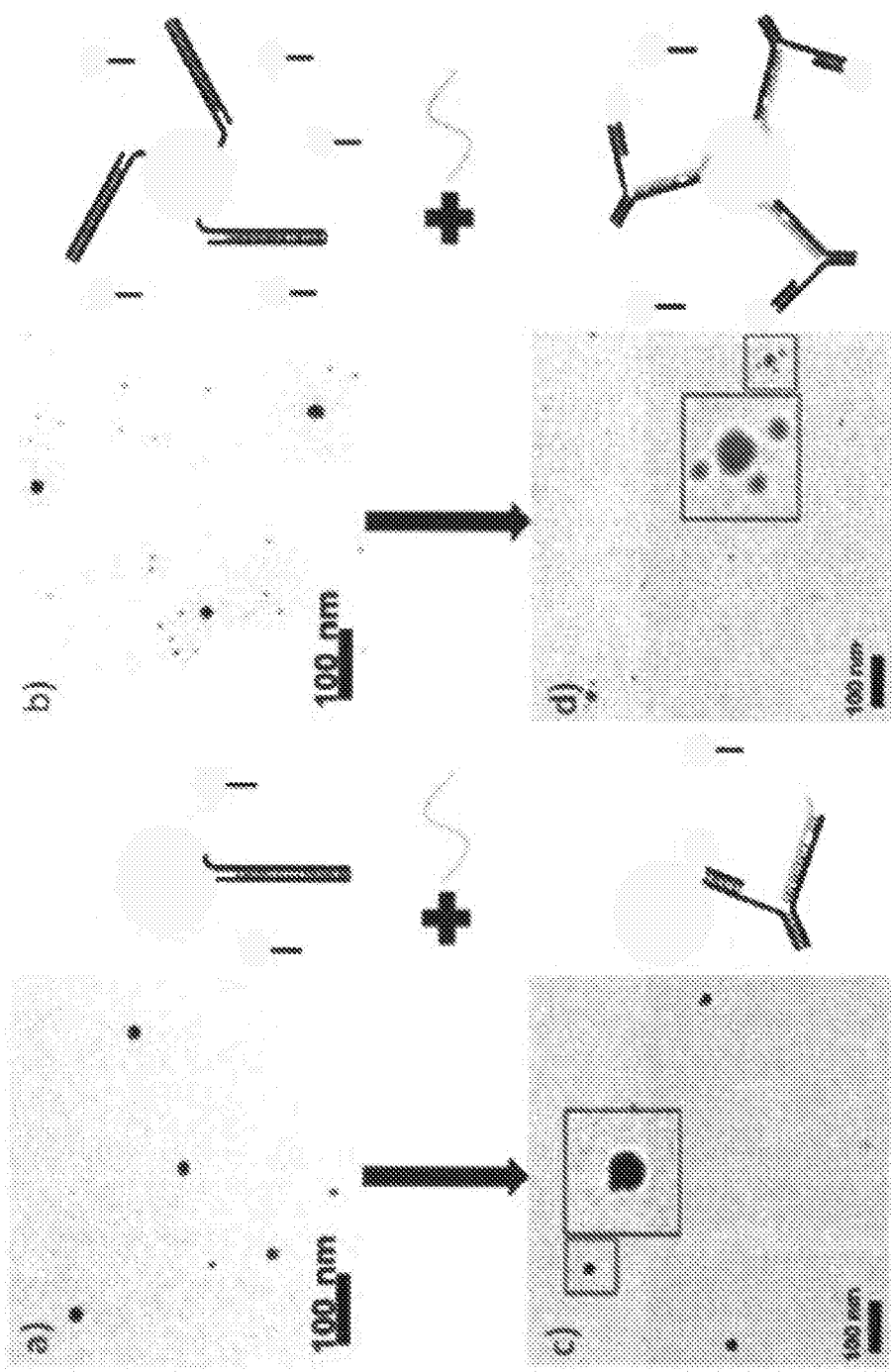
FIG. 25B shows TEM images of AuNP functionalized devices. Panels (a) and (b) show the initial state of the devices, with either L bound to 20 nm AuNP (panel (a)) or R bound to 20 nm AuNP (panel (b)) while 10 nm particles are attached to T. Panels (c) and (d) show multimeric conformation of the AuNP upon addition of F causing 10 nm functionalized to T to be captured by the devices attached to larger AuNP. Scale bars show 100 nm.

Example 9 Translation of Strands Displacement Reactions into Defined Geometrical Shapes for Visualization of DNA Double Helix Nano-Dynamics FIGS. 25A and 25B provide visualization of DNA double helix nano-dynamics by translation of strands displacement reactions into defined geometrical shapes in accordance with some embodiments described herein.

FIG. 25A shows gel electrophoresis analysis of CR device operations. For all panels in the subplots (a) to (c), lane 1 was initial state, which was the equilibrium state with closed tweezers and T without reaction. Lane 2 was opened devices without T. Lane 3 was capturing state, opened tweezers with T. The small picture left to subplot (a) shows DNA ladder. Subplot (a) shows that position of double stranded DNA was determined by EtBr staining. All three lanes were appeared and opened tweezers appeared at a higher position, indicating slower migration. Subplot (b) shows that the same gel was scanned by laser to visualize the FAM. Only lane 3 showed the staining as FAM was only tagged to T. In subplot (c) an overlay of the first two panels is shown, confirming the capture of T only in the open state.

FIG. 25B shows TEM images of AuNP functionalized devices. Subplots (a)-(b) show initial states of the devices, with L bound to 20 nm AuNP (a) and R bound to 20 nm AuNP (b). Subplots (c)-(d) show distinct multidimensional AuNP (b). Subplots (c)-(d) show distinct multidimensional conformation patterns of the AuNP upon addition of fueling strand F causing 10 nm AuNP attached to T to be captured by the devices harboring larger 20 nm AuNP.

To visualize DNA strand displacement reactions and demonstrate the potential nano-mechanical applications, gold nanoparticles (AuNPs) of different sizes were attached to tweezers and T. Operation of the devices was also seen by transmission electron microscopy (TEM, JEOL 1200 EX II TEM). The DNA sequences were elongated by adding thiol containing arms (A) to R and L, enabling DNA to attach to gold-nano particle (AuNP [d=10-20 nm]) for TEM visualization. As an example of the device's mechanical activity, it was utilized to capture and release AuNPs linked to small DNA strands. Successful capture of AuNPs was visualized with TEM. 20 nm AuNPs were attached to either R or L while 10 nm particles were attached to T. AuNPs attached to R resulted in a separation gap between 20 nm and 10 nm particles when T bound AuNP were captured (panel (d)), while no gap was present when AuNPs were attached to L(panel (c)), as shown in FIG. 25B. In the initial (released) state, devices, which were attached to 20 nm AuNP, were dispersed from the 10 nm particles (panels (a) and (b)), as shown in FIG. 25B. Addition of F resulted in assembly of AuNP complexes as shown in panels (c) and (d) of FIG. 25B. In the experiments with L bound to the 20 nm AuNP, the devices and AuNP were mixed at a 1:1 ratio resulting in dimer pairs of 10 nm and 20 nm particles (see panels (a) and (c) of FIG. 25B). Formation of larger multimeric structures was achieved by increasing the number of devices relative to the number of AuNP (see panels (b) and (d) of FIG. 25B). Tetramers were assembled by mixing devices and AuNPs at 3:1 ratios as shown in FIG. 25B. Additional TEM images are shown in FIG. 24.

Capture and release states and geometric shape changes of the CR device were verified by DNA gel electrophoresis as shown in FIG. 25A. In these experiments, the same extended devices (FIG. 22) used in the Transmission Electron Microscopy experiments were run on the gel and processed for visualization of the end products. The double helix conformation of [L:R] (closed tweezers), [L, R:F] (F-tweezers hybridization) and [L:T, F:R](capturing state) were created at room temperature. Samples were mixed as described in the fluorescent experiment with 1:1:4 for [L:R:F] and 1:3:4:1 for [L:T:F:R].

In these experiments, the DNA devices were unlabeled while T contained a fluorophore. T strand was a 17 nt single stranded sequence. The devices were 96 nt, double stranded, and had 26 nt extended arms. See FIG. 22. Successful opening of the device and capture of a target DNA strand was visualized on a gel as shown in FIG. 25A. Geometric changes in the DNA resulted in different migration speeds of the device when pulled through the gel. Addition of the fuel strand, successfully resulted in device opening. Addition of the target strand with FAM showed the same open geometry with a band at the same height, but confirmation of capture was affirmed via a band in the FAM channel as shown in FIG. 25A.

Example 10 A Model of RNA-Guided DNA Double Helix Nano-Dynamics

FIGS. 38A and 38B illustrate that DNA methylation-associated genome editing mechanisms triggered TET protein dependent and independent cytosine reconstitution pathways facilitating the recovery of the conventional DNA double helix and altering the sensitivity of DNA double helix to invading RNA molecules in accordance with some embodiments described herein.

FIG. 38A depicts that DNA methylation-associated genome editing mechanisms and TET protein dependent and independent cytosine reconstitution pathways facilitated the recovery of the conventional DNA double helix.

FIG. 38B shows that distinct initial states of DNA double helix were associated with differential sensitivity to the invading RNA molecules and distinct effects on DNA double helix dynamics.

FIG. 39 illustrates a working model of RNA-guided DNA double helix nano-dynamics governing chromatin reprogramming and transitions to distinct regulatory states of chromatin in vivo in accordance with some embodiments described herein.

Typically, nucleosomal DNA is not accessible for regulatory proteins. It undergoes rapid spontaneous unwrapping/rewrapping cycles: it remains fully wrapped for ~250 ms before unwrapping and rewrapping within ~10-50 ms. Spontaneous conformational changes of nucleosomes leading to a transient lift of a DNA stretch from the histone surface and a site exposure for sequence-specific DNA binding proteins are likely to occur at the genomic loci harboring "nascent" chromatin lacking linker histone H1. Capturing of proteinless DNA strands and RNA-guided DNA strands displacement reactions in vivo are predicted to take place during a rapid transient DNA strands unwrapping off the histone surface.

The experiments disclosed herein identified novel structural determinants markedly affecting the kinetics of DNA strands displacement reactions that may have fundamental mechanistic implications by asserting the regulatory effects on DNA double helix dynamics in vivo as shown in FIGS. 38-39. A model of RNA-guided regulatory mechanism triggered a shuttle-like cycle of transitions between the single-stranded and double-stranded states of DNA double helix at the genomic loci harboring deamination and oxidation products of 5mC nucleotides as shown in FIGS. 38-39. This model predicted that DNA methylation associated with transcriptionally silent and transcriptionally active genomic loci would have markedly different effect on DNA dynamics depending on distinct processing mechanisms of 5mC and 5-hydroxy-methyl-cytosine (5hmC) nucleotides and cytosine recovery pathways as shown in FIGS. 38-39. Cytosine methylation and stable maintenance of 5mC would have no effect on DNA dynamics compared to the canonical DNA sequences. Deamination of 5mC and 5hmC would create nucleotide mismatches resembling wobble base pairing and increasing the responsiveness of DNA double helix to invading RNA molecules at the transcriptionally active loci. One of the important implications of this models was that non-coding RNA molecules may play an important role in epigenetic inheritance of transcriptionally-active genetic regions as shown in FIGS. 38-39. If confirmed, it would imply that DNA methylation played a highly important role in epigenetic inheritance of both transcriptionally silent and transcriptionally active genomic loci in a cell, therefore, orchestrating the maintenance and functional sustainability of the entire genetic landscape defining phenotypes.

Nano-Sensors for Electro-Based Detection

Example 11 Methods of Detection of Nano-Sensors' Engagement with Target Molecules Three example methods can be used for detection of nano-sensors' engagement with target nucleic acid molecules:

1. fluorescence-based detection shown in Examples 2-6;

2. gel electrophoresis-based detection shown in Example 7; and 3. transmission electron microscopy-based detection shown in the Example 7.

Importantly, interactions of nano-sensors with specific genetic targets can be visualized by detecting defined images and geometrical shapes, thus affording digital, computational, and web-based capabilities for capture and transmission of diagnostic information.

Other examples of methods of detection of nano-sensors' engagement with target molecules are shown in FIGS. 40A and 40B. In the examples shown in FIGS. 40A and 40B, the detection method is based on changes of the electrical charge of nano-devices after the specific engagement (hybridization) of nano-sensors with target nucleic acid molecules in accordance with some embodiments described herein.

FIG. 40A shows each single strand of nucleic acid (NA) having an amount of charge determined as (−)1 (arbitrary number). Therefore, after hybridization a double-stranded NA probe was composed of two single strands having negative charges of (−)2. This increase of negative charge changed resistivity of semiconductor and can be measured.

FIG. 40B shows that a single strand of NA opening strand hybridized with double-stranded tweezers having a charge of (−)2. Therefore, after hybridization the total amount of negative charges on opened tweezers was (−)3. This increase of negative charge changed resistivity of semiconductor and could be measured.

FIG. 41 shows another example of a nanosensor device of the disclosed technology, including an example SNP probe nucleic acid zipper-based tweezers device. For example, in operation, an electrical signal can be detected based on binding of target samples with the exemplary SNP probe tweezers device on an example graphene based electrode. For example, the nano-sensors' engagement with target molecules are based on changes of the electrical charge of nano-devices after the hybridization of nano-sensors with nucleic acid molecules.

Example 12 Single Mismatch Detection on Graphene FET

Materials and Methods

PASE, ethanolamine, $MgCl_2$ and conducting silver paste were obtained from Sigma Aldrich (Saint Louis, Mo.). Graphene (chemical vapor deposition (CVD) grown graphene) was from ACS material (Medford, Mass.). Silicone rubber was from Dow Corning (Midland, Mich.). PBS and Tris solution were from Thermo Fisher Scientific (Waltham, Mass.). Poly (methyl methacrylate) (PMMA) was from MicroChem (Westborough, Mass.). Ammonium persulfate was from MP Biomedicals (Solon, Ohio). DNA gels were from Lonza (Walkersville, Md.). Ultrapure water was obtained from a Millipore water purification system such as A10 water purification system having a resistivity of 18.2 MΩ. The FRDM KL-25Z microcontroller board was purchased from Freescale Semiconductor, Inc. A Bluetooth HC-06 module was purchased from Guangzhou HC Information Technology Co., Ltd. All DNA oligonucleotides were purchased from IDT (Coralville, Iowa) and all DNA sequences are listed in Table 7.

TABLE 7

| | DNA sequences used in the experiment | SEQ ID NO: |
|---|---|---|
| W | 5'-TEXAS RED 615-TGA AAG IGT TTT AAT AAT AGA ATT TTA AAA IAC TIG TAI ATT TTT TTT TTC TCT ATC AAT CTC TAA CAC CC | 38 |
| N | GGG TGT TAG AGA TTG ATA GAG CGG CCT TAT TTC TAC CAG TCT TTT AAA ATT CTA TTA TTA AAA CCC TTT CA-RQ | 39 |
| Perfect match T | TGA AAG GGT TTT AAT AAT AGA ATT TTA AAA GAC TGG TAG AAA TAA GG | 40 |
| Single mismatch T | TGA AAG GGT TTT AAT AAT ATA ATT TTA AAA GAC TGG TAG A AA TAA GG | 41 |
| Probe | 5'-TAA TAA TAG AAT TTT AAA AGA CTG GAA TAA-3' | 42 |
| Complementary DNA | 5'-TTA TTC CAG TCT TTT AAA ATT CTA TTA TTA-3' | 43 |
| Non-complementary DNA | 5'-ACT GAT GCA CTG ATT ACC TGC TAC GAT CGA-3' | 44 |
| N | GGGTGTTAGAGATTGATAGAGCGGCCTTATCCAGTATTTTAAAA TTCTATTATTA | 45 |
| W | TAATAAATIAATTTTAAAAIACTIITTTTTTTTTCTCTATCAATCTC TAACACCC | 46 |
| Perfect match DNA | TAATAATAGAATTTTAAAAGACTGGAATAA | 47 |
| Single mismatch DNA | TAA TAA TAG AAG TTT AAA AGA CTG GAA TAA | 48 |

Fabrication of Graphene FET Chip

The top side of graphene on copper film was spin-coated with PMMA to protect the Top side of graphene while the bottom side of graphene was etched away. PMMA acted as supporting layer of the graphene after etching copper. The back side of graphene was removed by oxygen plasma etching. The sample was cut into 4 mm×6 mm size with scissors. Copper was etched by floating on 0.1 M of ammonium persulfate for about 5 hours and rinsed in DI water overnight. The graphene supported by PMMA was then transferred on silicon oxide coated silicon wafer. PMMA layer was removed by acetone at 60° C. for 1 hour. The sample was annealed at 300° C. for 2 hour under hydrogen/argon atmosphere. To fabricate transistor, conducting silver paste was used as source and drain electrodes at the two ends of the graphene. Silicone rubber was applied to insulate source and drain electrodes from liquid and construct solution reservoir.

In another example, the graphene film was cut into 5 mm×8 mm size or ~2 mm×7 mm size with scissors. Graphene films were obtained from the maker prepared on thin copper substrates. The graphene was on the both side of the copper foil and only the top side was used for FET fabrication. To separate the graphene from the copper substrate PMMA was spin-coated on the top (carbon) surface of graphene/copper substrate to protect the graphene while the copper bottom was etched away. Copper was etched by floating on 0.1 M of ammonium persulfate for about 5 hours and rinsed in deionized (DI) water overnight. PMMA acted as a supporting layer to the graphene once the copper was etch away. The back side of graphene was removed by oxygen plasma etching. The graphene supported by PMMA was then transferred on silicon dioxide coated wafer followed by removal of the PMMA layer with acetone at 60° C. for 1 hour. The sample was then annealed at 300° C. for 2 hours under hydrogen/argon atmosphere. To fabricate transistor, conducting silver paste was used as source and drain electrodes at two ends of the graphene. Silicone rubber was then applied to insulate source and drain electrodes from liquid and also used as a solution reservoir.

Immobilization of DNA Zipper or Probe 5 mM of PASE in Dimethylformamide (DMF) was treated on the graphene for 1 hour and rinsed with pure DMF and DI water. 50 μM of DNA zipper or probe was added on PASE-modified graphene for 2 hours. The graphene FET with DNA zipper or probe functionalization was rinsed with 1×PBS. 100 mM of ethanolamine solution was treated to saturate the possibly unreacted amino group on PASE and rinsed with 1×PBS solution. All the volume of treated chemicals and samples was 40-50 μL.

Visualization of DNA and Graphene Surface

Topographic images of DNA on graphene surface were acquired to verify proper functionalization of DNA zipper or probe on the graphene channel, using a Multimode atomic force microscope (AFM) equipped with a Nanoscope V controller (Bruker) (FIG. 42). Silicon cantilevers with a spring constant of 42 N/m (PPP-NCHR, Nanosensor) were used for imaging in air using tapping mode. Silicon nitride cantilevers with spring constants of 0.08 N/m (OMCL-TR400, Olympus) were employed for imaging in fluid using peak force tapping mode. The Nanoscope Analysis software was used for analyzing imaging data.

Strand Displacement on the Chip

Strand displacement reaction was conducted by dropping appropriate concentration of perfect match and single mismatch T strands and incubated overnight in the reservoir on the graphene FET chip. Then the chip was rinsed gently with 1×PBS. All the volume of treated samples was 50 μL.

Detection of Strand Displacement on Graphene FET

The scheme of strand displacement on the graphene FET and single mismatch detection is shown in FIG. 43. The toehold part of N, which was adjacent to the graphene surface (FIG. 43, black dot circle), became double-stranded after strand displacement and it changed the electrical signals seen in the I-V curve and resistance. Thus, when T had a single mismatch to N, the affinity between N and T was significantly decreased and the reaction rate was greatly reduced; DNA zipper remained in its initial conformation. Sample in buffer solution was placed in the reservoir and a gate voltage was applied directly to the top of the buffer solution. When the surface charge was changed by strand displacement, the charge built up and the I-V curve shifted to left side and the resistance was increased. Perfect match and single mismatch samples were tested to investigate specificity of the sensor. Target strands were incubated on the sensor for 8 hours with different concentrations (100 pM to 10 µM). When perfect match T was treated on the graphene sensor, the U-shaped I-V curve shifted downside and leftside, which indicates increasing resistance and imposition of n-doping effect. With 100 pM of T strands, which is equivalent to about $3.011 \times 10^9$ of T molecules in 50 µL of buffer solution, DNA zipper showed clear discrimination of single mismatch (FIG. 44). As the concentration of perfect match T was increased, I-V curve kept shifting and the shape of the curve became flatten. As in the FIG. 44C, Dirac-point of the IV curve was shifted −50 mV with 10 µM of perfect match T while −11.6 mV with single mismatch T. Through the experiments, single mismatch T made much less shifts and the IV curve was saturated. Single mismatch T could not result in the proper strand displacement while perfect match T could. Resistance change of the channel was measured and compared with perfect match and single mismatch targets according to different concentrations. When DNA was accumulated on graphene surface, its resistance was increased (FIG. 45).

The graphene channel (4 mm×6 mm) was transferred onto a silicon oxide-coated wafer using an established method. 1-Pyrenebutanoic acid succinimidyl ester (PASE) was used to link graphene and amino group at the N strand of DS probe. The pyrene group of PASE and graphene was attracted to each other with π-π stacking interaction and the amino group at N and amide bond on PASE were covalently bound. The process of graphene functionalization was monitored at each step using AFM. As shown in FIG. 42A, topography of bare graphene surface was mostly flat with some defects. Graphene wrinkles are observed at an height of 4-7 nm and these were in good agreement to those found in other groups. PASE functionalization of graphene surface did not change flatness of the graphene (FIG. 42B). However, after immobilizing double strands DNA on the device through PASE and amine reaction, surface morphology dramatically changed due to appearance of globular structures (FIG. 42C). The average height of globular shape structures is 3.6+1.4 ranging from 2 to 6 nm (FIG. 16). The appearance of these structures seemed consistent with the conformation fo strand DNA strands in fluid. The typical height of lying flat double strand DNA detected by the air AFM is ~2 nm, which is shorter than the height of globular structure observed in the experiments performed in fluid. These structures must be due to the conformation of standing DNA strands in fluid. DNA strands on the device are further confirmed by imaging in air after drying the graphene surface (FIG. 42D). After drying, the appearance of dotted globular structures of dsDNA observed in fluid condition changed to distinctive rod shapes of ~2 nm in height as shown in details of the insent image (FIG. 42D). These observations were validated by the analyses of control AFM images of graphene and PASE functionalized surface, which were also imaged in air (FIG. 17). A DS probe consisted of a 40 bp double strand section and a 7 nt single strand overhang; in total the length was ~15 nm. Consistently, the rod shapes of the DNA strands in the air AFM images showed about 15-20 nm of length. AFM images indicated that the PASE-amine functionalization strategy was working appropriately.

The conformation of the DS probe on the graphene surface is an important factor on the electrical detection of strand displacement. As only 7 nt among 47 bps became double stranded before and after the strand displacement, if the DS probe was laid down or absorbed on the surface, the signal difference would be too small to be detectable by recognizing the charge difference. The AFM image of FIG. 42C showed that DS probe was observed as islands in liquid, while it was grain-boundary-shape in air (FIG. 42B). When the surface was fully covered by PASE and ethanolamine, the DS probe was not exposed and not absorbed into graphene except amine-amide bonding, otherwise pyrene group in DNA could be absorbed to graphene by Lx-nt stacking interaction. Additionally molecular dynamics simulation performed in literature showed that DNA established an upright conformation to the silica surface, flutuating only around 10° from vertical at stable state. The DS probe was perpendicular to the surface in liquid and the functionalization strategy was successful.

The source and drain electrodes were applied by silver paste and silicone rubber was used to insulate the electrodes and to create solution reservoir. Sample in buffer solution was placed in the reservoir and a gate voltage was applied directly to the top of the buffer solution. When the surface charge was changed by strand displacement, the charge built up and the I-V curve shifted to left side and the resistance was increased. Functionalization of DS probe changed electrical signals of FET (FIG. 48). The I-V curve was measured after PASE was fixed on the graphene channel with 1×PBS buffer solution as liquid gate. After DS probe was bonded on the PASE, the measurement was repeated. The I-V curve shifted to left side after bonding of DS probe. The unique U-shaped I-V curve was obtained during measurement due to the ambipolar characteristic of graphene. Additionally, the resistance increased and it shifted the I-V curve lower.

Debye length should be considered when detecting electrical charge in ionic solution. It can be written for aqueous solution at room temperature as $$\lambda(nm) = \frac{1}{\sqrt{4\pi l_B \sum_i z_i^2 \rho_i}}$$

where $\lambda$ is the Debye length which is expressed in nanometer, $l_B$ is Bjerrum length which is 0.7 nm, $z_i$ is valencies of the various types of ions and $\rho_i$ is number densities or number of molecules per volume. Note that it is an estimate of the distance where Coulomb interactions are ignored, so does the size of the region near a point charge where opposite-charge counterions can be found. It represents net length of electrostatic effect in ionic solution. Charges are electrically screened outside the sphere whose radius is the Debye length. In 1×PBS solution, which is generally used as DNA buffer solution, its debye length is less than 1 nm. More diluted PBS, such as 0.1 or 0.01×PBS, allows detection of longer part of the hybridization as reported. However, the DS probe requires a high ionic concentration to stably operate the strand displacement. If the ionic concentration of buffer solution is too low, its double helix structure can be unstable and can not result in proper strand displacement.

In the following test of strand displacement, 12.5 mM $MgCl_2$ and 30 mM Tris buffer was used for lengthier detection of DNA as this $MgCl_2$ concentration was known to be equivalent to about 1×PBS for DNA helix stabilization. $MgCl_2$ was 2:1 electrolyte (e.g. $Mg^{2+}$:$2Cl^-$) and its Debye length of 12.5 mM $MgCl_2$ was calculated by the above equation and was ~1.6 nm. The length of 1 nucleotide is known as 0.4 nm thus, about 4 nt can be detected in 12.5 MgCl buffer solution. However it was reported that the electrical effect of DNA rapidly decreased and that only a few sequences close to the graphene surface determined the electrostatic potential on the sensor. The tests were also conducted with 1×PBS and compared with $MgCl_2$ buffer solution. The $MgCl_2$ buffer solution generated clearer discrimination (FIG. 49).

FIG. 50 shows another set of data with different dimension of the graphene channel with great distinguishment of single mismatch. Considering the clear discrimination of single mismatch in 47 bp, it could be possible to discriminate single mismatch in a longer strand.

Resistance change of the channel was measured and compared with perfect match and single mismatch targets according to different concentrations. When DNA was accumulated on graphene surface, its resistance was increased. Immobilization of DS probe and addition of target strands increased the resistance of the channel. The resistance increased 40-60% when probe was anchored on the graphene surface. Subsequently perfect match and single mismatch T were tested with each concentration from 100 pM to 10 µM, which was equivalent to about $3.011 \times 10^9$ to $3.011 \times 10^{14}$ of T molecules in 50 µL of buffer solutions. The actual measurements were conducted at the same test of I-V curve measurement. As shown in the FIG. 44, perfect match T increased the resistance more than single mismatch T. The maximum difference was observed at the target concentration of 1 nM with resistance changes of ~26.0% and ~6.8% and the minimum difference was at the target concentration of 100 nM with resistance changes of ~84.9% and ~46.0% (1.8-fold difference), for perfect match and single mismatch respectively.

In control experiments, single strand probe was tested using only N strand of DS probe to confirm that the discrimination of single mismatch in 47 bps resulted from using DS probe. The single mismatch target strand was tested with concentrations ranging from 1 pM to 10 nM. FIG. 51 shows that when a single mismatch target strand was hybridized with N strand of the probe and its signal transferred as much as the DS probe with perfect match target. The concentration of T needed to saturate the IV curve transfer was much lower because it did not have W strand of DS probe. When it was a DS probe, T needed more energy (higher concentration) driving to displace W. Single mismatch target strand shared identical 27 nt and 19 nt with the perfect match target and the melting temperature of hybridization of single mismatch target and N strand was 55-65° C. with concentrations ranging from 10 pM to 10 µM. The stable hybridization of single mismatch target and N strand made discrimination of single mismatch impossible when the probe was single stranded. It confirms the capability of DS probe on graphene FET to discriminate single mismatch in long sequences. FIG. 52 demonstrates a data plot obtained with the nano-sensor disclosed herein has higher resolution than existing technology and has the ability to detect sequences greater than 30 bases.

Originally microarrays employed photolithography to fabricate micro-sized spot arrays inspired by transistors array in electronics. The proposed sensor can be also be intergrated in the form of microarray which does not need fluorescence labeling or optical components and can reduce number of spots by detecting longer strand. An example of the nano-sensor disclosed herein in a microarray format is illustrated in FIG. 53. High specificity of the sensor is capable of avoiding complex algorithms to analyze vague data on detection of SNP with current technology and this can contribute to more affordable and accurate cancer and genetic decrease diagnosis.

In another example, a graphene FET with two electrodes and a liquid gate chamber was fabricated to examine electrical sensing of DNA using DNA tweezers-based probes as shown in FIGS. 54A and 54B. The toehold part of N, located in the loop part which is adjacent to the graphene surface (FIG. 54A, black dotted circle), became double-stranded after the opening of DNA tweezers by strand displacement. This changed the electrical signals as shown in the I-V curve and the corresponding electrical resistance. DNA strand displacement-based probe namely, double stranded probe (DS probe) was reported to enhance the specificity of the DNA detection. Importantly, unlike the DS probe, DNA tweezers-base probe has more complex structure, and the center of the probe is attached to the graphene surface. Therefore, DNA tweezers do not stand up on the surface, but instead lay down on it. When the DNA tweezers were open, the triple stranded structure pushed the detecting portion closer to the surface resulting in a signal larger than that generated by the DS probe. The graphene chip fabrication and the probe immobilization were conducted following the previously established methods.

The graphene after transfer was characterized by Raman microscopy. The Raman spectrum of the graphene sample indicated high-quality monolayer graphene, as it shows typical Raman spectrum of a single layer graphene (FIG. 55A). Examination of the functionalized graphene surface was done using Atomic Force Microscopy (AFM). The graphene in FIG. 55B shows a flat surface with some wrinkles of about 1-2 nm in height. Upon immobilization on the graphene, the DNA tweezers were observed in the form of globular structures (FIG. 55C). These structures, which exhibit an average height of about 3.7±0.7 nm with features between ~2-8 nm are in good agreement with previously published data. The DNA tweezers stand up, being surrounded by the fluid medium, whereas in air the DNA lies flat on the graphene surface (FIG. 55E). AFM image of the graphene measured in air is shown in FIG. 56. After addition of the perfect match DNA, the globular structures decreased slightly in height to about 3.5±0.8 nm while growing in diameter from 17.6±3.3 nm for the unbound probe to 21.8±5.0 nm for the probe with the perfect match DNA (FIG. 55D). This observation is consistent with the fact that the newly bound strand adds to the size of the structure, which, along with steric repulsion between the different strands, results in a broader overall shape. The binding of the perfect match DNA can therefore be confirmed by AFM. The results demonstrate that the graphene on the fabricated FET sensor chip was a monolayer and the functionalization strategy was successful for the complex design of DNA tweezers.

To examine the specificity of the graphene FET sensor, perfect match and single-mismatch samples were tested. Target strands in different concentrations (100 nM to 100

μM) were incubated on the sensor overnight (FIG. 57). When the perfect-match T was treated on the graphene sensor, the U-shaped I-V curve shifted down and to the left, indicating increased resistance and imposition of the n-doping effect. As the concentration of target strands increased, DS probe showed clear discrimination of single mismatch (FIG. 57). As the concentration of the perfect-match T increased, I-V curve kept shifting left and down and the shape of the curve became flatter. As shown in the FIG. 57C, the Dirac point of the I-V curve was shifted approximately −95 mV with 10 μM of perfect-match T and approximately −2 mV with single-mismatch T (47.5-fold difference). The 47.5 fold difference achieved using DNA tweezers was ~10 times larger than the use of double-stranded probes in a previous report. The single-mismatch T made much smaller shift. A single-mismatch T could not result in the proper strand displacement, whereas a perfect-match T could induce a proper strand displacement. The resistance change of the channel was measured and compared between the perfect-match and the single-mismatch targets at different concentrations (FIG. 57). When DNA was accumulated on the graphene surface, its resistance increases. As shown in FIG. 57C, perfect-match T increased the resistance significantly more than single-mismatch T. Clear differences were observed at all the target concentrations from 100 nM to 100 μM and it showed much clearer discrimination of the single mismatch compared to previous experiments. After measurements on the probe station, the resistance was measured with wireless signaling. The data from the two measurement systems were well matched with ~1% difference.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

---

The invention claimed is:

1. A nucleic acid detection device, comprising:
a graphene chip that comprises a substrate, a graphene surface on the substrate, a conducting substance at two ends of the graphene surface to form a first electrode and a second electrode, and an insulating substance to insulate the first electrode and the second electrode, wherein the insulating substance further forms a solution reservoir on the graphene surface to receive a nucleic acid probe and a sample nucleic acid;
a double-stranded nucleic acid probe attached to the graphene surface of the reservoir, wherein the nucleic acid probe comprises a normal strand having a toehold at one end and a weak strand comprising one or more inosines substituting guanines; and
a microcontroller board that comprises a digital meter to measure electric current that passes through the graphene chip when an input voltage is applied to the graphene chip, and a communication module to send values of the measured electric current and the input voltage, wherein the microcontroller board further comprises a low-pass filter to filter input voltage.

2. The nucleic acid detection device of claim 1, further comprising a mobile device that receives the values from the communication module and processes the values to show resistance changes.

3. The nucleic acid detection device of claim 1, wherein the microcontroller board further comprises a moving-average filter.

4. The nucleic acid detection device of claim 3, wherein the microcontroller board further comprises a second-order moving-average filter.

5. The nucleic acid detection device of claim 1, wherein the substrate includes silicon dioxide coated wafer.

6. The nucleic acid detection device of claim 1, wherein the conducting substance includes conducting silver paste.

7. The nucleic acid detection device of claim 1, wherein the insulating substance includes silicone rubber.

8. The nucleic acid detection device of claim 1, wherein the communication module supports wireless communication.

9. A method of detecting or discriminating a nucleic acid having one or more mismatches, comprising:
contacting a double-stranded nucleic acid probe in a solution reservoir on a graphene chip such that the nucleic acid probe is attached to a graphene surface of the graphene chip, wherein the nucleic acid probe comprises a normal strand having a toehold at one end and a weak strand comprising one or more inosines substituting guanines;
contacting a control nucleic acid that is completely complementary to the normal strand with the nucleic acid probe attached to the graphene surface such that strand displacement occurs between the nucleic acid probe and the control nucleic acid;
measuring electric current that passes through the graphene chip when an input voltage is applied to the graphene chip during the strand displacement between the nucleic acid probe and the control nucleic acid using a microcontroller board that comprises a digital meter to obtain a first I-V curve, wherein the microcontroller board further comprises a low-pass filter to filter input voltage;
contacting a target nucleic acid that is partially complementary to the normal strand with the nucleic acid probe attached to the graphene surface such that strand displacement occurs between the nucleic acid probe and the target nucleic acid;
measuring electric current that passes through the graphene chip when an input voltage is applied to the graphene chip during the strand displacement between the nucleic acid probe and the target nucleic acid using the microcontroller board to obtain a second I-V curve;
sending the measured electric current and the input voltage using a communication module; and
comparing the second I-V curve with the first I-V curve, wherein a shift in the curve indicating the presence of one or more mismatches in the target nucleic acid.

10. The method of claim 9, wherein the measured electric current and the input voltage are transmitted to a mobile device using wireless communication.

* * * * *